United States Patent
Huang et al.

(10) Patent No.: US 10,697,977 B2
(45) Date of Patent: Jun. 30, 2020

(54) MASS SPECTROMETRY-CLEAVABLE CROSS-LINKER

(71) Applicant: The Regents of The University of California, Oakland, CA (US)

(72) Inventors: Lan Huang, Irvine, CA (US); Scott D. Rychnovsky, Irvine, CA (US); Clinton Yu, Laguna Hills, CA (US); Eric James Novitsky, Irvine, CA (US); Craig Bryant Gutierrez, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/613,065

(22) Filed: Jun. 2, 2017

(65) Prior Publication Data

US 2017/0350901 A1    Dec. 7, 2017

Related U.S. Application Data

(60) Provisional application No. 62/345,670, filed on Jun. 3, 2016.

(51) Int. Cl.
| | |
|---|---|
| *C07C 317/44* | (2006.01) |
| *G01N 33/68* | (2006.01) |
| *C07C 315/04* | (2006.01) |
| *B01D 15/34* | (2006.01) |
| *G01N 30/88* | (2006.01) |

(52) U.S. Cl.
CPC ........ *G01N 33/6848* (2013.01); *B01D 15/34* (2013.01); *C07C 315/04* (2013.01); *C07C 317/44* (2013.01); *G01N 33/6845* (2013.01); *G01N 2030/8831* (2013.01); *G01N 2560/00* (2013.01)

(58) Field of Classification Search
None
See application file for complete search history.

(56) References Cited

PUBLICATIONS

Neklyudov et al. (Russian Journal of General Chemistry, 2014, 84 (3), 562).*
Grekov et al. (Inst. Khim. Vysokomol. Zhurnal (Russian Edition), 1983, 49(9), 981) (Year: 1983).*
English Translation of Grekov et al. (Inst. Khim. Vysokomol. Zhurnal (Russian Edition), 1983, 49(9), 981) (Year: 1983).*
(Continued)

*Primary Examiner* — Sudhakar Katakam
*Assistant Examiner* — Jennifer C Sawyer
(74) *Attorney, Agent, or Firm* — Knobbe, Martens, Olson & Bear, LLP

(57) ABSTRACT

Provided herein is synthesis of a novel acidic acid residue targeting sulfoxide-containing MS-cleavable homobifunctional cross-linker. The novel mass spectrometry-cleavable cross-linking agents can be used in mass spectrometry to facilitate structural analysis of intra-protein interactions in proteins and inter-protein interactions in protein complexes. Also disclosed herein are data based on the novel MS-cleavable homobifunctional cross-linker that are complimentary to amine-reactive sulfoxide-containing MS-cleavable reagents.

17 Claims, 12 Drawing Sheets

Specification includes a Sequence Listing.

(56) References Cited

PUBLICATIONS

Apweiler, R. et al., Update on activities at the Universal Protein Resource (UniProt) in 2013, *Nucleic Acids Research*, vol. 41, pp. D43-D47, 2013.

Belsom, A. et al., Serum albumin domain structures in human blood serum by mass spectrometry and computational biology, *Molecular & Cellular Proteomics*, vol. 15.3, pp. 1105-1116, 2016.

Chen, Z. A. et al., Architecture of the RNA polymerase II-TFIIF complex revealed by cross-linking and mass spectrometry, *EMBO Journal*, vol. 29, No. 4, pp. 717-726, 2010.

Erzberger, J.P. et al., Molecular architecture of the 40S·eIF1·eIF3 translation initiation complex, *Cell*, vol. 158.5, pp. 1123-1135, Aug. 28, 2014.

Gutierrez, C.B. et al., Developing a Novel Acidic Residue Reactive and Sulfoxide-Containing MS-Cleavable Homobifunctional Cross-Linker for Probing Protein-Protein Interactions, Anal. Chem., vol. 88, pp. 8315-8322, 2016.

Kaake, R.M., et al., A new in vivo cross-linking mass spectrometry platform to define protein-protein interactions in living cells, *Molecular & Cellular Proteomics*, vol. 13.12, pp. 3533-3543, 2014.

Kao, A. et al., Development of a Novel Cross-linking Strategy for Fast and Accurate Identification of Cross-linked Peptides of Protein Complexes, *Mol Cell Proteomics*, 10.1074/mcp.M110.002212-17, 2011.

Leitner, A. et al., Chemical cross-linking/mass spectrometry targeting acidic residues in proteins and protein complexes, *Proc Natl Acad Sci U S A*, vol. 111, No. 26, pp. 9455-9460, 2014.

Zeng-Elmore, X. et al., Molecular architecture of photoreceptor phosphodiesterase elucidated by chemical cross-linking and integrative modeling, *J Mol Biol*, vol. 426.22, pp. 3713-3728, Nov. 11, 2014.

Herzog, F., et al., Structural Probing of a Protein Phosphatase 2A Network by Chemical Cross-Linking and Mass Spectrometry, *Science*, vol. 337, pp. 1348-1352, 2012.

Kao, A., et al., Development of a Novel Cross-linking Strategy for Fast and Accurate Identification of Cross-linked Peptides of Protein Complexes, *Molecular & Cellular Proteomics*, vol. 10, 10.1074/mcp.M110.002212, pp. 1-17, 2011.

Kao, A. et al., Mapping the Structural Topology of the Yeast 19S Proteasomal Regulatory Particle Using Chemical Cross-linking and Probabilistic Modeling *Molecular & Cellular Proteomics*, vol. 11, 10.1074/mcp.M112.018374, pp. 1566-1577, 2012.

Kasper, P.T., et al., An Aptly Positioned Azido Group in the Spacer of a Protein Cross-Linker for Facile Mapping of Lysines in Close Proximity, *ChemBioChem*, vol. 8, pp. 1281-1292, 2007.

Leitner, A., et al., Lysine-specific chemical cross-linking of protein complexes and identification of cross-linking sites using LC-MS/MS and the xQuest/xProphet software pipeline, *Nature Protocols*, vol. 9, No. 1, pp. 120-137, 2014.

Leitner, A., et al., Crosslinking and Mass Spectrometry: An Integrated Technology to Understand the Structure and Function of Molecular Machines, *Trends in Biochemical Sciences*, vol. 41, No. 1., pp. 20-32, 2016.

Liu, F., et al., Optimized fragmentation schemes and data analysis strategies for proteome-wide cross-link identification, *Nature Communications*, vol. 8, Article No. 15473, pp. 1-7, 2017.

Liu, J., et al., Dissecting Fission Yeast Shelterin Interactions via MICro-MS Links Disruption of Shelterin Bridge to Tumorigenesis *Cell Reports*, vol. 12, pp. 2169-2180, 2015.

Lu, Y., et al., Ionic Reagent for Controlling the Gas-Phase Fragmentation Reactions of Cross-Linked Peptides *Analytical Chemistry*, vol. 80, pp. 9279-9287, 2008.

Muller, M.Q., et al., Cleavable Cross-Linker for Protein Structure Analysis: Reliable Identification of Cross-Linking Products by Tandem MS, *Analytical Chemistry*, vol. 82, No. 16, pp. 6958-6968, 2010.

Novak, P., et al., Intra-Molecular Cross-Linking of Acidic Residues for Protein Structure Studies, *European Journal of Mass Spectrometry*, vol. 14, pp. 355-365, 2008.

Petrotchenko, E.V., et al., An Isotopically Coded CID-cleavable Biotinylated Cross-linker for Structural Proteomics, *Molecular & Cellular Proteomics*, vol. 10, 10.1074/mcp.M110.001420, pp. 1-8, 2011.

Rozen, S., et al., CSNAP Is a Stoichiometric Subunit of the COP9 Signalosome, *Cell Reports*, vol. 13, pp. 585-598, 2015.

Schilling, B., et al., MS2Assign, Automated Assignment and Nomenclature of Tandem Mass Spectra of Chemically Crosslinked Peptides, *Journal of the American Society for Mass Spectrometry*, vol. 14, pp. 834-850, 2003.

Shi, Y., et al., Structural Characterization by Cross-linking Reveals the Detailed Architecture of a Coatomer-related Heptameric Module from the Nuclear Pore Complex, *Molecular & Cellular Proteomics*, vol. 13, 10:1074/mcp.M114.041673, pp. 2927-2943, 2014.

Sinz, A., Chemical cross-linking and mass spectrometry to map three-dimensional protein structures and protein-protein interactions, *Mass Spectrometry Reviews*, vol. 25, pp. 663-682, 2006.

Walzthoeni, T., et al., Mass spectrometry supported determination of protein complex structure, *Current Opinion in Structural Biology*, vol. 23, pp. 252-260, 2013.

Wang, X., et al., Mass Spectrometric Characterization of the Affinity-Purified Human 26S Proteasome Complex, *Biochemistry*, vol. 46, pp. 3553-3565, 2007.

Yang, L., et al., pcPIR, a photocleavable and mass spectrometry identifiable cross-linker for protein interaction studies, *Analytical Chemistry*, pp. vol. 82, No. 9. pp. 3556-3566, 2010.

Yu, C., et al., Developing a Multiplexed Quantitative Cross-linking Mass Spectrometry Platform for Comparative Structural Analysis of Protein Complexes, *Analytical Chemistry*, vol. 88, No. 20, pp. 10301-10308, 2016.

Yu, C., et al., Developing New Isotope-Coded Mass Spectrometry-Cleavable Cross-Linkers for Elucidating Protein Structures, *Analytical Chemistry*, vol. 86, pp. 2099-2106, 2014.

Yu, C., et al., Gln40 deamidation blocks structural reconfiguration and activation of SCF ubiquitin ligase complex by Nedd8, *Nature Communications*, vol. 6, Article No. 10053, pp. 1-12, 2015.

Zhang, H., et al., Identification of Protein-Protein Interactions and Topologies in Living Cells with Chemical Cross-linking and Mass Spectrometry, *Molecular & Cellular Proteomics*, vol. 8, pp. 409-420, 2009.

Winter, S., et al., EASI-tag enables accurate multiplexed and interference-free MS2-based proteome quantification, Nature Methods, vol. 15, pp. 527-530, 2018.

Winter, S., et al., EASI-tag enables accurate multiplexed and interference-free MS2-based proteome quantification, Nature Methods, vol. 15, Supplementary Information, 2018.

Yu, C., et al., Gln40 deamidation blocks structural reconfiguration and activation of SCF ubiquitin ligase complex by Nedd8, Nature Communication, 6:10053, DOI: 10.1038/ncomms10053, 2015.

\* cited by examiner

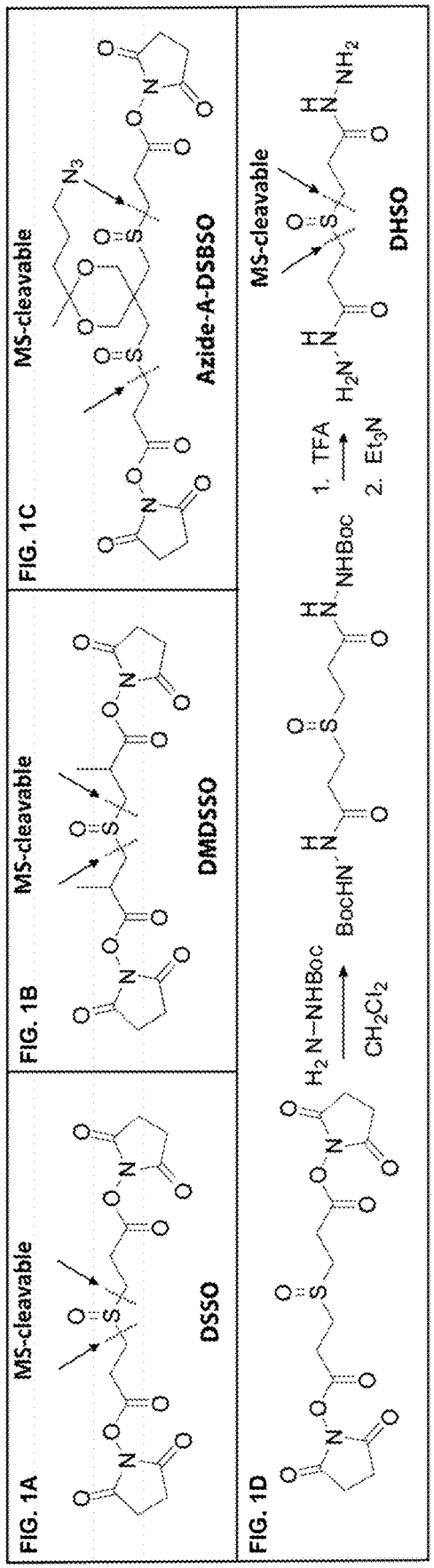

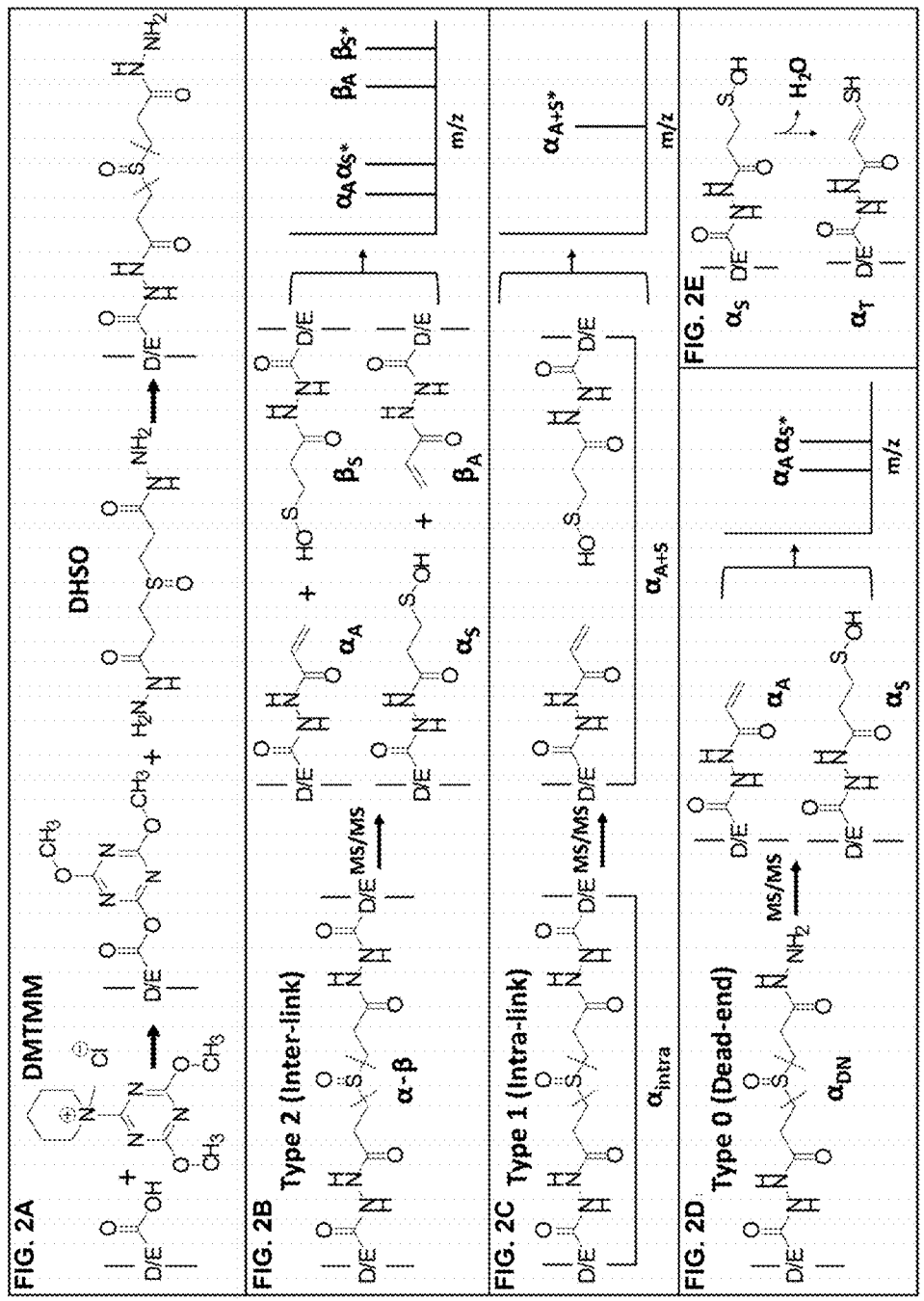

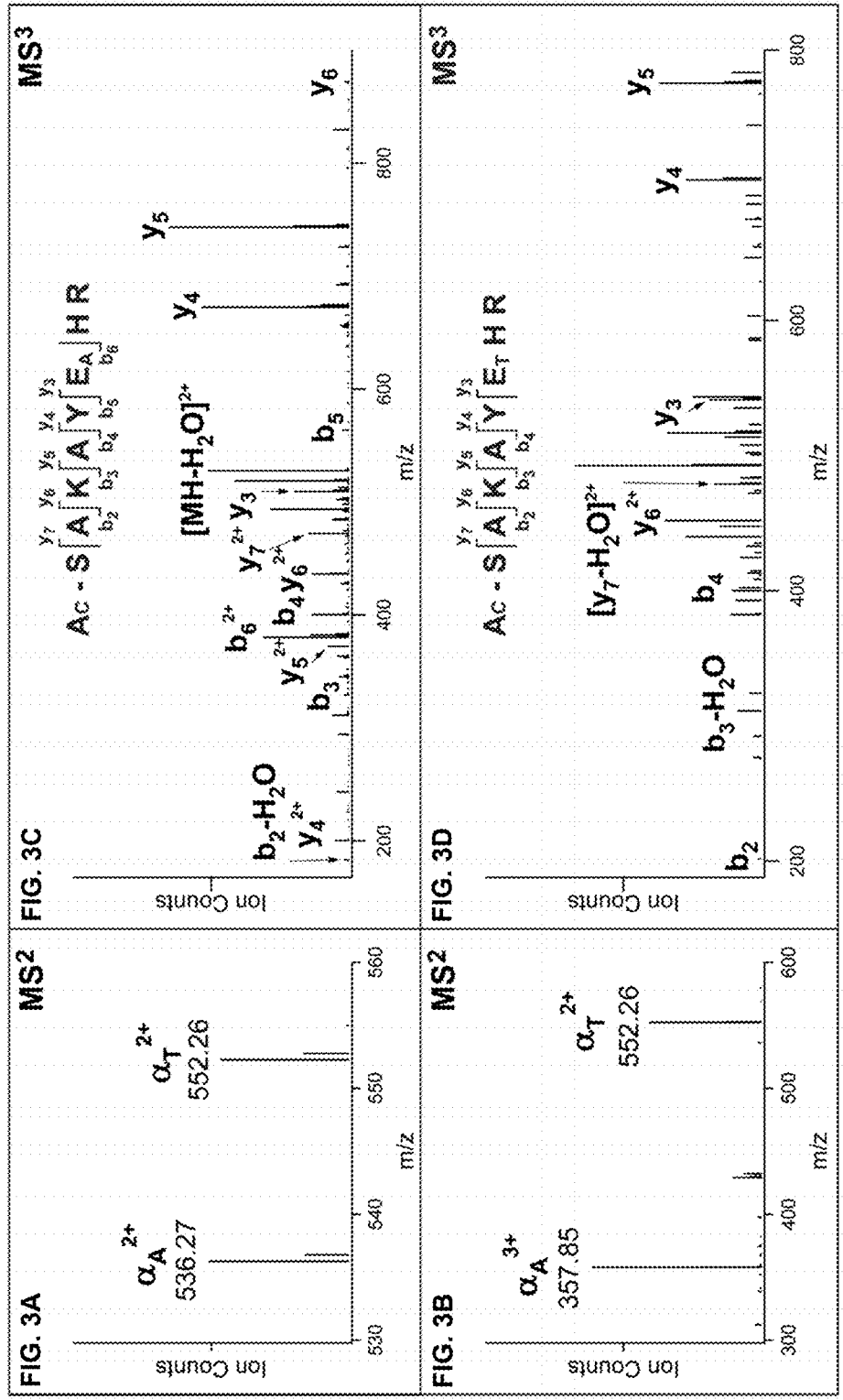

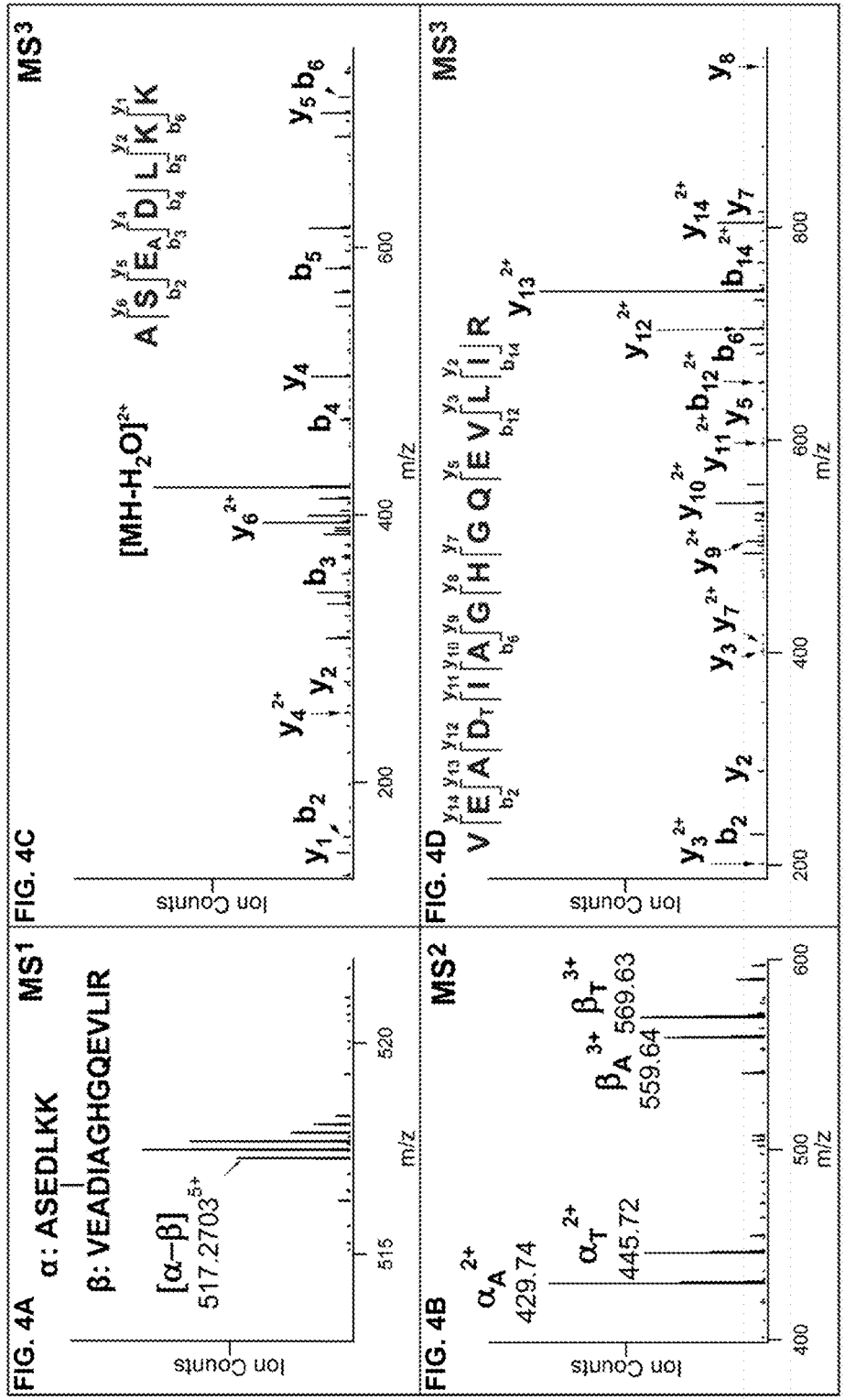

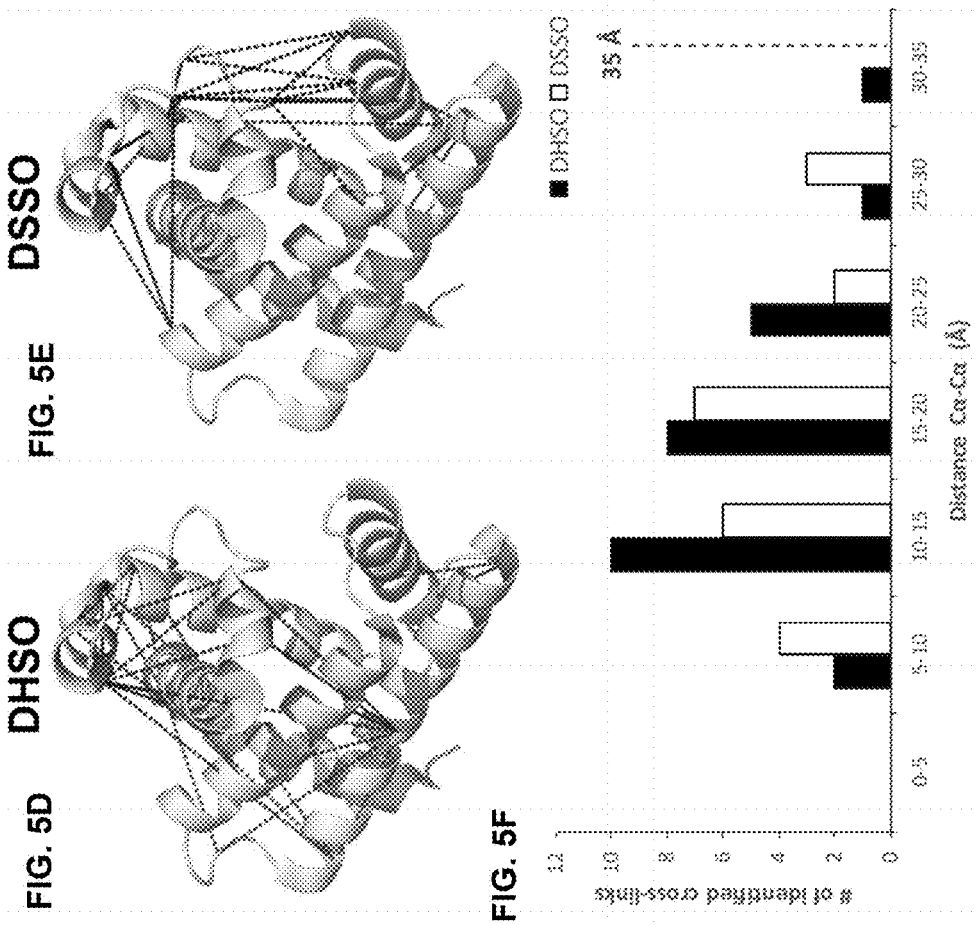
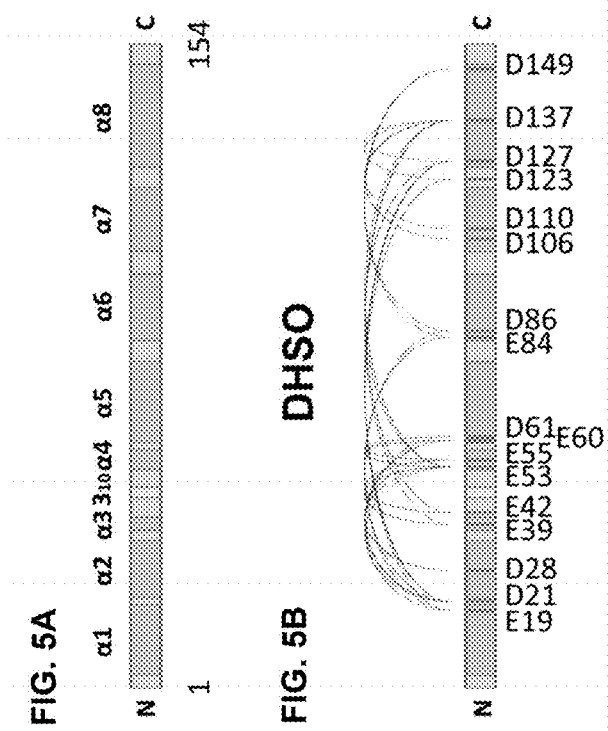

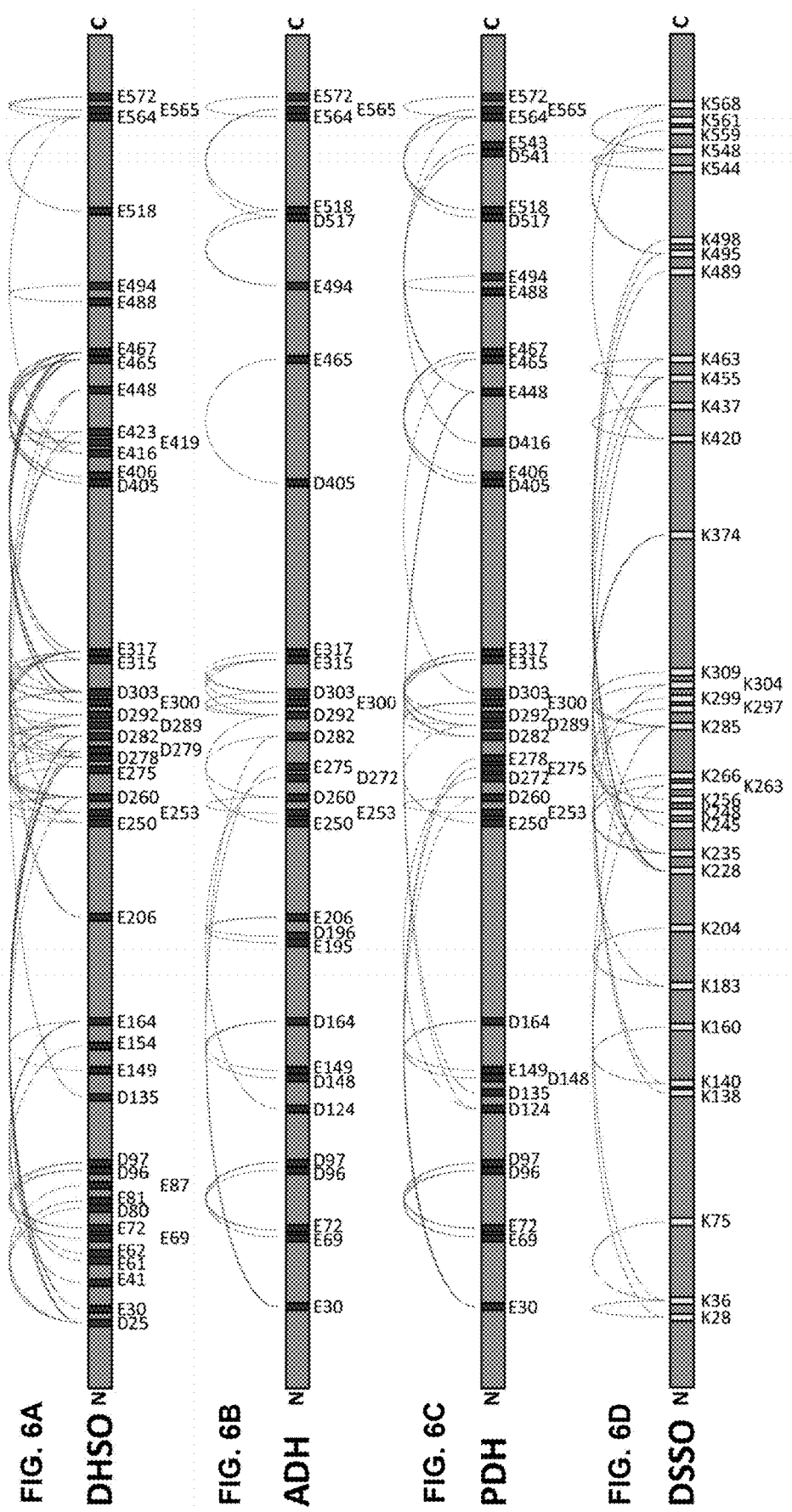
FIG. 6A DHSO  FIG. 6B ADH  FIG. 6C PDH  FIG. 6D DSSO

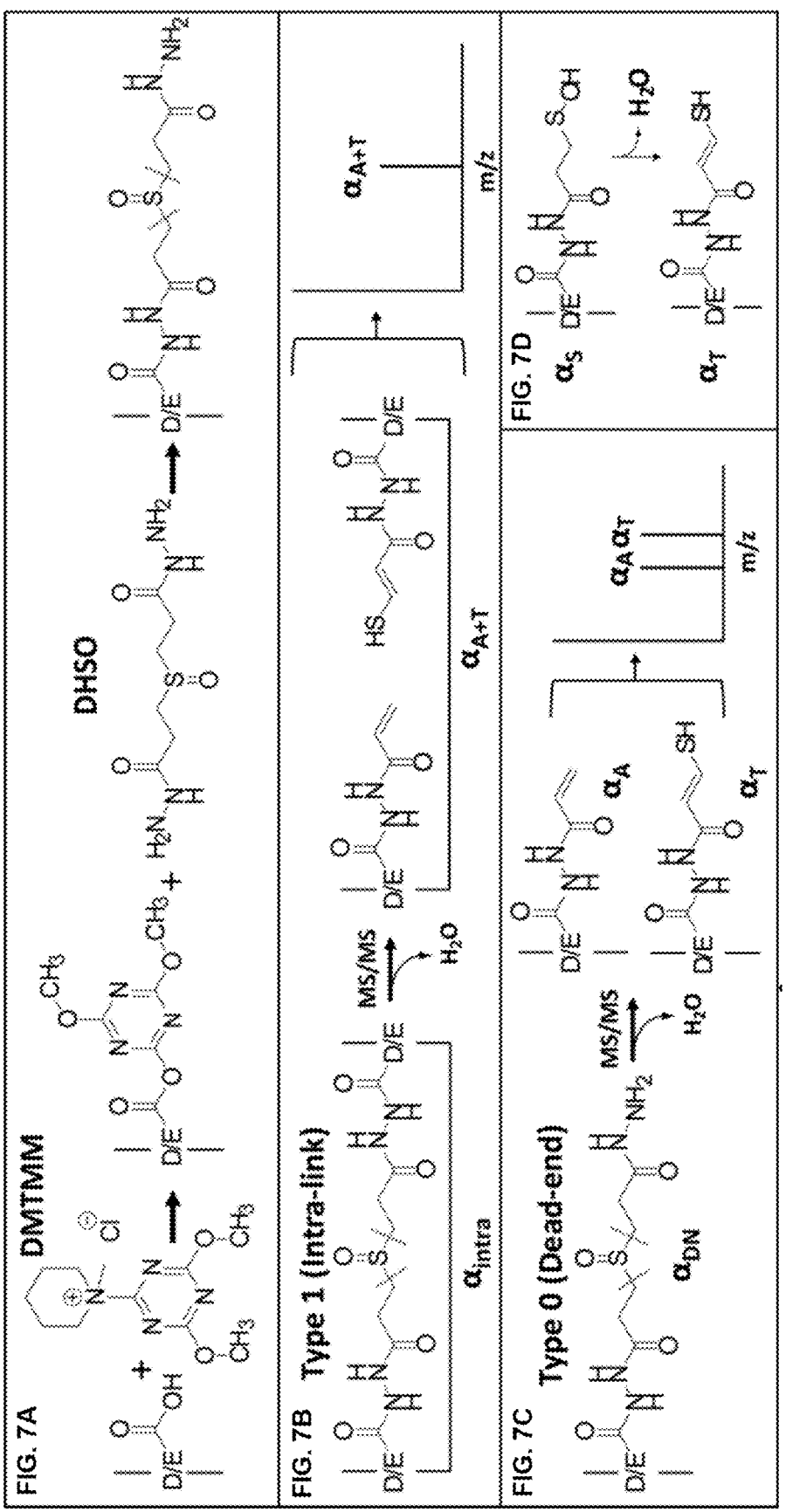

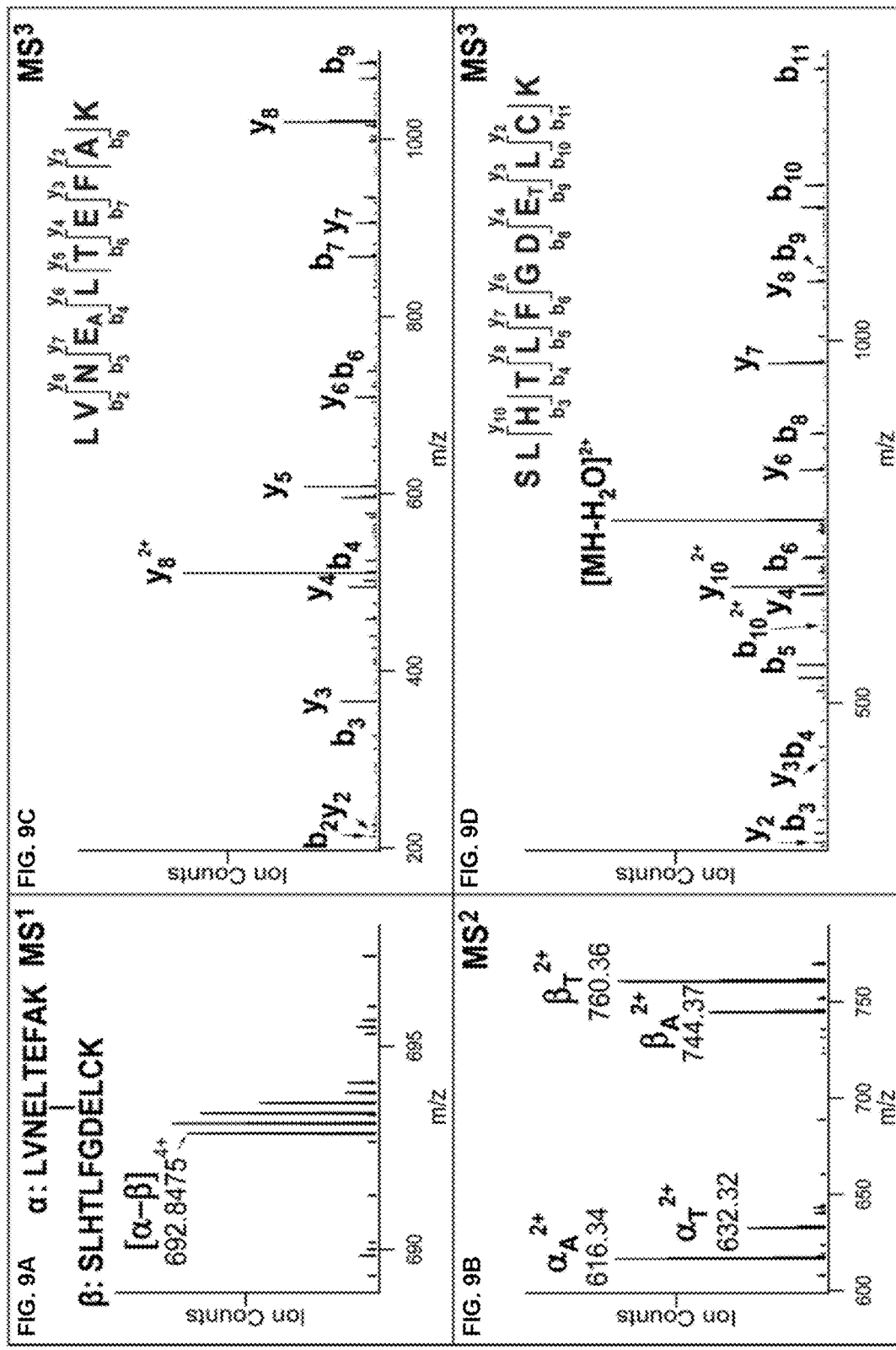

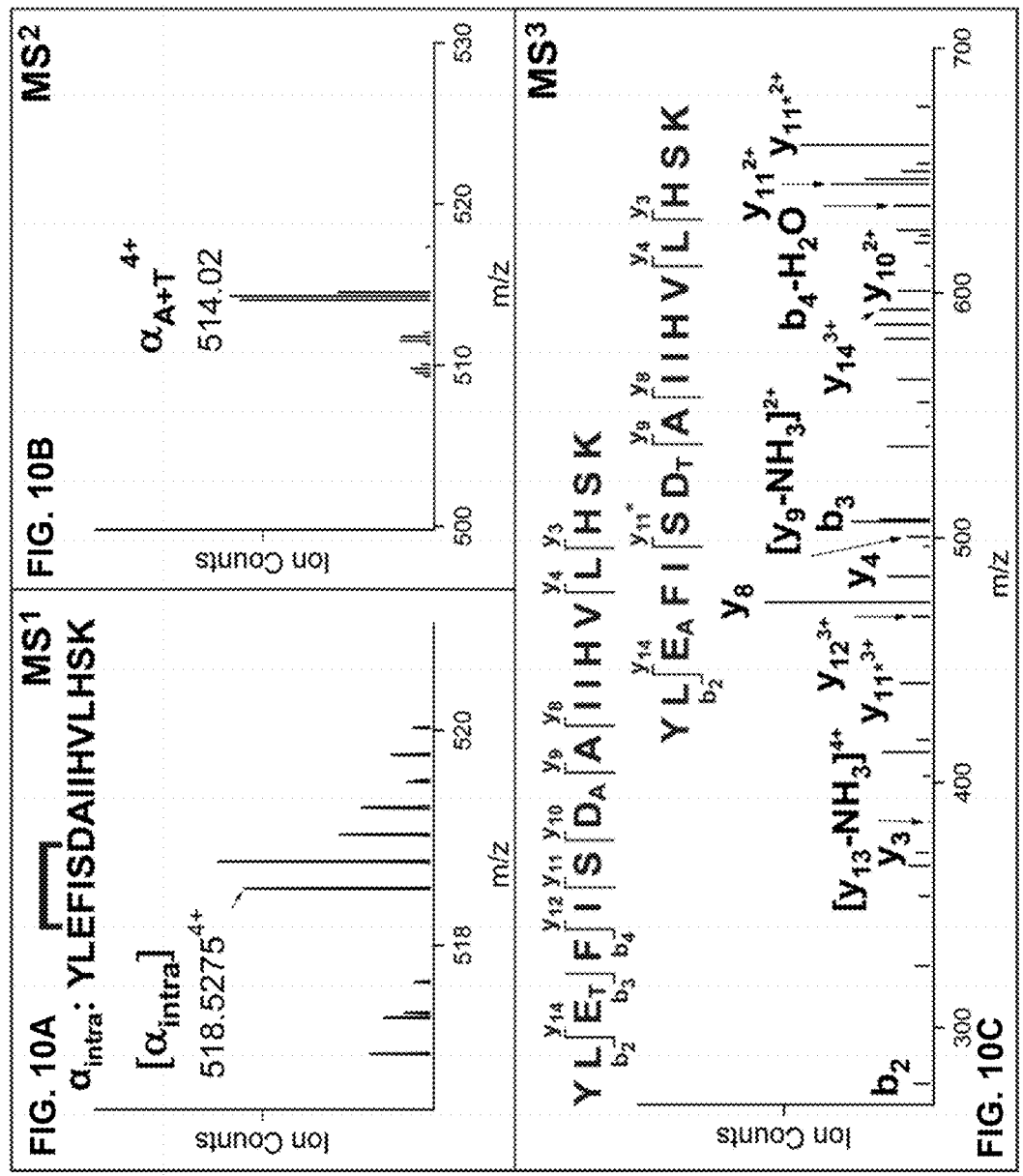

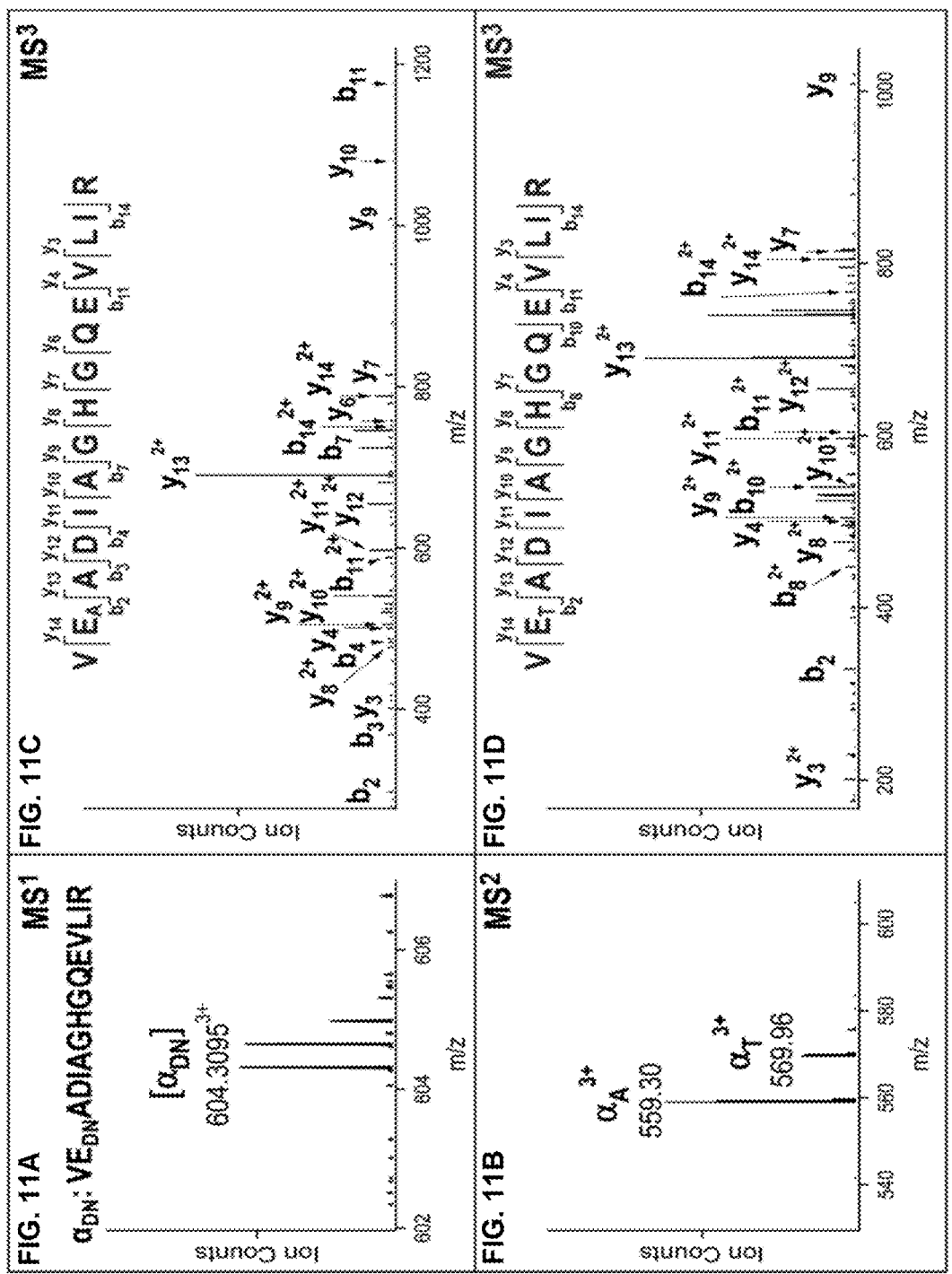

MASS SPECTROMETRY-CLEAVABLE CROSS-LINKER

PRIORITY AND CROSS-REFERENCE TO RELATED APPLICATIONS

This application claims the benefit of U.S. Provisional Application No. 62/345,670, filed on Jun. 3, 2016, which is hereby incorporated by reference in its entirety.

STATEMENT REGARDING FEDERALLY SPONSORED RESEARCH OR DEVELOPMENT

This invention was made with Government support under Grant No. R01GM074830, R01GM074830-1052, and R01GM106003 awarded by the National Institutes of Health. The Government has certain rights in this invention.

SEQUENCE LISTING IN ELECTRONIC FORMAT

The present application is being filed along with a Sequence Listing as an ASCII text file via EFS-Web. The Sequence Listing is provided as a file entitled UCI012003ASEQLIST.txt, created and last saved on Jun. 2, 2017, which is 58,182 bytes in size. The information in the electronic format of the Sequence Listing is incorporated herein by reference in its entirety in accordance with 35 U.S.C. § 1.52(e).

BACKGROUND

Field

The present disclosure relates generally to mass spectrometry-cleavable cross-linkers and methods of using mass spectrometry-cleavable cross-linkers for probing proteins and protein complexes.

Description of the Related Art

The majority of proteins exert their functions in the form of protein complexes. These macromolecular assemblies and their protein-protein interactions play critical roles in regulating integral biological processes. As a result, perturbations of endogenous protein-protein interactions can result in deleterious effects on cellular activities.

Structural analyses of these complexes by traditional biophysical structural techniques such as x-ray crystallography and nuclear magnetic resonance (NMR) are frequently utilized to elucidate their topologies. Unfortunately, many large and heterogeneous complexes are refractory to such methods, ushering the development of new hybrid structural strategies.

SUMMARY

In some embodiments, an MS-cleavable cross-linker is provided. In some embodiments, the MS-cleavable cross-linker comprises at least one hydrazide reactive group, at least one sulfoxide group, and at least one collision-induced dissociation (CID) cleavable bond, wherein the MS-cleavable cross-linker is configured for mapping intra-protein interactions in a protein, or inter-protein interactions in a protein complex, or combinations thereof.

In some embodiments of the MS-cleavable cross-linker, the at least one hydrazide reactive group is configured to react with an activated acidic side chain in the protein or protein complex. In some embodiments of the MS-cleavable cross-linker, the at least one CID cleavable bond is a C—S bond adjacent to the at least one sulfoxide group. In some embodiments of the MS-cleavable cross-linker, the MS-cleavable cross-linker is dihydrazide sulfoxide (DHSO), having the structure:

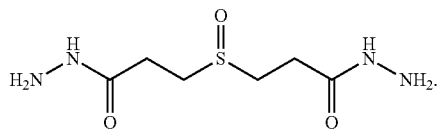 [SMILES: NNC(=O)CCS(=O)CCC(=O)NN]

In some embodiments of the MS-cleavable cross-linker, the two hydrazide reactive groups are separated by a 12.5 Å long spacer arm comprising the two symmetrical CID cleavable C—S flanking the one sulfoxide group.

In some embodiments, a method for synthesis of an MS-cleavable cross-linker is provided. In some embodiments, the method for synthesis of an MS-cleavable cross-linker comprises the steps of (i) providing disuccinimidyl sulfoxide (DSSO) in dicholormethane, (ii) adding tert-butyl carbazate to derive a first solution, (iii) stirring the first solution of step (ii), (iv) adding trifluoroacetic acid to derive an second solution, (v) stirring the second solution of step (iv), (vi) removing solvent from the second solution of step (v) in vacuo to derive an oil, (vii) dissolving the oil from step (vi) in methanol and adding trimethylamine to obtain a mixture, (viii) stirring the mixture from step (vii) to obtain a precipitate, (ix) collecting the precipitate from step (viii), washing the precipitate in fresh methanol, and drying the precipitate in vacuo, thereby obtaining the MS-cleavable cross-linker.

In some embodiments of the method for synthesis, stirring the first solution of step (ii) is performed at room temperature. In some embodiments of the method for synthesis, stirring the first solution of step (ii) is performed for about 6 h to about 24 h. In some embodiments of the method for synthesis, stirring the second solution of step (iv) is performed at room temperature. In some embodiments of the method for synthesis, stirring the second solution of step (iv) is performed for about 36 h to about 144 h. In some embodiments of the method for synthesis, stirring the mixture is performed at room temperature. In some embodiments of the method for synthesis, stirring the mixture is performed for about 10 min to about 40 min. In some embodiments of the method for synthesis, collecting the precipitate from step (viii), washing the precipitate in fresh methanol is performed about 1 to about 10 times. In some embodiments of the method for synthesis, the MS-cleavable cross-linker is DHSO, having the structure:

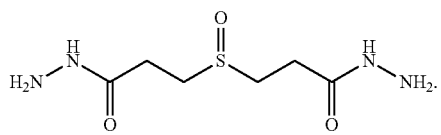

In some embodiments, a method for mapping intra-protein interactions in a protein, inter-protein interactions in a protein complex, or combinations thereof is provided. In some embodiments, the method for mapping intra-protein interactions comprises providing 4-(4,6-dimethoxy-1,3,5- triazin-2-yl)-4-methylmorpholinium chloride (DMTMM) as an activating agent, activating at least one acidic residue by DMTMM in the protein or protein complex, providing an MS-cleavable cross-linker, wherein the MS-cleavable cross-linker comprises at least one hydrazide reactive group, at least one sulfoxide group, and at least one CID cleavable bond, cross-linking the MS-cleavable cross-linker to the at least one activated acidic residue in the protein or protein complex, digesting with an enzyme the protein or protein complex cross-linked to the MS-cleavable cross-linker, generating one or more peptide fragments of the protein or protein complex, wherein the one or more peptide fragments are chemically cross-linked to the MS-cleavable cross-linker, and identifying the one or more peptide fragments using tandem mass spectrometry (MS$^n$), thereby mapping intra-protein interactions in the protein and/or inter-protein interactions in the protein complex.

In some embodiments of the method for mapping intra-protein interactions, the MS-cleavable cross-linker is DHSO, having the structure

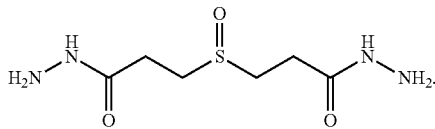 [SMILES: NNC(=O)CCS(=O)CCC(=O)NN]

In some embodiments, a method for cross-linking mass spectrometry (XL-MS) for identifying one or more cross-linked peptides is provided. In some embodiments, the method for XL-MS comprises providing 4-(4,6-dimethoxy-1,3,5-triazin-2-yl)-4-methylmorpholinium chloride (DMTMM) as an activating agent, activating at least one acidic residue by DMTMM in a protein or a protein complex, providing an MS-cleavable cross-linker, wherein the MS-cleavable cross-linker comprises at least one hydrazide reactive group, at least one sulfoxide group, and at least one CID cleavable bond, cross-linking the MS-cleavable cross-linker to the at least one activated acidic residue in the protein or protein complex, digesting with an enzyme the protein or protein complex cross-linked to the MS-cleavable cross-linker, generating one or more peptide fragments of the protein or protein complex, wherein the one or more peptide fragments are chemically cross-linked to the MS-cleavable cross-linker, performing a liquid chromatography-tandem mass spectrometry (LC-MS$^n$) analysis on the one or more cross-linked peptides, wherein the LC-MS$^1$ analysis comprises detecting the one or more cross-linked peptides by MS$^1$ analysis, selecting the one or more cross-linked peptides detected by MS$^1$ for MS$^2$ analysis, selectively fragmenting the at least one CID cleavable bond and separating the one or more cross-linked peptides during MS$^2$ analysis, sequencing the one or more cross-linked peptides separated during MS$^2$ analysis by MS$^3$ analysis, and integrating data obtained during MS$^1$, MS$^2$ and MS$^3$ analyses to identify the one or more cross-linked peptides.

In some embodiment of the method for XL-MS, the MS-cleavable cross-linker is DHSO, having the structure

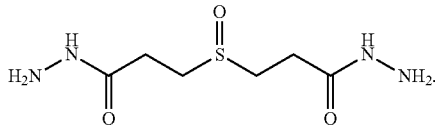 [SMILES: NNC(=O)CCS(=O)CCC(=O)NN]

BRIEF DESCRIPTION OF THE DRAWINGS

FIG. 1A shows structure of sulfoxide containing MS-cleavable cross-linker DSSO[16].

FIG. 1B shows structure of sulfoxide containing MS-cleavable cross-linker DMDSSO[17].

FIG. 1C shows structure of sulfoxide containing MS-cleavable cross-linker Azide-A-DSBSO[18].

FIG. 1D shows an embodiment of a synthesis scheme of MS-cleavable cross-linker DHSO.

FIG. 2A-FIG. 2E show characteristic MS$^2$ fragmentation patterns for DHSO cross-linked peptides.

FIG. 2A shows a scheme of peptide cross-linking by DHSO in the presence of DMTMM.

FIG. 2B shows MS$^2$ fragmentation of DHSO inter-linked heterodimer α-β.

FIG. 2C shows MS$^2$ fragmentation of DHSO intra-linked peptide αintra.

FIG. 2D shows MS$^2$ fragmentation of dead-end modified peptide αDN.

FIG. 2E shows an embodiment of a conversion scheme of αS to αT.

FIG. 3A-FIG. 3D show MS$^n$ analysis of DHSO inter-linked Ac-SR8 peptide.

FIG. 3A shows MS$^2$ spectra of DHSO interlinked Ac-SR8 at charge state $[\alpha$-$\alpha]^{4+}$ (m/z 548.7623$^{4+}$).

FIG. 3B shows MS$^2$ spectra of DHSO interlinked Ac-SR8 at charge state $[\alpha$-$\alpha]$5+ (m/z 439.2117$^{5+}$).

FIG. 3C shows MS$^3$ spectra of MS$^2$ fragment ion αA (m/z 536.27$^{2+}$).

FIG. 3D shows MS$^3$ spectra of MS$^2$ fragment ion $\beta_T$ (m/z 552.26$^{2+}$), which were detected in FIG. 3A.

FIG. 4A-FIG. 4D show MS$^n$ analysis of a representative DHSO inter-linked Myoglobin peptide.

FIG. 4A shows MS spectrum of a DHSO inter-linked myoglobin peptide α-β (m/z 517.2703$^{5+}$).

FIG. 4B shows MS$^2$ spectrum of the cross-linked peptide detected in FIG. 4A.

FIG. 4C shows MS$^3$ spectra of MS$^2$ fragment ion $\alpha_A$ (m/z 429.74$^{2+}$).

FIG. 4D shows MS$^3$ spectra of MS$^2$ fragment ion $\beta_T$ (m/z 569.63$^{3+}$).

FIG. 5A-FIG. 5F show myoglobin cross-link maps.

FIG. 5A shows myoglobin linear sequence showing locations of the 8 α-helices (α1-α8) and 3$_{10}$ helix.

FIG. 5B shows DHSO cross-link map on myoglobin linear sequence.

FIG. 5C shows DSSO cross-link map on myoglobin linear sequence.

FIG. 5D shows DHSO cross-link map on myoglobin crystal structure (PDB: 1DWR).

FIG. 5E shows DSSO cross-link map on myoglobin crystal structure (PDB: 1DWR).

FIG. 5F shows a graph of the distribution plot of identified linkages versus their spatial distances between D|E-D|E for DHSO (black bars) or K-K for DSSO (white bars) in myoglobin structure.

FIG. 6A-FIG. 6D show BSA cross-link maps on its linear sequence.

FIG. 6A shows DHSO cross-link map.

FIG. 6B shows ADH cross-link map.

FIG. 6C shows PDH cross-link map.

FIG. 6D shows DSSO cross-link map.

FIG. 7A-FIG. 7D show characteristic MS$^2$ fragmentation patterns for DHSO cross-linked peptides.

FIG. 7A shows the scheme of peptide cross-linking by DHSO in the presence of DMTMM.

FIG. 7B shows MS$^2$ fragmentation of DHSO intra-linked peptide $\alpha_{intra}$.

FIG. 7C shows dead-end modified peptide $\alpha_{DN}$.

FIG. 7D shows the conversion scheme of $\alpha_S$ to $\alpha_T$.

FIG. 9A-FIG. 9D show MS$^n$ analysis of a representative DHSO inter-linked BSA peptide.

FIG. 9A shows MS spectrum of a DHSO interlinked BSA peptide α-β (m/z 692.8475$^{4+}$).

FIG. 9B shows MS$^2$ spectrum of the cross-linked peptide detected in FIG. 9A.

FIG. 9C shows MS$^3$ spectra of MS$^2$ fragment ions $\alpha_A$ (m/z 616.34$^{2+}$).

FIG. 9D shows MS$^3$ spectra of MS$^2$ fragment ions $\beta_T$ (m/z 760.36$^{2+}$).

FIG. 10A-FIG. 10C show MS$^n$ analysis of a DHSO intra-linked myoglobin peptide.

FIG. 10A shows MS spectrum of a DHSO intra-linked myoglobin peptide $\alpha_{intra}$ (m/z 518.5275$^{4+}$).

FIG. 10B shows MS$^2$ spectrum of the intra-linked peptide in FIG. 10A.

FIG. 10C shows MS$^3$ spectrum of the MS$^2$ fragment ion $\alpha_{A+T}$ (m/z 514.02$^{4+}$).

FIG. 11A-FIG. 11D show MS$^n$ analysis of a DHSO dead-end modified myoglobin peptide.

FIG. 11A shows MS spectrum of a DHSO dead-end modified myoglobin peptide $\alpha_{DN}$ (604.3095$^{3+}$).

FIG. 11B shows MS$^2$ spectrum of the parent ion detected in FIG. 11A.

FIG. 11C shows MS$^3$ spectra of MS$^2$ fragment ions $\alpha_A$ (m/z 559.30$^{3+}$).

FIG. 11D shows MS$^3$ spectra of MS$^2$ fragment ions $\alpha_T$ (m/z 569.96$^{3+}$).

DETAILED DESCRIPTION

Introduction

The majority of proteins exert their functions in the form of protein complexes. These macromolecular assemblies and their protein-protein interactions play critical roles in regulating integral biological processes. As a result, perturbations of endogenous protein-protein interactions can result in deleterious effects on cellular activities. Structural analyses of these complexes by traditional biophysical structural techniques such as x-ray crystallography and nuclear magnetic resonance (NMR) are frequently utilized to elucidate their topologies. Unfortunately, many large and heterogeneous complexes are refractory to such methods, ushering the development of new hybrid structural strategies.

Chemical cross-linking coupled with mass spectrometry (XL-MS) has emerged as a powerful and popular approach for delineating the protein interactions within large multi-subunit protein complexes[1,2]. Moreover, cross-linking can capture temporal protein interactions by forming covalent bonds between proximal amino acid residues, effectively freezing transient interactions and providing information on the identities and spatial orientations of interacting proteins simultaneously. These linkages are then utilized as distance constraints to facilitate three-dimensional modeling of protein complexes by refining existing high-resolution protein structures or complementing lower resolution biophysical structural techniques (e.g. cryo-electron microscopy) in order to position individual protein subunits or interacting regions[3-9].

Elucidating the structure of protein complexes is paramount for understanding their functions. Recent technological advancements in cross-linking mass spectrometry (XL-MS) have made it a powerful methodology for defining protein-protein interactions and elucidating architectures of large protein complexes. However, one of the inherent challenges in MS analysis of cross-linked peptides is their unambiguous identification. One of the major challenges in conventional XL-MS studies is unambiguous identification of cross-linked peptides, due to difficulty in interpreting convoluted tandem mass spectra resulting from the fragmentation of covalently linked peptides.

To this end, various types of cleavable cross-linkers have been developed to facilitate and simplify MS identification of cross-linked peptides, such as UV-photocleavable[10], chemical-cleavable[11], and MS-cleavable reagents[12-18]. Of these, MS-cleavable cross-linkers appear to be the most attractive option due to their capability to improve the identification of cross-linked peptides by separating inter-linked peptides during MS analysis.

Figure 8:
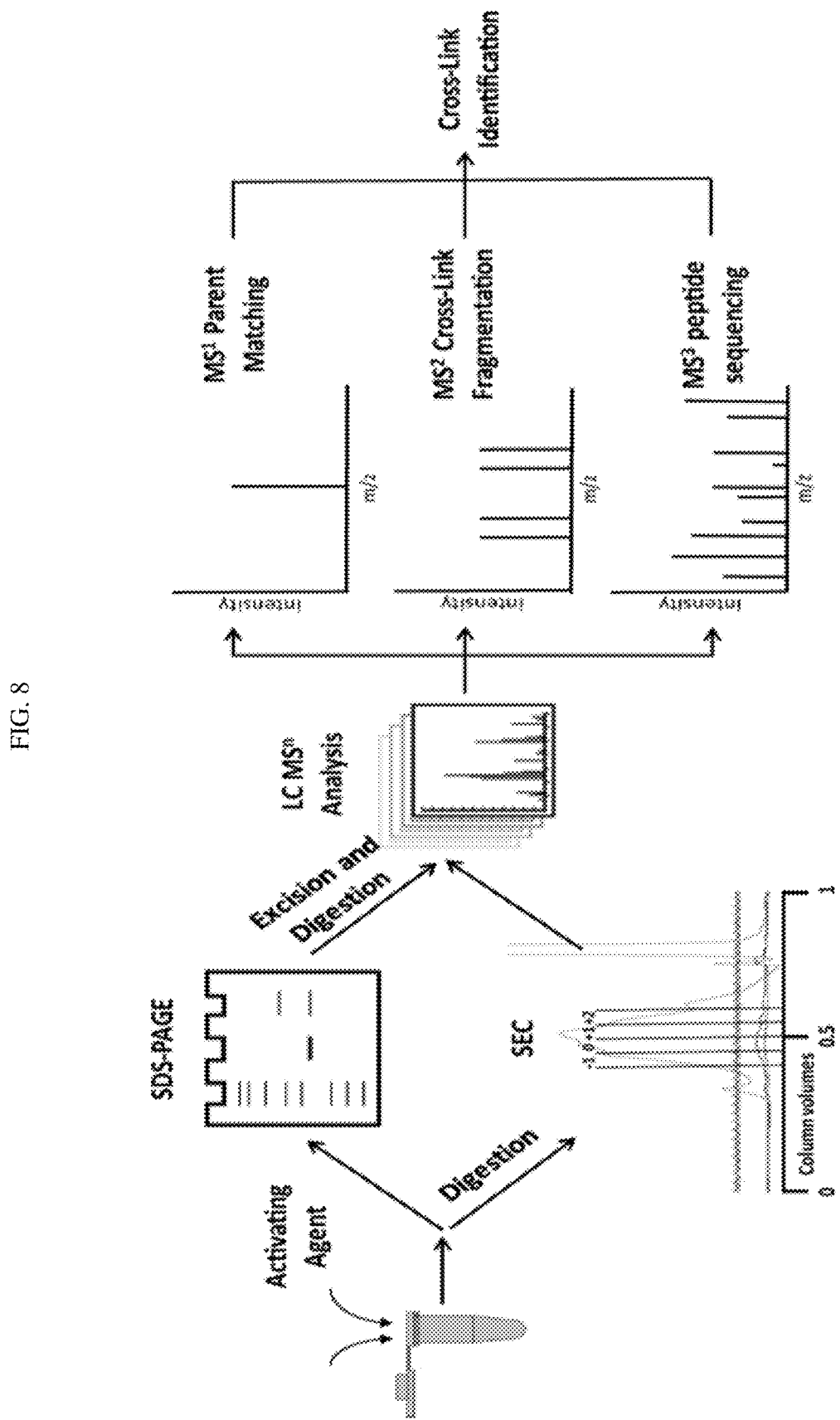
FIG. 8 shows an embodiment of the general XL-MS workflow for the identification of cross-linked DHSO peptides from proteins.

To facilitate this process, the inventors have previously developed a series of amine-reactive sulfoxide-containing MS-cleavable cross-linkers. These MS-cleavable reagents have allowed the inventors to establish a common robust XL-MS workflow (for example, FIG. 8) that enables fast and accurate identification of cross-linked peptides using multi-stage tandem mass spectrometry (MS$^n$). Although amine reactive reagents targeting lysine residues are successful, it remains difficult to characterize protein interaction interfaces with little or no lysine residues. In recent years, the inventors have developed a new class of MS-cleavable cross-linking reagents containing sulfoxide group(s) within their spacer regions, i.e., disuccinimidyl sulfoxide (DSSO)[16], dimethyl disuccinimidyl sulfoxide (DMDSSO)[17], Azide-tagged Acid-cleavable DiSuccinimidyl BisSulfoxide (Azide-A-DSBSO)[18] (FIG. 1A-FIG. 1C).

These MS-cleavable reagents contain symmetric MS-labile C—S bonds (adjacent to the sulfoxide group) that can be selectively and preferentially fragmented prior to peptide backbone cleavage during collision induced dissociation (CID)[16-18]. Such fragmentation is robust and predictable, occurring independently of cross-linking types, peptide charges, and sequences. Ultimately this unique feature enables simplified and unambiguous identification of cross-linked peptides by MS$^n$ analysis and conventional database searching tools[16-18]. In some embodiments, the inventors' sulfoxide-containing, MS-cleavable cross-linkers have been successfully applied to not only define protein-protein interactions and elucidate structures of protein complexes in vitro[5,9,16,27] and in vivo[18], but also quantify structural dynamics of protein complexes[17,19].

In current XL-MS studies, amine-reactive reagents targeting lysine residues are the most widely used compounds for successful elucidation of protein structures. This is due to their effective and specific cross-linking chemistry, as well as frequent occurrence of lysine residues in protein sequences and at surface-exposed regions of protein structures. However, it remains challenging to characterize protein interaction interfaces with little to no lysine residues.

Therefore, there is a necessity for the development of additional cross-linking chemistries in order to increase the coverage of structural information obtainable from XL-MS experiments, particularly in systems where protein interacting regions are refractive to amine-specific cross-linking. Although several types of cross-linkers targeting other amino acids (e.g. sulfhydryl-reactive and non-specific photo-reactive) reagents are commercially available, their applications in studying protein-protein interactions thus far are very limited.

For instance, sulfhydryl-reactive cross-linking reagents carrying functional groups with specific chemistries targeting cysteine residues have not been widely adopted, most likely owing to the relatively low occurrence of cysteine residues and their participation in forming disulfide bonds in protein structures. In comparison, although photochemical cross-linking reagents can improve the coverage of protein interaction contacts by reacting with any amino acids non-specifically[20], the resulting cross-linked products are often unpredictable, thus making their unambiguous MS identification even more difficult. In addition, such non-specific cross-linking has higher chance of introducing more non-specific interactions.

Therefore, a specific cross-linking chemistry targeting amino acid residues abundant at protein interaction sites would be ideal for complementing lysine targeting cross-linkers. While hydrophobic amino acid residues often constitute the cores, charged hydrophilic residues such as lysine, arginine, aspartic acid (Asp), and glutamic acid (Glu) often occupy surface-exposed regions of protein complexes, making them ideal targets for mapping protein interactions.

A recent study by Leitner et al. have demonstrated the feasibility of an acidic residue-specific cross-linking chemistry to study protein interactions using non-cleavable homobifunctional dihydrazide cross-linkers in conjunction with the coupling reagent 4-(4,6-dimethoxy-1,3,5-triazin-2-yl)-4-methylmorpholinium chloride (DMTMM)[22]. This methodology is an improvement on the acidic residue cross-linking chemistry involving the coupling reagent 1-ethyl-3-(3-dimethylaminopropyl) carbodiimide hydrochloride (EDC) that requires the cross-linking reaction to occur at a pH of 5.5[23].

In comparison, DMTMM coupling with dihydrazide cross-linkers is compatible with proteins at neutral pH (7.0-7.5) and therefore better suited for studying the structures of proteins and protein complexes under physiological conditions. However, this cross-linking strategy remains susceptible to the challenges associated with traditional cross-linking reagents in unambiguously identifying cross-linked peptides and their linkage sites. Due to the increased prevalence of Asp and Glu in protein sequences, the accurate and unambiguous identification of peptides containing non-cleavable dihydrazide cross-linked acidic residues would be intrinsically more complicated than the identification of lysine cross-linked peptides.

Due to the lack of proper reagents targeting other residues, it remains challenging to characterize protein interaction interfaces with little or no lysine residues. Similar to lysine residues, acidic residues are abundant and often present at protein contact regions.

To expand the coverage of interaction regions by XL-MS studies, in some embodiments herein, a new acidic residue reactive and sulfoxide containing MS-cleavable cross-linker, 3,3'-sulfinyldi(propanehydrazide) (DHSO) is provided. The development of DHSO cross-linker not only enlarges the range of the application of XL-MS approaches, but also further demonstrates the robustness and applicability of sulfoxide-based MS cleavability in conjunction with various reactive chemistries. In comparison to existing non-cleavable dihydrazides, DHSO contains robust MS-cleavable bonds that enable simplified and unambiguous identification of DHSO cross-linked peptides.

To simplify MS analysis and facilitate the identification of acidic residue cross-linked peptides, a sulfoxide-containing, MS-cleavable, acidic residue-specific homobifunctional cross-linking reagent, dihydrazide sulfoxide (DHSO, a.k.a. 3,3'-sulfinyldi(propanehydrazide)) has been developed as disclosed herein. This reagent adopts the same MS-labile sulfoxide chemistry as the inventors' previously developed amine-reactive, MS-cleavable cross-linkers (i.e. DSSO, DMDSSO and Azide-A-DSBSO), thus enabling robust and unambiguous identification of cross-linked peptides via the same XL-MS[n] workflow[16-18]. DHSO represents a novel class and the first generation of acidic residue-targeting cross-linking reagents with MS-cleavability.

According to a recent SwissProt database release[21]; aspartic and glutamic acids comprise roughly 12.2% of all amino acid residues, compared to the 5.8% of lysines. Therefore, acidic residues (i.e. aspartic and glutamic acids) represent high potential targets for cross-linking studies due to their abundance and prevalence at interaction interfaces. In some embodiments, the proteins and/or protein complexes targeted by DHSO comprise about 1% to about 12.5% acidic amino acid residues. In some embodiments, the proteins and/or protein complexes targeted by DHSO comprise about 0.1, 0.2, 0.3, 0.4, 0.5, 1, 2.5, 5, 7.5, 10, 12.5, 15, 17.5, 20 22.5 or 25% acidic amino acid residues, or value within a range defined by any two of the aforementioned values.

In some embodiments, DHSO expands the coverage of protein interaction regions, disclosed herein is the development of a new acidic acid residue targeting sulfoxide-containing MS-cleavable homobifunctional cross-linker, dihydrazide sulfoxide (DHSO). In some embodiments, a novel acidic residue reactive and sulfoxide-containing MS-cleavable homobifunctional cross-linker for probing protein-protein interactions is provided[28].

In some embodiments, DHSO cross-linked peptides display the same predictable and characteristic fragmentation pattern during collision induced dissociation as those amine-reactive sulfoxide-containing MS-cleavable cross-linked peptides, thus permitting their simplified analysis and unambiguous identification by MS[n]. In some embodiments, proteins are cross-linked by DHSO (3,3'-sulfinyldi(propanehydrazide)) in the presence of coupling reagent 4-(4,6-dimethoxy-1,3,5-triazin-2-yl)-4-methylmorpholinium chloride (DMTMM), forming covalent linkages between proximal and interacting proteins through aspartic acid and/or glutamic acid linkages. The resulting cross-linked peptides were analyzed by multistage tandem mass spectrometry (MS[n]). In some embodiments, other acidic amino acids besides Asp and Glu are included within the scope of this disclosure.

Additionally, in some embodiments, DHSO can provide complimentary data to amine reactive reagents. The present disclosure expands the range of the application of XL-MS approaches, but also further demonstrates the robustness and applicability of sulfoxide-based MS-cleavability in conjunction with various reactive chemistries.

In some embodiments, an integrated Xl-MS platform to determine composition-dependent conformational changes of proteins and/or protein complexes is provided. In some embodiments, it is expected that DHSO-based XL-MS strategies will become an invaluable tool in providing a complementary subset of cross-linking data towards a comprehensive structural elucidation of protein complexes by XL-MS. Design and Synthesis of a Novel Acidic Residue-Targeting Sulfoxide-Containing MS-Cleavable Cross-Linker In order to facilitate facile and accurate identification of acidic residue cross-linked peptides, it was aimed to develop a novel MS-cleavable cross-linking reagent specific to Asp and Glu residues. In some embodiments, this required the incorporation of a functional group with robust MS-inducible cleavage sites located in the spacer region of the cross-linker. Previously, we successfully developed a novel class of amine-reactive, sulfoxide-containing MS-cleavable cross-linkers, i.e., DSSO[16], DMDSSO[17] and Azide-A-DSBSO[18] (FIG. 1A-FIG. 1C). The C—S bonds adjacent to the sulfoxide group(s) in these reagents have proven to be reliable labile bonds that fragment selectively and preferentially to the breakage of peptide backbone during collision-induced dissociation. Additionally, such fragmentation is predictable and occurs independently of peptide charge and sequence. These unique features facilitate the simplified analysis of sulfoxide-containing cross-linked peptides and their unambiguous identification by $MS^n$ [16-18]. Following the success of the inventors' MS-cleavable, amine-reactive cross-linkers, a novel acidic residue-reactive, MS-cleavable homobifunctional dihydrazide cross-linker incorporating a sulfoxide group in the spacer region, i.e., 3,3'-sulfinyldi (propanehydrazide (a.k.a., dihydrazide sulfoxide (DHSO)) was designed. DHSO is synthesized from DSSO with two additional synthesis steps (FIG. 1D).

It will be understood by one of ordinary skill in the art that the parameters and conditions provided herein are exemplary and are not limiting in any way. The parameters and conditions of synthesis can be adjusted by one of ordinary skill in the art based on need and the scale of synthesis desired. In some embodiments, disuccinimidyl sulfoxide (DSSO) is synthesized as previously published[16]. The 2-step synthesis scheme for DHSO from DSSO is depicted in FIG. 1D. In some embodiments, the parameters and conditions of DHSO synthesis can be adjusted by one of ordinary skill in the art as desired. In some embodiments, tert-butyl carbazate (1.10 g, 8.32 mmol) is added to DSSO (1.41 g, 4.16 mmol) in dichloromethane (DCM) (50 mL). In some embodiments, the amount of tert-butyl carbazate ranges from about 0.22 g to about 5.5 g. In some embodiments, the amount of DSSO ranges from about 0.282 g to about 7.05 g. The resulting yellow solution is stirred at room temperature for 12 h. In some embodiments, the yellow solution is stirred at room temperature for about 2.4 h to 60 h. Thereafter, trifluoroacetic acid (2.20 mL, 28.7 mmol) is added. In some embodiments, trifluoroacetic acid volume ranges from about 0.44 mL to about 11 mL. The resulting orange solution is stirred for 72 h before removing the solvent in vacuo. In some embodiments, the orange solution is stirred at room temperature for about 14.4 h to about 360 h. The resulting orange oil is dissolved in methanol, and then triethylamine is added. The resulting mixture is stirred for 20 min, resulting in the precipitation of a white solid. In some embodiments, the mixture is stirred for about 4 min to about 100 min. The solid is collected via centrifuge, and then stirred with fresh methanol for 20 min. In some embodiments, the solid is collected by other methods know in the art such as decantation, filtration, etc. In some embodiments, the solid is stirred and washed with fresh methanol for about 4 min to about 100 min. The solid is collected via centrifuge again, and this process of stirring with fresh methanol is repeated another 2 times. In some embodiments, the process is repeated about 1 to about 20 times. The isolated white solid is dried in vacuo to obtain DHSO. In some embodiments, the white solid is dried by other methods known in the art such as drying at room temperature, heating in an oven, etc. In some embodiments, the amount of DHSO obtained is about 0.375 g. In some embodiments, the amount of DHSO obtained ranges from about 0.075 g to about 1.875 g. It will be understood by one of ordinary skill in the art that room temperature refers to a temperature of about 70° F. (or about 21° C.). In some embodiments, room temperature can be about 65° F. to about 80° F. (or about 18° C. to about 27° C.).

As shown below and in FIG. 1D, DHSO is composed of two hydrazide reactive groups separated by a 12.5 Å long spacer arm containing two symmetrical C—S cleavable bonds flanking a central sulfoxide.

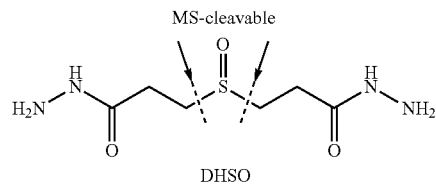

DHSO

In comparison to existing cross-linkers for XL-MS studies[16-18,22], DHSO carries a linker length well suited for defining interaction interfaces between and within protein complexes.

In some embodiments, DHSO was synthesized and characterized with synthetic peptides and simple model proteins to confirm the features of its design. In some embodiments, the MS cleavability was validated by $MS^n$ analysis. In some embodiments, the DHSO based cross-linking mass spectrometry workflow provided herein has proven to be as effective as those used for inventors' previously developed sulfoxide-containing amine reactive MS-cleavable cross-linkers, i.e. DSSO, DMDSSO and Azide-A-DSBSO. In some embodiments, the DHSO-based cross-linking mass spectrometry workflow can complement lysine reactive cross-linkers for in vitro and in vivo cross-linking studies.

In some embodiments, DHSO represents the first MS-cleavable cross-linker targeting acidic residues. DHSO comprises robust MS-cleavable bonds, i.e. C—S bonds adjacent to the center sulfoxide group, which enables fast, effective, and accurate identification of DHSO cross-linked peptides. In some embodiments, based on analysis of the standard protein BSA, many more cross-linked peptides were identified with DHSO in comparison to existing non-cleavable dihydrazide reagents. In some embodiments, DHSO cross-linked peptides possess the same characteristics distinctive to peptides cross-linked by other sulfoxide-containing amine reactive cross-linkers previously developed by the inventors.

In some embodiments, the unique features of DHSO significantly facilitate cross-linking studies targeting acidic residues, which has been difficult in the past due to the large number of D/E present in protein sequences and complexity of their resulting cross-linked peptides for MS analysis. Comparison of DHSO and DSSO confirms the need of expanding the coverage of protein interactions using cross-linkers targeting different residues, especially when the distribution of specific amino acids is uneven. Thus, in some embodiments, development of DHSO crosslinking will aid in the goal of defining protein-protein interactions at the global scale and understanding the structural dynamics of protein complexes and their mechanistic functions in cells.

In some embodiments, the DHSO-based workflow provided herein can be applied to cross-linking studies of simple and complex protein mixtures in vitro and in vivo.

CID Fragmentation Patterns of DHSO Cross-Linked Peptides

A previous study showed that the reaction of hydrazide cross-linkers with acidic residues first requires activation of the terminal carboxyl groups of Asp (D) and Glu (E) side chains or protein C-termimi[22]. The coupling reagent DMTMM was demonstrated to be effective in activating carboxylic acid groups to form a reactive intermediate that can be displaced by nucleophilic attack from hydrazides under physiological pH[22] (FIG. 2A). Therefore, in the present disclosure, DMTMM was adopted as the activating agent for DHSO cross-linking of acidic residues. Similar to lysine-reactive cross-linkers, DHSO cross-linking would result in the formation of three types of cross-linked peptides: dead-end (type 0), intra-link (type 1), and inter-link (type 2) modified peptides, among which inter-linked peptides provide the most informative data on the relative spatial orientation of cross-linked acidic residues[26].

Since all of the MS-cleavable, homobifunctional NHS esters we previously developed display the same characteristic fragmentation patterns in $MS^2$ due to the cleavage of either of the two symmetric CID-cleavable C—S bonds adjacent to the sulfoxide functional group[16-18], it is expected that DHSO cross-linked peptides will behave similarly during $MS^n$ analysis even though their residue-targeting functional groups are different.

To elaborate this process, FIG. 2B-FIG. 2D illustrates the predicted $MS^2$ fragmentation patterns of DHSO cross-linked peptides. For a DHSO inter-linked peptide α-β, the cleavage of one of the two symmetric C—S bonds would result in one of the two predicted peptide fragment pairs (i.e. $\alpha_A/\beta_S$ or $\alpha_S/\beta_A$) (FIG. 2B). The resulting α and β peptide fragments are modified by complementary cross-linker remnant moieties, i.e., alkene (A) or sulfenic acid (S). Therefore, a total of four individual $MS^2$ fragment ion peaks are expected for a DHSO cross-linked heterodimer, representing the two predictable pairs of peptide fragments. These single peptide chains are then be subjected to $MS^3$ analysis, permitting unambiguous identification of each cross-linked peptide sequence and cross-linking site respectively. For a DHSO intra-linked peptide αintra in which proximal D or E amino acid residues are cross-linked within the same peptide, one peptide fragment (i.e. $\alpha_{A+S}$) is expected in $MS^2$ analysis (FIG. 2C). In reality, this particular ion would represent two populations of ion species that have identical peptide sequences and m/z values, but transposed DHSO remnant-modified acidic residues. Lastly, a DHSO dead-end modified peptide αDN would potentially fragment into two ion species during $MS^2$ analysis. Depending on the position of the cleaved C—S bond, $\alpha_A$ or $\alpha_S$ fragments would be observed, resulting in a pair of daughter ions detected during $MS^2$ (FIG. 2D). In all three scenarios, it is noted that the sulfenic acid moiety often undergo dehydration to become a more stable and dominant unsaturated thiol moiety (i.e. T) (FIG. 2E), a conversion that is commonly observed in amine reactive, sulfoxide containing MS-cleavable cross-linked peptides and that does not complicate data analysis as previously demonstrated[16-18]. Of note, S* (sulfenic acid moiety) can be converted to the more stable unsaturated thiol moiety (T) via water loss (FIG. 2E). The distinct $MS^2$ fragmentation patterns of sulfoxide-containing MS-cleavable cross-linked peptides result in predictable mass relationships between parent ions and their respective fragments. These mass relationships are utilized as an additional verification of cross-linked peptide identification at the $MS^2$ level. Along with mass fingerprinting by $MS^1$ and peptide sequencing by $MS^3$, three lines of evidence can be obtained and integrated to accurately identify DHSO cross-linked peptides using the identical $MS^n$ workflow previously developed for the analysis of DSSO, DMDSSO and DSBSO cross-linked peptides[16-18].

Characterization of DHSO Cross-Linked Model Peptides by $MS^n$ Analysis

Despite the similarities in spacer arm structure to DSSO, it is necessary to verify whether DHSO cross-linked peptides indeed fragment the same way as described above during $MS^n$ analysis (FIG. 2). Initial characterization of DHSO was performed on a synthetic peptide containing a single acidic residue, Ac-SR8 (Ac-SAKAYEHR (SEQ ID NO: 178)). As a result, inter-linked Ac-SR8 dimer was detected as quadruply-charged (m/z 548.7623$^{4+}$) and quintuply-charged (m/z 439.2117$^{5+}$) ion species, respectively. $MS^2$ analysis of the quadruply-charged parent ion produced a pair of dominant fragment ions αA/αT (m/z 536.272+/552.26$^{2+}$), demonstrating effective physical separation of the two cross-linked peptides as expected (FIG. 3A). Similarly, $MS^2$ analysis of the quintuply-charged parent ion (m/z 439.2117$^{5+}$) yielded a single pair of dominant fragment ions αA/αT (m/z 357.85$^{3+}$1552.26$^{2+}$) as well (FIG. 3B), demonstrating the characteristic fragmentation independent of peptide charges as expected. Subsequent $MS^3$ analyses of the $\alpha_A$ (m/z 536.27$^{2+}$) fragment ion (FIG. 3C) resulted in series of y and b ions that unambiguously confirmed the peptide sequence as Ac-SAKAYEAHR (SEQ ID NO: 179) in which the glutamic acid was modified with a DHSO alkene (A) moiety. Similarly, $MS^3$ spectrum of the $\alpha_T$ fragment (m/z 552.26$^{2+}$) determined its identity as Ac-SAKAYETHR (SEQ ID NO: 180), in which the glutamic acid was modified with a DHSO unsaturated thiol (T) moiety (FIG. 3D). Therefore, the cross-linked peptide was identified as [Ac-SAKAYE$^6$HR] (SEQ ID NO: 181) inter-linked to [Ac-SAKAYE$^6$HR] (SEQ ID NO: 181) through E6 in both peptides. This result indicates that DHSO inter-linked peptides indeed display the same characteristic $MS^n$ fragmentation as sulfoxide-containing lysine inter-linked peptides, and can be analyzed using the same data analysis workflow as previously described[16-18].

Characterization of DHSO Cross-Linked Model Proteins by $MS^n$ Analysis

To evaluate the capability of DHSO for protein cross-linking in vitro, equine myoglobin and bovine serum albumin (BSA) were used as model proteins. These two proteins contain above-average acidic residue content (16.3% and 13.6%, respectively), making them well suited for evaluating DHSO cross-linking. In addition, BSA was employed previously for acidic residue cross-linking by non-cleavable dihydrazides[22]. To identify DHSO cross-linked peptides in myoglobin and BSA, in-gel digestion of gel-separated DHSO cross-linked proteins or in solution digestion of DHSO cross-linked proteins followed by peptide SEC was performed as illustrated (FIG. 7A-FIG. 7D). Of note, S* (sulfenic acid moiety) can be converted to the more stable unsaturated thiol moiety (T) via water loss as shown in FIG. 7D. The resulting peptides were subjected to LC-$MS^n$ analysis. FIG. 4A displays the $MS^1$ spectra for an exemplary inter-link (α-β) (m/z 517.2703$^{4+}$) identified from equine myoglobin. Its $MS^2$ analysis resulted in the detection of the two characteristic peptide fragment pairs $\alpha_A/\beta_T$ (m/z 429.742+/569.63$^{2+}$) and $\alpha_T/\beta_A$ (m/z 445.72$^{2+}$/559.64$^{2+}$) (FIG. 4B). $MS^3$ analysis of $\alpha_A$ (m/z 429.74$^{2+}$) (FIG. 4C) determined its sequence as ASE$_A$DLKK (SEQ ID NO: 182), in which the glutamic acid residue at the 3rd position from the N-terminus was modified with an alkene moiety. $MS^3$ analysis of $\beta_T$ (m/z 569.63$^{2+}$) identified its sequence as VEAD$_T$IAGHGQEVLIR (SEQ ID NO: 183), with the aspartic acid residue at the 4th position from the N-terminus carrying an unsaturated thiol moiety (FIG. 4D). Together with $MS^1$ and $MS^2$ data, the inter-linked peptides were unambiguously identified as [$^{18}$VEAD$_T$IAGHGQEVLIR$^{32}$ (SEQ ID NO: 183) cross-linked to $^{58}$ASE$_A$DLKK$^{64}$] (SEQ ID NO: 182), describing an inter-link formed between D21 and E60 of equine myoglobin.

FIG. 9A-FIG. 9D display $MS^n$ analysis of a selected DHSO inter-linked BSA peptide, which was measured as a quadruply-charged ion (m/z 692.8475$^{4+}$) in $MS^1$ (FIG. 9A). Its $MS^2$ spectrum revealed two pairs of complementary $MS^2$ fragment ions $\alpha_A/\beta_T$ (m/z 616.32$^{2+}$/760.36$^{2+}$) and $\alpha_T/\beta_A$ (m/z 632.32$^{2+}$/744.37$^{2+}$), further demonstrating the robust fragmentation expected of DHSO cross-linked peptides (FIG. 9B). Together with $MS^3$ sequencing of $MS^2$ fragments $\alpha A$ (m/z 616.32$^{2+}$) and $\beta T$ (m/z 760.36$^{2+}$) (FIG. 9C and FIG. 9D), this DHSO inter-linked peptide was unambiguously identified as [$^{66}$LVNE$_A$LTEFAK$^{75}$ (SEQ ID NO: 184) inter-linked to $^{89}$SLHTLFGDE$_T$LCK$^{100}$] (SEQ ID NO: 185), in which residue E69 cross-linked to residue E97 in BSA.

In addition to inter-linked peptides, intra-linked peptides were also observed as a result of DHSO cross-linking in the model proteins. For example, $MS^2$ fragmentation of an intra-linked myoglobin peptide (FIG. 10A-FIG. 10C) produced a single fragment ion peak $\alpha_{A+T}$ (m/z 514.02$^{4+}$) with 18 Da less than the parent ion, consistent with the expected fragmentation pattern described in FIG. 2B following dehydration of the sulfenic acid moiety to an unsaturated thiol moiety. Analysis of the $\alpha_{A+T}$ ion in subsequent $MS^3$ analysis (FIG. 10C) yielded series of b and y ions permitting the unambiguous identification of two peptides sharing identical sequences but transposed alkene and unsaturated thiol moieties: $^{105}$YLE$_A$FISD$_T$AIIHVLHSK119 (SEQ ID NO: 186) and $^{05}$YLE$_T$FISD$_A$AIIHVLHSK$^{119}$ (SEQ ID NO: 187), indicating an intra-link between residues E106 and D110.

Moreover, $MS^2$ fragmentation of a myoglobin dead-end modified peptide (m/z 604.3095$^{3+}$) resulted in the detection of a single pair of fragment ions $\alpha A/\alpha T$ (m/z 559.30$^{3+}$/569.96$^{3+}$), consistent with the expected fragmentation pattern described in FIG. 2C (FIG. 11C). These fragment ions were then identified in subsequent $MS^3$ analysis as $^{18}$VE$_A$ADIAGHGQEVLIR32 (SEQ ID NO: 188) and $^{18}$VE$_T$ADIAGHGQEVLIR32 (SEQ ID NO: 189), representing a dead-end cross-link located on E19 of myoglobin (FIG. 4C and FIG. 4D). These results further demonstrate the robust $MS^n$ analysis of DHSO cross-linked peptides.

In total, LC-$MS^n$ analysis of DHSO cross-linked myoglobin identified a total of 33 unique inter-linked peptides, representing 32 unique E|D-E|D linkages (Table 1).

TABLE 1

Summary of DHSO Inter-Linked Myoglobin Peptides Identified by LC $MS^n$

| # | Peptide Seq | AA location | MS m/z | z | Δ (PPM) | Mod. Position | MS2 m/z | z | Distance (Cα-Cα) |
|---|---|---|---|---|---|---|---|---|---|
| 1 | ALELFR (SEQ ID NO: 1) | A135-R140 | 421.2357 | 4 | 0.186 | $E_T$137 | 424.726 | 2 | — |
|   | ALELFR (SEQ ID NO: 2) | A135-R140 |  |  |  | $E_A$137 | 408.740 | 2 |  |
| 2 | HPGDFGADAQGAM(ox)TK (SEQ ID NO: 3) \| (SEQ ID NO: 4) | H120-K134 | 613.7913 | 4 | -2.547 | $D_A$123\|$D_A$127 | 793.885 | 2 | 21.6Å\|15.4Å |
|   | ALELFR (SEQ ID NO: 2) | A135-R140 |  |  |  | $E_A$137 | 408.740 | 2 |  |
| 3 | HPGDFGADAQGAMTK (SEQ ID NO: 5) | H120-K134 | 609.7944 | 4 | .435 | $D_A$127 | 785.859 | 2 | 15.4Å |
|   | ALELFR (SEQ ID NO: 2) | A135-R140 |  |  |  | $E_A$137 | 408.741 | 2 |  |
| 4 | KKGHHEAELKPLAQSHATK (SEQ ID NO: 9) \| (SEQ ID NO: 10) | K79-K97 | 737.1354 | 4 | 1.188 | $E_A$84\|$E_A$86 | 726.736 | 3 | 14.1Å\|16.8Å |
|   | ELGFQG (SEQ ID NO: 14) | E149-G154 |  |  |  | $E_A$149 | 718.335 | 1 |  |
| 5 | LFTGHPETLEK (SEQ ID NO: 15) | L33-K43 | 441.8353 | 5 | -0.494 | $E_T$42 | 457.895 | 3 | 24.4Å |
|   | ALELFR (SEQ ID NO: 2) | A135-R140 |  |  |  | $E_A$137 | 408.740 | 2 |  |
| 6 | LFTGHPETLEK (SEQ ID NO: 16) \| (SEQ ID NO: 17) | L33-K43 | 441.8364 | 5 | 1.996 | $E_A$39\|$E_A$42 | 447.239 | 3 | 22.0Å\|24.4Å |
|   | ALELFR (SEQ ID NO: 2) | A135-R140 |  |  |  | $E_A$137 | 408.740 | 2 |  |
| 7 | LFTGHPETLEK (SEQ ID NO: 18) \| (SEQ ID NO: 15) | L33-K43 | 437.0133 | 5 | 2.713 | $E_T$39\|$E_T$42 | 437.895 | 3 | 14.6 Å\|14.7Å |
|   | TEAEM(ox)K (SEQ ID NO: 19) | T52-K57 |  |  |  | $E_A$53 | 396.682 | 2 |  |

TABLE 1-continued

Summary of DHSO Inter-Linked
Myoglobin Peptides Identified by LC MS$^n$

| # | Peptide Seq | AA location | MS m/z | z | Δ (PPM) | Mod. Position | MS2 m/z | z | Distance (Cα-Cα) |
|---|---|---|---|---|---|---|---|---|---|
| 8 | LFTGHPETLEK (SEQ ID NO: 15) | L33-K43 | 542.0137 | 4 | -1.652 | $E_T42$ | 686.342 | 2 | 14.7Å\|15.4Å |
|   | TEAEMK (SEQ ID NO: 21)\|(SEQ ID NO: 22) | T52-K57 |   |   |   | $E_A53$\|$E_A55$ | 388.685 | 2 |   |
| 9 | LFTGHPETLEK (SEQ ID NO: 18) | L33-K43 | 546.2628 | 4 | -3.499 | $E_T39$ | 686.341 | 2 | 14.6Å |
|   | TEAEM(ox)K (SEQ ID NO: 19) | T52-K57 |   |   |   | $E_A53$ | 396.682 | 2 |   |
| 10 | LFTGHPETLEK (SEQ ID NO: 15) | L33-K43 | 546.0119 | 4 | -2.068 | $E_T42$ | 686.341 | 2 | 14.7Å |
|   | TEAEM(ox)K (SEQ ID NO: 19) | T52-K57 |   |   |   | $E_A53$ | 396.682 | 2 |   |
| 11 | LFTGHPETLEK (SEQ ID NO: 15) | L33-K43 | 433.8133 | 5 | 0.389 | $E_T42$ | 457.896 | 3 | 15.4Å |
|   | TEAEMK (SEQ ID NO: 22) | T52-K57 |   |   |   | $E_A55$ | 388.685 | 2 |   |
| 12 | LFTGHPETLEK (SEQ ID NO: 18)\|(SEQ ID NO: 15) | L33-K43 | 546.4794 | 5 | -3.081 | $E_T39$\|$E_T42$ | 686.340 | 2 | — |
|   | LFTGHPETLEK (SEQ ID NO: 16)\|(SEQ ID NO: 17) | L33-K43 |   |   |   | $E_A39$\|$E_A42$ | 447.238 | 3 |   |
| 13 | LFTGHPETLEK (SEQ ID NO: 16)\|(SEQ ID NO: 17) | L33-K43 | 683.1003 | 4 | -0.109 | $E_A39$\|$E_A42$ | 670.355 | 2 | — |
|   | LFTGHPETLEK (SEQ ID NO: 15) | L33-K43 |   |   |   | $E_T42$ | 686.339 | 2 |   |
| 14 | LFTGHPETLEK (SEQ ID NO: 17) | L33-K43 | 682.8481 | 4 | -2.906 | $E_A42$ | 670.354 | 2 | — |
|   | LFTGHPETLEK (SEQ ID NO: 15) | L33-K43 |   |   |   | $E_T42$ | 686.340 | 2 |   |
| 15 | LFTGHPETLEK (SEQ ID NO: 16) | L33-K43 | 683.3470 | 4 | -6.165 | $E_A39$ | 670.355 | 2 | — |
|   | LFTGHPETLEK (SEQ ID NO: 15) | L33-K43 |   |   |   | $E_T42$ | 686.339 | 2 |   |
| 16 | TEAEM(ox)K (SEQ ID NO: 9) | T52-K57 | 415.2066 | 4 | 0.561 | $E_A53$ | 396.681 | 2 | 28.0Å |
|   | ALELFR (SEQ ID NO: 1) | A135-R140 |   |   |   | $E_T137$ | 424.725 | 2 |   |
| 17 | TEAEMK (SEQ ID NO: 21) | T52-K57 | 401.1799 | 4 | 0.611 | $E_A53$ | 388.684 | 2 | — |
|   | TEAEMK (SEQ ID NO: 23) | T52-K57 |   |   |   | $E_T53$ | 404.67 | 2 |   |
| 18 | TEAEMK (SEQ ID NO: 21)\|(SEQ ID NO: 22) | T52-K57 | 421.7067 | 4 | 1.031 | $E_A53$\|$E_A55$ | 388.684 | 2 | 13.0Å\|9.8Å 14.0Å\|11.0Å |
|   | ASEDLK (SEQ ID NO: 24)\|(SEQ ID NO: 25) | A58-K63 |   |   |   | $E_T60$\|$D_T61$ | 445.722 | 2 |   |
| 19 | TEAEMK (SEQ ID NO: 21) | T52-K57 | 421.7063 | 4 | -0.392 | $E_A53$ | 388.684 | 2 | 13.0Å\|9.8Å |
|   | ASEDLKK (SEQ ID NO: 24)\|(SEQ ID NO: 25) | A58-K64 |   |   |   | $E_T60$\|$D_T61$ | 445.724 | 2 |   |
| 20 | TEAEMK (SEQ ID NO: 21) | T52-K57 | 599.7642 | 4 | -3.253 | $E_A53$ | 388.684 | 2 | 32.1Å |
|   | HPGDFGADAQGAMTK (SEQ ID NO: 6) | H120-K134 |   |   |   | $D_T127$ | 801.844 | 2 |   |

TABLE 1-continued

Summary of DHSO Inter-Linked
Myoglobin Peptides Identified by LC MS$^n$

| # | Peptide Seq | AA location | MS m/z | z | Δ (PPM) | Mod. Position | MS2 m/z | z | Distance (Cα-Cα) |
|---|---|---|---|---|---|---|---|---|---|
| 21 | VEADIAGHGQEVLIR (SEQ ID NO: 27) | V18-R32 | 500.8524 | 5 | 18.47 | $E_T28$ | 569.627 | 3 | 10.5Å |
|    | TEAEMK (SEQ ID NO: 21) | T52-K57 |  |  |  | $E_A53$ | 388.685 | 2 |  |
| 22 | VEADIAGHGQEVLIR (SEQ ID NO: 27) | V18-R32 | 629.8124 | 4 | 0.950 | $E_T28$ | 853.939 | 2 | 10.5Å\|13.0Å |
|    | TEAEM(ox)K (SEQ ID NO: 19) \| (SEQ ID NO: 20) | T52-K57 |  |  |  | $E_A53$\|$E_A55$ | 396.681 | 2 |  |
| 23 | VEADIAGHGQEVLIR (SEQ ID NO: 28) \| (SEQ ID NO: 29) | V18-R32 | 614.5657 | 4 | -2.085 | $E_A19$\|$D_A21$ | 558.970 | 3 | 18.4Å\|14.7Å |
|    | ASEDLK (SEQ ID NO: 26) | A58-K63 |  |  |  | $E_A60$ | 730.374 | 1 |  |
| 24 | VEADIAGHGQEVLIR (SEQ ID NO: 28) \| (SEQ ID NO: 29) | V18-R32 | 614.3143 | 4 | -2.107 | $E_A19$\|$D_A21$ | 558.969 | 3 | 18.4Å\|18.8Å 14.7Å\|16.1Å |
|    | ASEDLK (SEQ ID NO: 24) \| (SEQ ID NO: 25) | A58-K62 |  |  |  | $E_T60$\|$D_T61$ | 730.374 | 1 |  |
| 25 | VEADIAGHGQEVLIR (SEQ ID NO: 30) | V18-R32 | 517.2736 | 5 | 1.308 | $D_T21$ | 569.627 | 3 | 14.7Å\|16.1Å |
|    | ASEDLKK (SEQ ID NO: 24) \| (SEQ ID NO: 25) | A58-K63 |  |  |  | $E_T60$\|$D_T61$ | 445.725 | 2 |  |
| 26 | VEADIAGHGQEVLIR (SEQ ID NO: 30) | V18-R32 | 517.2736 | 5 | 1.308 | $D_T21$ | 569.627 | 3 | 14.7Å |
|    | ASEDLKK (SEQ ID NO: 26) | A58-K64 |  |  |  | $E_A60$ | 429.738 | 2 |  |
| 27 | VEADIAGHGQEVLIR (SEQ ID NO: 30) | V18-R32 | 659.7219 | 5 | 1.861 | $D_T21$ | 569.627 | 3 | 15.7Å |
|    | HPGDFGADAQGAMTK (SEQ ID NO: 7) | H120-K134 |  |  |  | $D_A123$ | 785.858 | 2 |  |
| 28 | VEADIAGHGQEVLIR (SEQ ID NO: 30) | V18-R32 | 659.7219 | 5 | 1.861 | $D_T21$ | 569.627 | 3 | 15.7Å\|22.3Å |
|    | HPGDFGADAQGAMTK (SEQ ID NO: 8) \| (SEQ ID NO: 6) | H120-K134 |  |  |  | $D_T123$\|$D_T127$ | 801.847 | 2 |  |
| 29 | VEADIAGHGQEVLIR (SEQ ID NO: 28) | V19-R32 | 659.7193 | 5 | -2.080 | $E_A19$ | 558.969 | 3 | 19.8Å |
|    | HPGDFGADAQGAMTK (SEQ ID NO: 6) | H120-K134 |  |  |  | $D_T127$ | 801.843 | 2 |  |
| 30 | VEADIAGHGQEVLIR (SEQ ID NO: 30) \| (SEQ ID NO: 27) | V18-R32 | 504.0492 | 5 | -2.495 | $D_T21$\|$E_T28$ | 569.627 | 3 | 20.1Å\|10.5Å |
|    | TEAEM(ox)K (SEQ ID NO: 19) | T52-K57 |  |  |  | $E_A53$ | 396.681 | 2 |  |
| 31 | YLEFISDAIIHVLHSK (SEQ ID NO: 31) | Y104-K119 | 564.5054 | 5 | -3.321 | $D_T110$ | 662.346 | 3 | 10.1Å |
|    | ALELFR (SEQ ID NO: 2) | A135-R140 |  |  |  | $E_A137$ | 408.739 | 2 |  |
| 32 | YLEFISDAIIHVLHSK (SEQ ID NO: 32) | Y104-K119 | 705.3836 | 4 | 1.880 | $E_A106$ | 651.691 | 3 | 8.4Å |
|    | ALELFR (SEQ ID NO: 2) | A135-R140 |  |  |  | $E_A137$ | 816.475 | 1 |  |

TABLE 1-continued

Summary of DHSO Inter-Linked
Myoglobin Peptides Identified by LC MS"

| # | Peptide Seq | AA location | MS m/z | z | Δ (PPM) | Mod. Position | MS2 m/z | z | Distance (Cα-Cα) |
|---|---|---|---|---|---|---|---|---|---|
| 33 | YLEFISDAIIHVLHSK (SEQ ID NO: 33) \| (SEQ ID NO: 31) ALELFR (SEQ ID NO: 2) | Y104-K119<br>A135-R140 | 564.5085 | 5 | 2.171 | $E_T106$\|$D_T110$<br>$E_A137$ | 662.350<br>408.741 | 3<br>2 | 8.4Å\|10.1Å |

Note:
"|" means or; "&" means and; "T": unsaturated thiol moiety; "A": alkene moiety; "ox" means oxidation.

Similarly, 62 unique DHSO inter-linked BSA peptides were identified, describing 69 unique E|D-E|D linkages (Table 2).

TABLE 2

Summary of DHSO Inter-Linked
BSA Peptides Identified by LC MS"

| # | Peptide Seq | AA location | MS m/z | z | Δ (PPM) | Mod. Position | MS2 m/z | z | Distance (Cα-Cα) |
|---|---|---|---|---|---|---|---|---|---|
| 1 | AEFVEVTK (SEQ ID NO: 34) LVTDLTK (SEQ ID NO: 37) | A249-K256<br>L257-K263 | 475.0076 | 4 | -0.713 | $E_A250$<br>$D_A260$ | 495.765<br>429.257 | 2<br>2 | 16.1Å |
| 2 | AEFVEVTK (SEQ ID NO: 35) LVTDLTK (SEQ ID NO: 37) | A249-K256<br>L257-K263 | 475.0078 | 4 | -0.292 | $E_T253$<br>$D_A260$ | 511.752<br>429.257 | 2<br>2 | 10.9Å |
| 3 | AEFVEVTK (SEQ ID NO: 34) QNCDQFEK (SEQ ID NO: 39) | A249-K256<br>Q413-K420 | 544.7503 | 4 | -0.181 | $E_A250$<br>$E_T419$ | 495.768<br>584.731 | 2<br>2 | 45.1Å |
| 4 | AEFVEVTK (SEQ ID NO: 34) \| (SEQ ID NO: 36) YICDNQDTISSK (SEQ ID NO: 43) | A249-K256<br>Y286-K297 | 638.5493 | 4 | -1.936 | $E_A250$\|$E_A253$<br>$D_T292$ | 495.767<br>772.330 | 2<br>2 | 11.5Å\|11.6Å |
| 5 | AEFVEVTK (SEQ ID NO: 34) YICDNQDTISSK (SEQ ID NO: 43) | A249-K256<br>Y286-K297 | 638.5493 | 4 | -1.936 | $E_A250$<br>$D_T292$ | 495.767<br>772.330 | 2<br>2 | 11.5Å |
| 6 | AEFVEVTK (SEQ ID NO: 36) YICDNQDTISSK (SEQ ID NO: 44) \| (SEQ ID NO: 43) | A249-K256<br>Y286-K297 | 638.5522 | 4 | 2.606 | $E_A253$<br>$D_T289$\|$D_T292$ | 495.767<br>772.331 | 2<br>2 | 12.8Å\|11.6Å |
| 7 | ATEEQLK (SEQ ID NO: 46) \| (SEQ ID NO: 47) TVM(ox)ENFVAFVDK (SEQ ID NO: 48) | A562-K568<br>T569-K580 | 601.5462 | 4 | -0.098 | $E_A564$\|$E_A565$<br>$E_T572$ | 443.735<br>750.354 | 2<br>2 | 12.4Å\|11.0Å |
| 8 | ATEEQLK (SEQ ID NO: 47) TVMENFVAFVDK (SEQ ID NO: 49) | A562-K568<br>T569-K580 | 601.5485 | 4 | 1.611 | $E_A565$<br>$E_T572$ | 443.735<br>750.356 | 2<br>2 | 11.0Å |
| 9 | DTHKSEIAHR (SEQ ID NO: 50) VHKECCHGDLLECADDRADLAK (SEQ ID NO: 54) \| (SEQ ID NO: 55) \| (SEQ ID NO: 56) | D25-R34<br>V264-K285 | 499.8580 | 8 | -1.939 | $D_T25$<br>$D_A278$\|$D_A279$\|$D_A282$ | 431.877<br>536.846 | 3<br>5 | 21.2Å\|20.9Å\|21.7Å |

TABLE 2-continued

Summary of DHSO Inter-Linked
BSA Peptides Identified by LC MS"

| # | Peptide Seq | AA location | MS m/z | z | Δ (PPM) | Mod. Position | MS2 m/z | z | Distance (Cα-Cα) |
|---|---|---|---|---|---|---|---|---|---|
| 10 | DTHKSEIAHR (SEQ ID NO: 50) | D25-R34 | 570.9825 | 7 | 4.106 | $D_T25$ | 431.877 | 3 | 21.2Å\|21.7Å |
|  | VHKECCHGDLLECADD RADLAK (SEQ ID NO: 55)\| (SEQ ID NO: 56) | V264-K285 |  |  |  | $D_A279\|D_A282$ | 670.808 | 4 |  |
| 11 | DTHKSEIAHR (SEQ ID NO: 50)\| (SEQ ID NO: 51) | D25-R34 | 499.7346 | 8 | 2.110 | $D_T25\|E_T30$ | 431.876 | 3 | 21.2Å\|20.9Å\| 21.7Å, 12.0Å\| 13.9Å\|16.7Å |
|  | VHKECCHGDLLECADD RADLAK (SEQ ID NO: 54)\| (SEQ ID NO: 55)\| (SEQ ID NO: 56) | V264-K285 |  |  |  | $D_A278\|D_A279\| D_A282$ | 536.847 | 5 |  |
| 12 | DTHKSEIAHR (SEQ ID NO: 50)\| (SEQ ID NO: 51) | D25-R34 | 570.9843 | 8 | -0.169 | $D_T25\|E_T30$ | 6431.876 | 3 | 21.2Å\|21.7Å, 12.0Å\|16.7Å |
|  | VHKECCHGDLLECADD RADLAK (SEQ ID NO: 54)\| (SEQ ID NO: 56) | V264-K285 |  |  |  | $D_A278\|D_A282$ | 536.847 | 5 |  |
| 13 | DTHKSEIAHR (SEQ ID NO: 51) | D25-R34 | 570.9797 | 7 | -0.798 | $E_T30$ | 647.311 | 2 | 12.0Å\|13.9Å\| 16.7Å |
|  | VHKECCHGDLLECADD RADLAK (SEQ ID NO: 54)\| (SEQ ID NO: 55)\| (SEQ ID NO: 56) | V264-K285 |  |  |  | $D_A278\|D_A279\| D_A282$ | 536.848 | 5 |  |
| 14 | DTHKSEIAHR (SEQ ID NO: 52) | D25-R34 | 542.7869 | 4 | 0.787 | $D_A25$ | 631.324 | 2 | 22.7Å |
|  | LVTDLTK (SEQ ID NO: 37) | L257-K263 |  |  |  | $D_A260$ | 429.259 | 2 |  |
| 15 | DTHKSEIAHR (SEQ ID NO: 50) | D25-R34 | 711.5669 | 4 | 0.368 | $D_T25$ | 647.310 | 2 | 18.8Å\|15.4Å |
|  | TCVADESHAGCEK (SEQ ID NO: 59)\| (SEQ ID NO: 60) | T76-K88 |  |  |  | $D_A80\|E_A81$ | 766.318 | 2 |  |
| 16 | DTHKSEIAHR (SEQ ID NO: 50) | D25-R34 | 711.3146 | 4 | -1.686 | $D_T25$ | 647.311 | 2 | 14.6Å |
|  | TCVADESHAGCEK (SEQ ID NO: 61) | T76-K88 |  |  |  | $E_A87$ | 766.316 | 2 |  |
| 17 | DLGEEHFK (SEQ ID NO: 62) | D37-K44 | 438.2119 | 4 | 1.889 | $E_T41$ | 537.738 | 2 | 16.3Å\|13.0Å |
|  | ADEKK (SEQ ID NO: 63) | A152-K156 |  |  |  | $E_A154$ | 329.680 | 2 |  |
| 18 | GLVLIAFSQYLQQCPF DEHVK (SEQ ID NO: 64)\| (SEQ ID NO: 190) | G45-K65 | 902.9565 | 4 | -1.045 | $D_A61\|E_A62$ | 1280.660 | 2 | 12.4Å\|13.7Å |
|  | YLYEIAR (SEQ ID NO: 65) | Y161-R167 |  |  |  | $E_T164$ | 514.256 | 2 |  |
| 19 | HLVDEPQNLIK (SEQ ID NO: 67) | H402-K412 | 665.0706 | 4 | .496 | $D_T405$ | 703.368 | 2 | 13.6Å |
|  | CCTKPESER (SEQ ID NO: 70) | C460-R468 |  |  |  | $E_A465$ | 617.770 | 2 |  |
| 20 | HLVDEPQNLIK (SEQ ID NO: 68)\| (SEQ ID NO: 69) | H402-K412 | 665.0706 | 4 | .496 | $D_A405\|E_A406$ | 687.382 | 2 | 13.6Å\|15.8Å |
|  | CCTKPESER (SEQ ID NO: 70) | C460-R468 |  |  |  | $E_A465$ | 617.770 | 2 |  |

TABLE 2-continued

Summary of DHSO Inter-Linked
BSA Peptides Identified by LC MS"

| # | Peptide Seq | AA location | MS m/z | z | Δ (PPM) | Mod. Position | MS2 m/z | z | Distance (Cα-Cα) |
|---|---|---|---|---|---|---|---|---|---|
| 21 | HLVDEPQNLIK (SEQ ID NO: 67) | H402-K412 | 532.4614 | 5 | 5.743 | $D_T405$ | 703.367 | 2 | 13.6Å\|13.1Å |
| | CCTKPESER (SEQ ID NO: 70)\|(SEQ ID NO: 71) | C460-R468 | | | | $E_A465\|E_A467$ | 412.182 | 3 | |
| 22 | IETMR (SEQ ID NO: 75) | I205-R210 | 579.3010 | 4 | 1.167 | $E_A206$ | 359.19 | 2 | 17.8Å |
| | LGEYGFQNALIVR (SEQ ID NO: 76) | L421-R433 | | | | $E_T423$ | 790.405 | 2 | |
| 23 | IETMR (SEQ ID NO: 75) | I205-R210 | 587.3107 | 4 | -2.486 | $E_A206$ | 359.19 | 2 | 18.8Å |
| | VPQVSTPTLVEVSR (SEQ ID NO: 78) | V438-R451 | | | | $E_T448$ | 806.428 | 2 | |
| 24 | LKPDPNTLCDEFK (SEQ ID NO: 79) | L139-K151 | 673.0840 | 4 | 1.077 | $E_T149$ | 838.893 | 2 | 14.9Å |
| | YLYEIAR (SEQ ID NO: 66) | Y161-R167 | | | | $E_A164$ | 498.269 | 2 | |
| 25 | LKPDPNTLCDEFKADEK (SEQ ID NO: 81)\|(SEQ ID NO: 82) | L139-K155 | 627.5087 | 5 | -0.588 | $D_T153\|E_T154$ | 707.332 | 3 | 16.7Å\|15.6Å |
| | YLYEIAR (SEQ ID NO: 66) | Y161-R167 | | | | $E_A164$ | 498.269 | 2 | |
| 26 | LVTDLTK (SEQ ID NO: 37) | L257-K263 | 897.4279 | 4 | 0.795 | $D_A260$ | 857.511 | 1 | 9.1Å |
| | VHKECCHGDLLECADDRADLAK (SEQ ID NO: 57) | V264-K285 | | | | $D_A282$ | 894.072 | 3 | |
| 27 | LVTDLTK (SEQ ID NO: 38) | L257-K263 | 513.2476 | 7 | 0.730 | $D_T260$ | 445.245 | 2 | 7.8Å, 9.1Å |
| | VHKECCHGDLLECADDRADLAK (SEQ ID NO: 55)\|(SEQ ID NO: 56) | V264-K285 | | | | $D_A279\|D_A282$ | 536.848 | 5 | |
| 28 | LVTDLTK (SEQ ID NO: 38) | L257-K263 | 513.2481 | 7 | 1.704 | $D_T260$ | 445.245 | 2 | 11.6Å, 7.8Å, 9.1Å |
| | VHKECCHGDLLECADDRADLAK (SEQ ID NO: 54)\|(SEQ ID NO: 55)\|(SEQ ID NO: 56) | V264-K285 | | | | $D_A278\|D_A279\|D_A282$ | 536.848 | 5 | |
| 29 | LVTDLTK (SEQ ID NO: 37) | L257-K263 | 605.4583 | 4 | 1.684 | $D_A260$ | 429.259 | 2 | 18.9Å |
| | YICDNQDTISSK (SEQ ID NO: 45) | Y286-K297 | | | | $D_A292$ | 772.330 | 2 | |
| 30 | LKECCDKPLLEK (SEQ ID NO: 83)\|(SEQ ID NO: 84) | L298-K309 | 558.8729 | 5 | -1.841 | $E_A300\|D_A303$ | 534.278 | 3 | 11.2Å\|15.8Å |
| | SHCIAEVEK (SEQ ID NO: 88) | S310-K318 | | | | $E_T317$ | 586.764 | 2 | |
| 31 | LKECCDKPLLEK (SEQ ID NO: 83) | L298-K309 | 465.8965 | 6 | 0.744 | $E_A300$ | 400.961 | 4 | 11.2Å |
| | SHCIAEVEK (SEQ ID NO: 88) | S310-K318 | | | | $E_T317$ | 586.764 | 2 | |
| 32 | LKECCDKPLLEK (SEQ ID NO: 85) | L298-K309 | 698.3413 | 4 | 1.014 | $E_T300$ | 816.901 | 2 | 11.9Å |
| | SHCIAEVEK (SEQ ID NO: 89) | S310-K318 | | | | $E_A315$ | 570.778 | 2 | |
| 33 | LKECCDKPLLEK (SEQ ID NO: 83) | L298-K309 | 698.3408 | 4 | 0.298 | $E_A300$ | 800.915 | 2 | 11.9Å\|11.2Å |
| | SHCIAEVEK (SEQ ID NO: 89)\|(SEQ ID NO: 90) | S310-K318 | | | | $E_A315\|E_A317$ | 570.778 | 2 | |

TABLE 2-continued

Summary of DHSO Inter-Linked
BSA Peptides Identified by LC MS"

| # | Peptide Seq | AA location | MS m/z | z | Δ (PPM) | Mod. Position | MS2 m/z | z | Distance (Cα-Cα) |
|---|---|---|---|---|---|---|---|---|---|
| 34 | LKECCDKPLLEK (SEQ ID NO: 83) | L298-K309 | 721.8368 | 4 | 0.393 | $E_A300$ | 800.914 | 2 | 26.4Å |
| | CCTKPESER (SEQ ID NO: 71) | C460-R468 | | | | $E_A467$ | 617.769 | 2 | |
| 35 | LKECCDKPLLEK (SEQ ID NO: 85) \| (SEQ ID NO: 86) | L298-K309 | 721.8368 | 4 | 0.393 | $E_T300\|D_T303$ | 816.901 | 2 | 26.4Å\|31.1Å |
| | CCTKPESER (SEQ ID NO: 71) | C460-R468 | | | | $E_A467$ | 617.769 | 2 | |
| 36 | LKECCDKPLLEK (SEQ ID NO: 85) \| (SEQ ID NO: 86) | L298-K309 | 494.8425 | 5 | -2.149 | $E_T300\|D_T303$ | 544.935 | 3 | 40.9Å\|41.7Å |
| | NYQEAK (SEQ ID NO: 92) | N341-K346 | | | | $E_A344$ | 410.702 | 2 | |
| 37 | LKHLVDEPQNLIK (SEQ ID NO: 93) \| (SEQ ID NO: 94) | L400-K412 | 580.4977 | 5 | 7.275 | $D_T405\|E_T406$ | 823.959 | 2 | 13.6Å\|13.1Å |
| | CCTKPESER (SEQ ID NO: 70) \| (SEQ ID NO: 71) | C460-R468 | | | | $E_A465\|E_A467$ | 412.183 | 3 | 15.8Å\|15.3Å |
| 38 | LCVLHEK (SEQ ID NO: 96) | L483-K489 | 518.7810 | 4 | 1.484 | $E_T488$ | 499.749 | 2 | 10.7Å |
| | TPVSEKVTK (SEQ ID NO: 97) | T490-K498 | | | | $E_T494$ | 544.793 | 2 | |
| 39 | LVNELTEFAK (SEQ ID NO: 100) | L66-K75 | 692.8486 | 4 | -.732 | $E_A69$ | 616.337 | 2 | 9.3Å |
| | SLHTLFGDELCK (SEQ ID NO: 102) | S89-K100 | | | | $E_A97$ | 744.370 | 2 | |
| 40 | LVNELTEFAK (SEQ ID NO: 101) | L66-K75 | 692.8496 | 4 | 0.712 | $E_A72$ | 616.337 | 2 | 13.3Å |
| | SLHTLFGDELCK (SEQ ID NO: 102) | S89-K100 | | | | $E_A97$ | 744.370 | 2 | |
| 41 | LVNELTEFAK (SEQ ID NO: 100) | L66-K75 | 692.8486 | 4 | -.732 | $E_A69$ | 616.338 | 2 | 9.3Å\|12.1Å |
| | SLHTLFGDELCK (SEQ ID NO: 103) \| (SEQ ID NO: 104) | S89-K100 | | | | $D_T96\|E_T97$ | 760.357 | 2 | |
| 42 | LVNELTEFAK (SEQ ID NO: 101) | L66-K75 | 692.8502 | 4 | 1.578 | $E_A72$ | 616.338 | 2 | 15.2Å\|13.3Å |
| | SLHTLFGDELCK (SEQ ID NO: 103) \| (SEQ ID NO: 104) | S89-K100 | | | | $D_T96\|E_T97$ | 760.357 | 2 | |
| 43 | NECFLSHKDDSPDLPK (SEQ ID NO: 105) | N123-K138 | 746.1718 | 5 | -7.481 | $D_A135$ | 657.309 | 3 | 13.5Å |
| | KVPQVSTPTLVEVSR (SEQ ID NO: 106) | K437-R451 | | | | $E_A448$ | 854.493 | 2 | |
| 44 | QNCDQFEK (SEQ ID NO: 39) | Q413-K420 | 518.7349 | 4 | .292 | $D_T416$ | 584.731 | 2 | 16.9Å |
| | ATEEQLK (SEQ ID NO: 46) | A562-K568 | | | | $E_A564$ | 443.736 | 2 | |
| 45 | QNCDQFEK (SEQ ID NO: 39) | Q413-K420 | 605.7531 | 4 | 2.460 | $E_T419$ | 568.745 | 2 | 16.8Å |
| | CCTKPESER (SEQ ID NO: 72) | C460-R468 | | | | $E_T467$ | 633.756 | 2 | |
| 46 | QNCDQFEK (SEQ ID NO: 40) | Q413-K420 | 605.7520 | 4 | .645 | $E_A419$ | 584.730 | 2 | 14.0Å |
| | CCTKPESER (SEQ ID NO: 73) | C460-R468 | | | | $E_T465$ | 633.755 | 2 | |

TABLE 2-continued

Summary of DHSO Inter-Linked
BSA Peptides Identified by LC MS"

| # | Peptide Seq | AA location | MS m/z | z | Δ (PPM) | Mod. Position | MS2 m/z | z | Distance (Cα-Cα) |
|---|---|---|---|---|---|---|---|---|---|
| 47 | QNCDQFEK (SEQ ID NO: 41) | Q413-K420 | 605.7518 | 4 | .314 | $E_T419$ | 584.730 | 2 | 14.0Å\|16.8Å |
|  | CCTKPESER (SEQ ID NO: 73)\| (SEQ ID NO: 72) | C460-R468 |  |  |  | $E_T465$\|$E_T467$ | 633.756 | 2 |  |
| 48 | QNCDQFEK (SEQ ID NO: 42) | Q413-K420 | 605.7521 | 4 | 0.810 | $D_A416$ | 568.744 | 2 | 12.6Å |
|  | CCTKPESER (SEQ ID NO: 73) | C460-R468 |  |  |  | $E_T465$ | 633.756 | 2 |  |
| 49 | QNCDQFEK (SEQ ID NO: 41) | Q413-K420 | 484.8036 | 5 | 1.768 | $D_T416$ | 584.730 | 2 | 12.6Å\|15.7Å |
|  | CCTKPESER (SEQ ID NO: 70)\| (SEQ ID NO: 71) | C460-R468 |  |  |  | $E_A465$\|$E_A467$ | 412.183 | 3 |  |
| 50 | QNCDQFEK (SEQ ID NO: 40) | Q413-K420 | 684.0776 | 4 | 0.508 | $E_A419$ | 568.744 | 2 | 8.2Å |
|  | LGEYGFQNALIVR (SEQ ID NO: 77) | L421-R433 |  |  |  | $E_A423$ | 774.420 | 2 |  |
| 51 | RPCFSALTPDETYVPK (SEQ ID NO: 107) | R508-K523 | 721.8555 | 4 | 1.171 | $E_A518$ | 974.982 | 2 | 17.8Å |
|  | ATEEQLK (SEQ ID NO: 46) | A562-K568 |  |  |  | $E_A564$ | 443.735 | 2 |  |
| 52 | SEIAHR (SEQ ID NO: 108) | S29-R34 | 585.9390 | 6 | 1.516 | $E_T30$ | 406.695 | 2 | 16.7Å |
|  | VHKECCHGDLLECADDRADLAK (SEQ ID NO: 56) | V264-K285 |  |  |  | $D_A282$ | 670.804 | 4 |  |
| 53 | SHCIAEVEK (SEQ ID NO: 91)\| (SEQ ID NO: 88) | S310-K318 | 606.7698 | 4 | 2.091 | $E_T315$\|$E_T317$ | 586.763 | 2 | 18.1Å\|15.8Å |
|  | CCTKPESER (SEQ ID NO: 72) | C460-R468 |  |  |  | $E_T467$ | 633.755 | 2 |  |
| 54 | SHCIAEVEK (SEQ ID NO: 90) CCTKPESER (SEQ ID NO: 72) | S310-K318 C460-R468 | 606.7702 | 4 | 2.751 | $E_A317$ $E_T467$ | 570.778 633.756 | 2 2 | 15.0Å |
| 55 | SHCIAEVEK (SEQ ID NO: 88) | S310-K318 | 485.6177 | 5 | 2.924 | $E_T317$ | 586.764 | 2 | 20.3Å\|15.0Å |
|  | CCTKPESER (SEQ ID NO: 70)\| (SEQ ID NO: 71) | C460-R468 |  |  |  | $E_A465$\|$E_A467$ | 412.183 | 3 |  |
| 56 | SHCIAEVEK (SEQ ID NO: 91) | S310-K318 | 503.4868 | 4 | 2.604 | $E_T315$ | 586.764 | 2 | 35.7Å |
|  | NYQEAK (SEQ ID NO: 92) | N341-K346 |  |  |  | $E_A344$ | 410.701 | 2 |  |
| 57 | VHKECCHGDLLECADDRADLAK (SEQ ID NO: 57)\| (SEQ ID NO: 54)\| (SEQ ID NO: 55)\| (SEQ ID NO: 56) | V264-K285 | 645.9636 | 6 | 4.495 | $E_A275$\|$D_A278$ $D_A279$\|$D_A282$ | 670.808 | 4 | 27.6Å\|24.5Å\| 22.8Å\|21.2Å |
|  | SHCIAEVEK (SEQ ID NO: 88) | S310-K318 |  |  |  | $E_T317$ | 586.765 | 2 |  |
| 58 | VHKECCHGDLLECADDRADLAK (SEQ ID NO: 54)\| (SEQ ID NO: 55)\| (SEQ ID NO: 56) | V264-K285 | 707.8174 | 6 | 1.732 | $D_A278$\|$D_A279$ $D_A282$ | 670.807 | 4 | 16.7Å\|15.2Å\| 10.6Å |
|  | YICDNQDTISSK (SEQ ID NO: 44) | Y286-K297 |  |  |  | $D_T289$ | 772.330 | 2 |  |

TABLE 2-continued

Summary of DHSO Inter-Linked
BSA Peptides Identified by LC MS"

| # | Peptide Seq | AA location | MS m/z | z | Δ (PPM) | Mod. Position | MS2 m/z | z | Distance (Cα-Cα) |
|---|---|---|---|---|---|---|---|---|---|
| 59 | YICDNQDTISSK (SEQ ID NO: 44) | Y286-K297 | 730.8301 | 4 | 1.435 | $D_T289$ | 772.331 | 2 | 10.9Å |
| | ECCDKPLLEK (SEQ ID NO: 109) | E300-K309 | | | | $D_T303$ | 680.325 | 2 | |
| 60 | YICDNQDTISSK (SEQ ID NO: 43) | Y286-K297 | 791.1262 | 4 | 3.024 | $D_T292$ | 772.331 | 2 | 15.0Å |
| | LKECCDKPLLEK (SEQ ID NO: 86) | L298-K309 | | | | $D_T303$ | 816.902 | 2 | |
| 61 | YICDNQDTISSK (SEQ ID NO: 45) | Y286-K297 | 791.1237 | 4 | -0.136 | $D_A292$ | 756.334 | 2 | 13.4Å\|15.0Å |
| | LKECCDKPLLEK (SEQ ID NO: 85) \| (SEQ ID NO: 86) | L298-K309 | | | | $E_T300\|D_T303$ | 816.900 | 2 | |
| 62 | YICDNQDTISSK (SEQ ID NO: 45) | Y286-K297 | 676.0577 | 4 | 2.777 | $D_A292$ | 756.345 | 2 | 15.5Å |
| | SHCIAEVEK (SEQ ID NO: 88) | S310-K318 | | | | $E_T317$ | 586.764 | 2 | |

Note:
"|" means or; "&" means and; "T": unsaturated thiol moiety; "A": alkene moiety; "ox" means oxidation.

In some embodiments, the number of unique peptides obtained depends on several factors, including but not limited to, size, complexity, conformation, subunits, domains, etc., of the protein and/or protein complex. In some embodiments, the number of unique peptides range from about 5 to about 500. In some embodiments, the number of unique peptides range from about 10 to about 1000. In some embodiments, the number of unique peptides range from about 50 to about 5000. In some embodiments, the number of unique peptides range from about 500 to about 50,000. Collectively, the results presented thus far indicate that DHSO can effectively cross-link acidic residue containing peptides and proteins at neutral pH in the presence of DMTMM as the activating agent. More importantly, in some embodiments, the results demonstrate that DHSO cross-linked peptides indeed exhibit the same characteristic MS² fragmentation patterns as expected to allow their facile and accurate identification.

DHSO Cross-Linking Maps of Myoglobin and BSA

In order to assess the efficacy and sequence coverage of DHSO cross-linking on model proteins, cross-linking maps of myoglobin and BSA based on the identified DHSO inter-linked peptides were generated. The secondary structures of equine myoglobin comprise of eight α-helices and one short $3_{10}$ helix (PDB: 1DWR) (FIG. 5A). The globular nature of myoglobin suggests that many of the helices are in close proximity to one another in three-dimensional space. The DHSO cross-link map of myoglobin based on the 33 unique E|D-E|D linkages is illustrated in FIG. 5B, describing numerous intra- and inter-secondary structure interactions (e.g. α1-α5, α1-α8, α2-α4, α3-α4, α3-α8, α4-α5, α4-α8, α6-α8, α7-α8, and α8-α8). To evaluate the legitimacy of identified cross-links, the cross-linked residues were mapped onto the crystal structure of myoglobin and calculated the distances between their alpha carbons (Cα-Cα distances) (FIG. 5D and FIG. 5F). Considering the length of the DHSO (12.5 Å) and the distances contributed by DIE side chains (4.5 Å|6.0 Å, respectively), as well as backbone flexibility and structural dynamics, the theoretical upper limit for the Cα-Cα distances between DHSO cross-linked acidic residues is estimated ~35 Å. Therefore, the distance threshold for cross-linkable D/E residues was set as 35 Å. 27 of the 32 myoglobin DHSO cross-links were mapped in the structure, with all of them have a Cα-Cα distance <35 Å. The remaining 5 linkages not mapped on to the structure because they were identified as possible sites of oligomerization, in which identical residues or peptide sequences were cross-linked together.

Figure 12A:
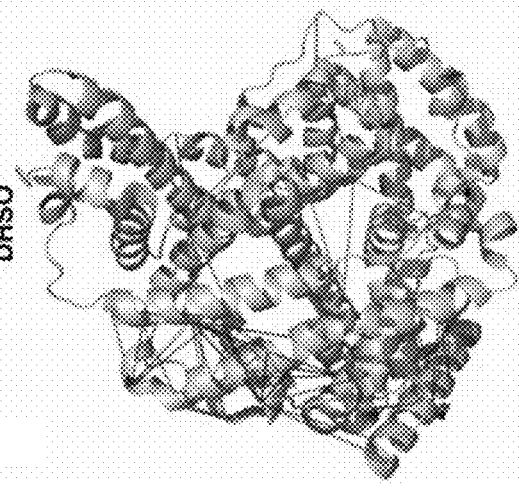
FIG. 12A shows BSA cross-link maps on its crystal structure (PDB: 4F5S) with DHSO crosslink map (dotted lines).

Similarly, a DHSO cross-link map of BSA was generated based on the 69 unique E|D-E|D linkages (FIG. 6A). When mapped to a previously published BSA crystal structure (PDB: 4F5S), 65 out of 69 BSA linkages, 94%, were calculated to have Cα-Cα distances below 35 Å (FIG. 12A and FIG. 12C). Structural flexibility and/or oligomerization of BSA likely attribute to the other four identified linkages found to be >35 Å.

In some embodiments, the Cα-Cα distance ranges from about 5 Å to about 50 Å. In some embodiments, the Cα-Cα distance ranges from about 1 Å to about 100 Å. In some embodiments, the number of cross-links range from about 1 to about 100. In some embodiments, for a Cα-Cα distance range of about 0-5 Å, the number of cross-links range from about 1 to about 100. In some embodiments, for a Cα-Cα distance range of about 5-10 Å, the number of cross-links range from about 1 to about 100. In some embodiments, for a Cα-Cα distance range of about 10-15 Å, the number of cross-links range from about 1 to about 100. In some embodiments, for a Cα-Cα distance range of about 15-20 Å, the number of cross-links range from about 1 to about 100. In some embodiments, for a Cα-Cα distance range of about 20-25 Å, the number of cross-links range from about 1 to about 100. In some embodiments, for a Cα-Cα distance range of about 25-30 Å, the number of cross-links range from about 1 to about 100. In some embodiments, for a Cα-Cα distance range of about 30-35 Å, the number of cross-links range from about 1 to about 100. In some embodiments, for a Cα-Cα distance range of about 35-40 Å, the number of cross-links range from about 1 to about 100. In some embodiments, for a Cα-Cα distance range of about 40-45 Å, the number of cross-links range from about 1 to about 100. In some embodiments, for a Cα-Cα distance range of about 45-50 Å, the number of cross-links range from about 1 to about 100. In some embodiments, for a Cα-Cα distance range of about 50-55 Å, the number of cross-links range from about 1 to about 100. In some embodiments, for a Cα-Cα distance range of about 55-60 Å, the number of cross-links range from about 1 to about 100. In some embodiments, for a Cα-Cα distance range of about 60-65 Å, the number of cross-links range from about 1 to about 100. In some embodiments, for a Cα-Cα distance range of about 65-70 Å, the number of cross-links range from about 1 to about 100. In some embodiments, for a Cα-Cα distance range of about 70-75 Å, the number of cross-links range from about 1 to about 100. In some embodiments, for a Cα-Cα distance range of about 75-80 Å, the number of cross-links range from about 1 to about 100. In some embodiments, for a Cα-Cα distance range of about 80-85 Å, the number of cross-links range from about 1 to about 100. In some embodiments, for a Cα-Cα distance range of about 85-90 Å, the number of cross-links range from about 1 to about 100. In some embodiments, for a Cα-Cα distance range of about 90-95 Å, the number of cross-links range from about 1 to about 100. In some embodiments, for a Cα-Cα distance range of about 95-100 Å, the number of cross-links range from about 1 to about 100. In some embodiments, the number of cross-links range from about 100 to about 10,000 for one or more of the Cα-Cα distance ranges disclosed herein. In some embodiments, about 5% to about 45% of intra-links are within any of the ranges disclosed herein. In some embodiments, about 25% to about 65% of intra-links are within any of the ranges disclosed herein. In some embodiments, about 45% to about 99% of intra-links are within any of the ranges disclosed herein. In some embodiments, about 5% to about 45% of inter-links are within any of the ranges disclosed herein. In some embodiments, about 25% to about 65% of inter-links are within any of the ranges disclosed herein. In some embodiments, about 45% to about 99% of inter-links are within any of the ranges disclosed herein. In some embodiments, about 5% to about 45% of intra- and inter-links are within any of the ranges disclosed herein. In some embodiments, about 25% to about 65% of intra- and inter-links are within any of the ranges disclosed herein. In some embodiments, about 45% to about 99% of intra- and inter-links are within any of the ranges disclosed herein.

As shown in FIG. 6A, DHSO inter-links were distributed throughout the primary sequence of BSA, with regions of dense cross-link clusters identified in regions with higher α-helix density. This even distribution is likely due to the widespread dispersion of aspartic acid and glutamic acid residues throughout the protein. In some embodiments, the results herein suggest that DHSO cross-linking yields cross-links within expected distance constraints useful for structural elucidation for computational modeling in the same way as primary amine cross-linked data.

Comparison of MS-Cleavable and Non-Cleavable Acidic Residue Cross-Linking

Previously, two non-cleavable acidic residue cross-linkers, i.e., adipic acid dihydrazide (ADH) and pimetic acid dihydrazide (PDH), were used for probing the structure of bovine serum albumin[22], which identified 27 and 35 unique acidic residue linkages, respectively[22]. A comparison of the linkage maps generated for DHSO, ADH, and PDH cross-linking of BSA (FIG. 6A-FIG. 6C) revealed a high degree of similarity in proximally cross-linked regions. Apart from covering interaction regions cross-linked by ADH and PDH, DHSO cross-linking resulted in 34 additional unique DIE-DIE linkages. ADH (FIG. 6B) and PDH (FIG. 6C) crosslink maps were generated based on data obtained by Leitner et al.[22]. These unique DHSO cross-links are generally clustered in regions of particularly high acidic residue density, such as the regions between D25 and D97, E250 and E344, and D405 to E494 (FIG. 6A-FIG. 6C). Limitations in bioinformatics software for analyzing non-cleavable cross-linked peptides have been previously noted 22, which makes it considerably more challenging for accurate identification of acidic residue cross-linked peptides due to their higher frequency than lysine and resulting increase in searching space. In contrast, CID induced cleavage of DHSO cross-linked peptides during $MS^2$ significantly simplify subsequent peptide sequencing with $MS^3$. Given the same acidic residue reactive chemistry, the increase in identified cross-links using DHSO is mainly attributed to the simplified cross-link identification with improved accuracy afforded by MS-cleavability of DHSO cross-linked peptides. This ultimately facilitates unambiguous identification of individual linkages amidst peptides with multiple acidic residues in sequence. These results demonstrate the advantage of using DHSO, a MS-cleavable cross-linking reagent targeting acidic residues for probing protein-protein interactions over non-cleavable reagents.

Comparison of DHSO and DSSO Cross-Linking

To assess the complementarity between acidic residue and primary amine cross-linking data, the similarities and differences between DHSO and DSSO cross-linking of selected model proteins were examined. To this end, LC-$MS^n$ analyses of DSSO cross-linked myoglobin and BSA respectively were performed. As summarized in Table 3 and Table 4, 19 unique DSSO inter-linked myoglobin peptides and 33 unique DSSO inter-linked BSA peptides were identified.

TABLE 3

Summary of DSSO Inter-Linked Myoglobin Peptides Identified by LC $MS^n$

| # | Peptide Seq | AA location | MS m/z | z | Δ (PPM) | Mod. Position | MS2 m/z | z | Distance (Cα-Cα) |
|---|---|---|---|---|---|---|---|---|---|
| 1 | FDKFK (SEQ ID NO: 111) | F44-K48 | 618.5516 | 5 | 0.116 | $K_T46$ | 770.355 | 1 | 14.6Å |
|   | KKGHHEAELKPLAQSHATKHK (SEQ ID NO: 112) | K79-K99 | | | | $K_T97$ | 584.053 | 4 | |
| 2 | FDKFKHLKTEAEMK (SEQ ID NO: 113) | F44-K57 | 715.5761 | 5 | -0.108 | $K_A46$ & $K_A48$ & $K_T51$ | 649.311 | 3 | 11.9Å\|15.7Å\|18.3Å |
|   | KHGTVVLTALGGILK (SEQ ID NO: 114) | K64-K78 | | | | $K_T64$ | 796.963 | 2 | |

TABLE 3-continued

Summary of DSSO Inter-Linked Myoglobin
Peptides Identified by LC MS"

| # | Peptide Seq | AA location | MS m/z | z | Δ (PPM) | Mod. Position | MS2 m/z | z | Distance (Cα-Cα) |
|---|---|---|---|---|---|---|---|---|---|
| 3 | FKHLK (SEQ ID NO: 115) | F47-K51 | 492.2618 | 6 | 1.093 | $K_A48$ | 363.719 | 2 | 27.1Å\|17.1Å |
|   | GHHEAELKPLAQSHATKHK (SEQ ID NO: 119)\| (SEQ ID NO: 120) | G81-K99 | | | | $K_T88\|K_T97$ | 544.037 | 4 | |
| 4 | FKHLK (SEQ ID NO: 116) | F47-K51 | 590.5117 | 5 | -0.608 | $K_T48$ | 758.406 | 1 | 17.1Å |
|   | GHHEAELKPLAQSHATKHK (SEQ ID NO: 121) | G81-K99 | | | | $K_A97$ | 544.037 | 4 | |
| 5 | FKHLK (SEQ ID NO: 116) | F47-K51 | 391.9812 | 4 | -0.157 | $K_T48$ | 363.719 | 2 | 15.6Å |
|   | HKIPIK (SEQ ID NO: 117) | H98-K103 | | | | $K_A99$ | 411.239 | 2 | |
| 6 | FKHLKTEAEMKASEDLKK (SEQ ID NO: 122) | F47-K64 | 970.3080 | 6 | 0.463 | $K_A48$ & $K_T51$ & $K_A57$ | 776.385 | 3 | 26.1Å\|24.4Å\|15.4Å |
|   | YLEFISDAIIHVLHSKHPGDFGADAQGAMTK (SEQ ID NO: 123) | Y104-K134 | | | | $K_T119$ | 1152.221 | 3 | |
| 7 | HGTVVLTALGGILKK (SEQ ID NO: 125) | H65-K79 | 608.5053 | 6 | 1.553 | $K_A78$ | 520.987 | 3 | 5.3Å |
|   | KGHHEAELKPLAQSHATK (SEQ ID NO: 126) | K80-K97 | | | | $K_T80$ | 690.017 | 3 | |
| 8 | KHGTVVLTALGGILK (SEQ ID NO: 114) | K64-K78 | 647.3630 | 4 | -0.850 | $K_T64$ | 796.963 | 2 | 27.0Å |
|   | NDIAAKYK (SEQ ID NO: 128) | N141-K148 | | | | $K_A146$ | 488.759 | 2 | |
| 9 | KKGHHEAELKPLAQSHATK (SEQ ID NO: 11) | K79-K97 | 837.6671 | 4 | -1.356 | $K_A79$ & $K_T80$ & $K_A88$ | 768.724 | 3 | 18.0Å, 18.4Å, 7.1Å |
|   | NDIAAKYK (SEQ ID NO: 129) | N141-K148 | | | | $K_T146$ | 976.510 | 1 | |
| 10 | KKGHHEAELKPLAQSHATK (SEQ ID NO: 12)\| (SEQ ID NO: 13) | K79-K97 | 638.7356 | 5 | 0.486 | $K_T80\|K_T88$ | 549.789 | 4 | 18.4Å\|7.1Å |
|   | NDIAAKYK (SEQ ID NO: 129) | N141-K148 | | | | $K_T146$ | 1008.485 | 1 | |
| 11 | KGHHEAELKPLAQSHATK (SEQ ID NO: 127) | K80-K97 | 766.1448 | 4 | 1.629 | $K_T88$ | 690.018 | 3 | 7.1Å |
|   | NDIAAKYK (SEQ ID NO: 128) | N141-K148 | | | | $K_A146$ | 976.511 | 1 | |
| 12 | LFTGHPETLEKFDK (SEQ ID NO: 130) | L33-K46 | 416.0513 | 6 | 0.971 | $K_A43$ | 429.721 | 4 | 8.0Å |
|   | FKHLK (SEQ ID NO: 115) | F47-K51 | | | | $K_A48$ | 363.719 | 2 | |
| 13 | LFTGHPETLEKFDK (SEQ ID NO: 131) | L33-K46 | 639.3386 | 4 | -1.892 | $K_T43$ | 874.421 | 2 | 7.7Å |
|   | HKIPIK (SEQ ID NO: 117) | H98-K103 | | | | $K_A99$ | 395.253 | 2 | |
| 14 | LFTGHPETLEKFDK (SEQ ID NO: 131) | L33-K46 | 737.5630 | 6 | .054 | $K_T43$ | 874.423 | 2 | 7.7Å\|13.0Å |
|   | HKIPIKYLEFISDAIIHVLHSK (SEQ ID NO: 132)\| (SEQ ID NO: 133) | H98-K119 | | | | $K_A99\|KA103$ | 664.631 | 4 | |

TABLE 3-continued

Summary of DSSO Inter-Linked Myoglobin Peptides Identified by LC MS"

| # | Peptide Seq | AA location | MS m/z | z | Δ (PPM) | Mod. Position | MS2 m/z | z | Distance (Cα-Cα) |
|---|---|---|---|---|---|---|---|---|---|
| 15 | LFTGHPETLEKFDK (SEQ ID NO: 131) | L33-K46 | 801.4203 | 6 | 2.184 | $K_T43$ | 874.421 | 2 | 7.7Å, 20.3Å, 10.5Å |
| | KKGHHEAELKPLAQSHATKHKIPIK (SEQ ID NO: 134) | K79-K103 | | | | $K_A88$ & $K_T97$ & $K_A99$ | 755.913 | 4 | |
| 16 | LFTGHPETLEKFDK (SEQ ID NO: 131) | L33-K46 | 831.8438 | 5 | .575 | $K_T43$ | 874.421 | 2 | 13.0Å |
| | IPIKYLEFISDAIIHVLHSK (SEQ ID NO: 135) | I100-K119 | | | | $K_A103$ | 797.454 | 3 | |
| 17 | LFTGHPETLEKFDKFKHLK (SEQ ID NO: 136) | L33-K51 | 561.7958 | 6 | -1.21 | $K_T43$ & $K_A46$ & $K_T48$ | 636.063 | 4 | 7.7Å, 15.0Å, 15.6Å |
| | HKIPIK (SEQ ID NO: 118) | H98-K103 | | | | $K_A99$ | 395.253 | 2 | |
| 18 | TEAEMKASEDLK (SEQ ID NO: 137) | T52-K63 | 754.6490 | 4 | 0.028 | $K_A57$ | 703.330 | 2 | 11.6Å |
| | KHGTVVLTALGGILK (SEQ ID NO: 114) | K64-K78 | | | | $K_T64$ | 796.963 | 2 | |
| 19 | TEAEMKASEDLKK (SEQ ID NO: 138) | T52-K65 | 100.0855 | 5 | -2.117 | $K_A57$ | 767.378 | 2 | 15.4Å |
| | YLEFISDAIIHVLHSKHPGDFGADAQGAMTK (SEQ ID NO: 124) | Y104-K134 | | | | $K_A119$ | 1141.568 | 3 | |

Note:
"|" means or; "&" means and; "T": unsaturated thiol moiety; "A": alkene moiety; "ox" means oxidation.

TABLE 4

Summary of DSSO Inter-Linked BSA Peptides Identified by LC MS"

| # | Peptide Seq | AA location | MS m/z | z | Δ (PPM) | Mod. Position | MS2 m/z | z | Distance (Cα-Cα) |
|---|---|---|---|---|---|---|---|---|---|
| 1 | ALKAWSVAR (SEQ ID NO: 139) | A233-R241 | 744.1126 | 4 | 4.399 | $K_A235$ | 528.305 | 2 | 13.5Å |
| | LAKEYEATLEECCAK (SEQ ID NO: 141) | L372-K386 | | | | $K_T374$ | 950.911 | 2 | |
| 2 | ALKAWSVAR (SEQ ID NO: 139) | A233-R241 | 754.9589 | 5 | 3.924 | $K_A235$ | 528.306 | 2 | 9.7Å |
| | VHKECCHGDLLECADDRADLAK (SEQ ID NO: 58) | V264-K285 | | | | $K_T266$ | 900.056 | 3 | |
| 3 | ALKAWSVAR (SEQ ID NO: 140) | A233-R241 | 578.8257 | 4 | 0.636 | $K_T235$ | 544.291 | 2 | 9.0Å |
| | LVTDLTKVHK (SEQ ID NO: 142) | L257-K266 | | | | $K_A263$ | 604.357 | 2 | |
| 4 | AEFVEVTKLVTDLTK (SEQ ID NO: 144) | A249-K263 | 948.9763 | 4 | 5.128 | $K_A256$ | 873.984 | 2 | 13.8Å |
| | ADLAKYICDNQDTISSK (SEQ ID NO: 145) | A281-K297 | | | | $K_T285$ | 1014.458 | 2 | |
| 5 | ADLAKYICDNQDTISSK (SEQ ID NO: 145) | A281-K297 | 889.6097 | 5 | 1.632 | $K_T285$ | 1014.458 | 2 | 9.1Å |
| | ECCDKPLLEKSHCIAVEK (SEQ ID NO: 146) | E300-K318 | | | | $K_A309$ | 800.374 | 3 | |
| 6 | ADLAKYICDNQDTISSK (SEQ ID NO: 145) | A281-K297 | 889.6097 | 5 | 1.632 | $K_T285$ | 1014.458 | 2 | 11.3Å\|9.1Å |
| | ECCDKPLLEKSHCIAVEK (SEQ ID NO: 147)\|(SEQ ID NO: 148) | E300-K318 | | | | $K_T304$\|$K_T309$ | 811.031 | 3 | |

TABLE 4-continued

Summary of DSSO Inter-Linked
BSA Peptides Identified by LC MS"

| # | Peptide Seq | AA location | MS m/z | z | Δ (PPM) | Mod. Position | MS2 m/z | z | Distance (Cα-Cα) |
|---|---|---|---|---|---|---|---|---|---|
| 7 | CASIQKFGER (SEQ ID NO: 149) | C223-R232 | 792.6119 | 4 | 3.328 | $K_4$228 | 625.306 | 2 | 16.4Å |
|  | LAKEYEATLEECCAK (SEQ ID NO: 141) | L372-K386 |  |  |  | $K_T$374 | 950.910 | 2 |  |
| 8 | CASIQKFGER (SEQ ID NO: 149) | C223-R232 | 723.8583 | 4 | 2.115 | $K_4$228 | 625.305 | 2 | 13.2Å |
|  | LCVLHEKTPVSEK (SEQ ID NO: 151) | L483-K495 |  |  |  | $K_T$489 | 813.408 | 2 |  |
| 9 | CASIQKFGER (SEQ ID NO: 149) | C223-R232 | 705.5812 | 4 | 3.067 | $K_4$228 | 641.290 | 2 | 13.1Å |
|  | VTKCCTESLVNR (SEQ ID NO: 152) | V496-R507 |  |  |  | $K_T$498 | 776.852 | 2 |  |
| 10 | CASIQKFGER (SEQ ID NO: 149) | C223-R232 | 900.6266 | 5 | 0.080 | $K_4$228 | 625.305 | 2 | 13.2Å\|17.6Å\|13.1Å |
|  | LCVLHEKTPVSEKVTKCCTESLVNR (SEQ ID NO: 154) | L483-K507 |  |  |  | $K_T$489 & $K_T$495 & $K_4$498 | 1071.836 | 3 |  |
| 11 | CASIQKFGER (SEQ ID NO: 150) | C223-R232 | 543.2742 | 4 | 0.293 | $K_T$228 | 641.291 | 2 | 27.2Å |
|  | SLGKVGTR (SEQ ID NO: 153) | S452-R459 |  |  |  | $K_4$455 | 436.254 | 2 |  |
| 12 | DTHKSEIAHR (SEQ ID NO: 53) | D25-R34 | 520.8516 | 5 | 3.487 | $K_4$28 | 416.544 | 3 | 13.4Å |
|  | FKDLGEEHFK (SEQ ID NO: 155) | F35-K44 |  |  |  | $K_T$36 | 668.308 | 2 |  |
| 13 | DTHKSEIAHR (SEQ ID NO: 53) | D25-R34 | 501.6659 | 5 | 3.313 | $K_4$28 | 416.544 | 3 | 21.4Å |
|  | LVTDLTKVHK (SEQ ID NO: 143) | L257-K266 |  |  |  | $K_T$263 | 620.343 | 2 |  |
| 14 | FPKAEFVEVTK (SEQ ID NO: 157) | F246-K256 | 746.8786 | 4 | 3.617 | $K_T$248 | 674.864 | 2 | 15.6Å |
|  | LKECCDKPLLEK (SEQ ID NO: 87) | L298-K309 |  |  |  | $K_4$299 | 809.889 | 2 |  |
| 15 | FPKAEFVEVTK (SEQ ID NO: 158) | F246-K256 | 784.8886 | 4 | 3.457 | $K_T$248 | 674.863 | 2 | 11.7Å |
|  | YICDNQDTISSKLK (SEQ ID NO: 159) | Y286-K299 |  |  |  | $K_T$297 | 885.909 | 2 |  |
| 16 | FKDLGEEHFK (SEQ ID NO: 156) | F35-K44 | 803.7743 | 5 | 5.714 | $K_4$36 | 652.321 | 2 | 9.2Å |
|  | LVNELTEFAKTCVADESHAGCEK (SEQ ID NO: 160) | L66-K88 |  |  |  | $K_4$75 | 888.078 | 3 |  |
| 17 | FKDLGEEHFK (SEQ ID NO: 156) | F35-K44 | 837.8948 | 4 | 5.217 | $K_4$36 | 652.320 | 2 | 16.7Å |
|  | ADLAKYICDNQDTISSK (SEQ ID NO: 145) | A281-K297 |  |  |  | $K_T$285 | 1014.458 | 2 |  |
| 18 | HPYFYAPELLYYANKYNGVFQECCQAEDK (SEQ ID NO: 161) | H169-K197 | 1014.2459 | 5 | 3.074 | $K_4$183 | 1224.555 | 3 | 13.6Å |
|  | ECCDKPLLEK (SEQ ID NO: 110) | E300-309 |  |  |  | $K_4$304 | 673.313 | 2 |  |
| 19 | HPYFYAPELLYYANKYNGVFQECCQAEDK (SEQ ID NO: 162) | H169-K197 | 1036.6772 | 5 | 2.428 | $K_T$183 | 1235.200 | 3 | 10.1Å |
|  | GACLLPKIETM(ox)R (SEQ ID NO: 163) | G198-R209 |  |  |  | $K_4$204 | 728.878 | 2 |  |
| 20 | HKPKATEEQLK (SEQ ID NO: 164) | H558-K568 | 555.8971 | 5 | 0.899 | $K_4$561 | 454.918 | 3 | — |
|  | HKPKATEEQLK (SEQ ID NO: 165) | H558-K568 |  |  |  | $K_T$561 | 697.863 | 2 |  |

TABLE 4-continued

Summary of DSSO Inter-Linked BSA Peptides Identified by LC MS"

| # | Peptide Seq | AA location | MS m/z | z | Δ (PPM) | Mod. Position | MS2 m/z | z | Distance (Cα-Cα) |
|---|---|---|---|---|---|---|---|---|---|
| 21 | KQTALVELLK (SEQ ID NO: 167) | K548-K557 | 879.4573 | 4 | 0.408 | $K_4$548 | 598.868 | 2 | 14.3Å |
| | ATEEQLKTVM(ox)ENFVAFVDK (SEQ ID NO: 168) | A562-K580 | | | | $K_7$568 | 1151.104 | 2 | |
| 22 | LKPDPNTLCDEFK (SEQ ID NO: 80) | L139-K151 | 795.8878 | 4 | 1.369 | $K_7$140 | 831.881 | 2 | 14.7Å |
| | FWGKYLYEIAR (SEQ ID NO: 170) | F157-R167 | | | | $K_4$160 | 750.391 | 2 | |
| 23 | LKPDPNTLCDEFK (SEQ ID NO: 80) | L139-K151 | 638.5690 | 4 | 0.425 | $K_7$140 | 831.880 | 2 | 21.3Å |
| | SLGKVGTR (SEQ ID NO: 153) | S452-R459 | | | | $K_4$455 | 436.255 | 2 | |
| 24 | LSQKFPK (SEQ ID NO: 171) | L242-K248 | 543.5061 | 4 | 4.415 | $K_4$245 | 451.263 | 2 | 20.5Å |
| | CCTKPESER (SEQ ID NO: 74) | C460-R468 | | | | $K_7$463 | 626.744 | 2 | |
| 25 | LKHLVDEPQNLIK (SEQ ID NO: 95) | L400-L412 | 603.3317 | 5 | 3.556 | $K_7$401 | 816.948 | 2 | 42.1Å\|38.3Å |
| | HKPKATEEQLK (SEQ ID NO: 166)\|(SEQ ID NO: 164) | H558-K568 | | | | $K_4$559\|$K_4$561 | 454.920 | 3 | |
| 26 | LFTFHADICTLPDTEKQIK (SEQ ID NO: 172) | L529-547 | 894.9782 | 4 | 6.080 | $K_4$544 | 1166.089 | 2 | 6.4Å |
| | KQTALVELLK (SEQ ID NO: 167) | K548-K557 | | | | $K_4$548 | 598.868 | 2 | |
| 27 | NECFLSHKDDSPDLPKLKPDPNTLCDEFK (SEQ ID NO: 173) | N123-K151 | 739.8589 | 6 | 2.696 | $K_7$138 | 887.159 | 4 | 19.9Å |
| | SLGKVGTR (SEQ ID NO: 153) | S452-R459 | | | | $K_4$455 | 436.254 | 2 | |
| 28 | DDSPDLPKLKPDPNTLCDEFK (SEQ ID NO: 174)\|(SEQ ID NO: 175) | D131-K151 | 773.1790 | 5 | 3.565 | $K_7$138\|$K_7$140 | 991.79 | 3 | 19.9Å\|21.3Å |
| | SLGKVGTR (SEQ ID NO: 153) | S452-R459 | | | | $K_4$455 | 436.254 | 2 | |
| 29 | QNCDQFEKLGEYGFQNALIVR (SEQ ID NO: 176) | Q413-R433 | 1226.3392 | 4 | 4.267 | $K_7$420 | 1308.109 | 2 | 14.6Å |
| | ATEEQLKTVM(ox)ENFVAFVDK (SEQ ID NO: 169) | A562-K580 | | | | $K_4$568 | 1135.061 | 2 | |
| 30 | QNCDQFEKLGEYGFQNALIVR (SEQ ID NO: 176) | Q413-R433 | 1082.5466 | 4 | 1.824 | $K_7$420 | 1308.113 | 2 | 22.3Å |
| | KVPQVSTPTLVEVSR (SEQ ID NO: 177) | K437-R451 | | | | $K_4$437 | 847.479 | 2 | |
| 31 | SLGKVGTR (SEQ ID NO: 153) | S452-R459 | 536.0019 | 4 | 3.445 | $K_4$455 | 436.255 | 2 | 13.5Å |
| | CCTKPESER (SEQ ID NO: 74) | C460-R468 | | | | $K_7$463 | 626.743 | 2 | |
| 32 | TPVSEKVTK (SEQ ID NO: 98) | T490-K498 | 491.6657 | 5 | 3.475 | $K_7$495 | 537.780 | 2 | 19.8Å\|18.7Å |
| | HKPKATEEQLK (SEQ ID NO: 166)\|(SEQ ID NO: 164) | H558-K568 | | | | $K_4$559\|$K_4$561 | 454.918 | 3 | |

TABLE 4-continued

Summary of DSSO Inter-Linked BSA Peptides Identified by LC MS"

| # | Peptide Seq | AA location | MS m/z | z | Δ (PPM) | Mod. Position | MS2 m/z | z | Distance (Cα-Cα) |
|---|---|---|---|---|---|---|---|---|---|
| 33 | TPVSEKVTK (SEQ ID NO: 99) | T490-K498 | 614.3301 | 4 | 3.141 | K$_4$495 | 521.794 | 2 | 18.7Å |
|  | HKPKATEEQLK (SEQ ID NO: 165) | H558-K568 |  |  |  | K$_7$561 | 697.861 | 2 |  |

Note:
"I" means or; "&" means and; "T": unsaturated thiol moiety; "A": alkene moiety; "ox" means oxidation.

Figure 12B:
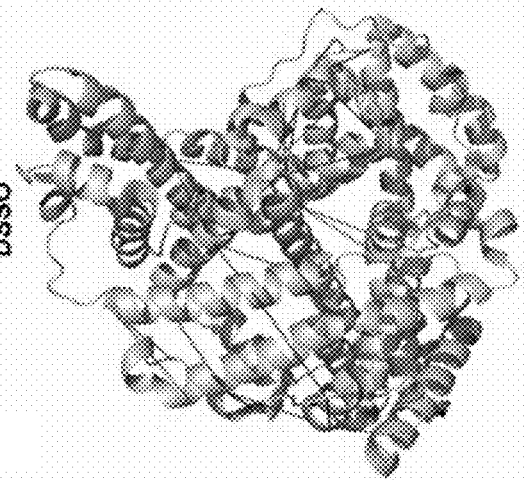
FIG. 12B shows BSA cross-link maps on its crystal structure (PDB: 4F5S) with DSSO crosslink map (dotted lines).
Figure 12C:
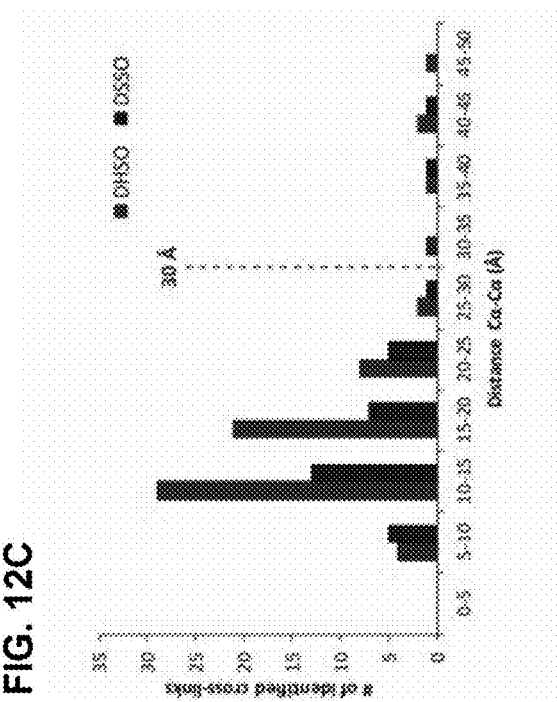
FIG. 12C The distribution plot of identified linkages versus their spatial distances between DIE-DIE for DHSO (gray) or K-K for DSSO (black) in BSA structure.

These linkages were then mapped onto their corresponding protein linear sequences (FIG. 5C and FIG. 6D) and the same crystal structures used in DHSO analysis (FIG. 5D and FIG. 12B). As shown, all of myoglobin DSSO cross-links and 94% of BSA DSSO cross-links corresponded to Cα-Cα distances ≤35 Å (FIG. 5D, FIG. 5E, FIG. 12B, and FIG. 12C). The two links that are outside the distance range may be a result of unexpected structural flexibility.

In the case of myoglobin, DSSO cross-linking identified several proximal helicase regions, such as α4-α5, α4-α7, α5-α8, α6-α8, and α5-3$_{10}$. In comparison, there is little overlap between DHSO and DSSO cross-link maps except the regions containing α4-α5 and α6-α8 (FIG. 5B and FIG. 5C), indicating that DHSO and DSSO cross-linking mapped different parts of interactions within myoglobin. The identified helicase interacting regions unique to DHSO or DSSO cross-linking correspond well with their cross-linkable residues and specific reactive chemistries. This is due to the fact that lysine and acidic residues are distributed unevenly across myoglobin sequence. For example, the N-terminal region of myoglobin (residues 1-41) spanning helices α1 through α3 contains only one lysine, but four glutamic acids and two aspartic acid residues. Therefore, profiling the interactions of the N-terminus within itself and with other parts of the protein will be difficult with amine-reactive cross-linking reagent such as DSSO. In contrast, acidic residue reactive cross-linker DHSO would be better suited for this purpose. Indeed, while DSSO was not able to cover this region as expected, DHSO cross-linking enabled the identification of 11 inter-linked peptides describing multiple interactions between the N-terminus and other parts of the protein (i.e. α1-α5, α1-α8, α2-α4, α3-α4, and α3-α8). While DHSO provided exclusive data from the lysine scarce N-terminal, the lysine-rich 3$_{10}$ helix and many of the loop regions between the helical structures were better analyzed by DSSO due to the higher abundance of lysine residues in these regions. Together, these results demonstrate that acidic residue cross-linking can provide complementary structural information to that obtained using amine-reactive cross-linkers.

In some embodiments, unlike myoglobin, DHSO and DSSO cross-linking of BSA have resulted in much more similar cross-linking profiles, meaning that similar interactions within BSA were identified (FIG. 6A and FIG. 6D). without being bound by any theory, this is most likely owing to the fact that BSA has more evenly dispersed distribution of lysine, aspartic acid, and glutamic acid residues throughout the protein sequence. Thus, complementary usage of DHSO and DSSO can strengthen the validity of the cross-links identified by any of the two reagents individually. More importantly, in some embodiments, this will generate complementary structural information to facilitate a more comprehensive understanding of protein structures.

EXAMPLES

The following Examples are non-limiting and other variants contemplated by one of ordinary skill in the art are included within the scope of this disclosure.

Example 1—Materials and Reagents

General chemicals were purchased from Fisher Scientific or VWR International. Bovine serum albumin (≥96% purity), myoglobin from equine heart (≥90% purity), and DMTMM (≥96% purity) were purchased from Sigma-Aldrich. Ac-SR8 peptide (Ac-SAKAYEHR (SEQ ID NO: 178), 98.22% purity) was custom ordered from Biomatik (Wilmington, Del.).

Example 2—Dihydrazide Sulfoxide (DHSO) Synthesis

Disuccinimidyl sulfoxide (DSSO) was synthesized as previously published[16]. The 2-step synthesis scheme for DHSO from DSSO is depicted in FIG. 1D. Briefly, tert-butyl carbazate (1.10 g, 8.32 mmol) was added to DSSO (1.41 g, 4.16 mmol) in dichloromethane (DCM) (50 mL). The resulting yellow solution was stirred at room temperature for 12 h, after which trifluoroacetic acid (2.20 mL, 28.7 mmol) was added. The resulting orange solution was stirred for 72 h before removing the solvent in vacuo. The resulting orange oil was dissolved in methanol, and then triethylamine was added. The resulting mixture was stirred for 20 min, after which a white solid had precipitated. The solid was collected via centrifuge, and then stirred with fresh methanol for 20 min. The solid was collected via centrifuge again, and this process of stirring with fresh methanol was repeated another two times. Drying the isolated white solid in vacuo afforded DHSO (0.375 g, 46%): mp 159-162° C.; $^1$H NMR (500 MHz, DMSO-d$_6$): δ 9.13 (s, 2H), 4.24 (s, 4H), 3.0-2.97 (m, 2H), 2.83-2.75 (m, 2H), 2.43 (t, J=7.5 Hz, 4H); $^{13}$C NMR (125 MHz, DMSO-d$_6$): δ 169.3, 46.7, 26.2; IR (thin film): 3308, 3044, 1631, 1449, 1297, 1032 cm$^{-1}$; HRMS (ESI) m/z calculated for C$_6$H$_{15}$N$_4$O$_3$S [M+H]+223.0865, found 223.0857.

Example 3—DHSO Cross-Linking of Synthetic Peptides

Synthetic peptide Ac-SR8 was dissolved in DMSO to 1 mM and cross-linked with DHSO in a 1:1 molar ratio of peptide to cross-linker in the presence of 1 equivalent of diisopropylethylamine and DMTMM. The resulting samples were diluted to 10 pmol/µL in 3% ACN/2% formic acid prior to MS$^n$ analysis.

Example 4—DHSO Cross-Linking of Equine Myoglobin and Bovine Serum Albumin

50 µL of 50 µM BSA or 200 µM myoglobin in PBS buffer (pH 7.4) was reacted with DHSO in molar ratios of 1:5, 1:10, 1:20, and 1:30. The cross-linking reaction was initiated by adding equivalent concentrations of DHSO and DMTMM to protein solutions, reacted for 1 h at room temperature.

Example 5—Digestion of DHSO Cross-Linked Proteins

Cross-linked protein samples were subjected to either SDS-PAGE followed by in-gel digestion, or directly digested in solution. For in-gel digestion, cross-linked proteins were separated by SDS-PAGE and visualized by Coomassie blue staining. The selected bands were excised, reduced with TCEP for 30 min, alkylated with iodoacetamide for 30 min in the dark, and then digested with trypsin at 37° C. overnight. Peptide digests were extracted, concentrated, and reconstituted in 3% ACN/2% formic acid for MS$^n$ analysis. For in-solution digestion, cross-linked proteins were first precipitated with TCA and then re-suspended in 8M urea buffer. Reduction and alkylation were performed prior to Lys-C/trypsin digestion as previously described[24]. The resulting digests were desalted using Waters C18 Sep-Pak cartridges and fractionated by peptide size exclusion chromatography (SEC) based on the protocol by Leitner et al.[25]. The fractions containing cross-linked peptides were collected for subsequent MS$^n$ analysis.

Example 6—Liquid Chromatography-Multistage Tandem Mass Spectrometry (LC MS$^n$) Analysis DHSO cross-linked peptides were analyzed by LC-MS$^n$ utilizing an Easy-nLC 1000 (Thermo Fisher, San Jose, Calif.) coupled on-line to an LTQ-Orbitrap XL mass spectrometer (Thermo Fisher, San Jose, Calif.) as previously described[16,17]. Each MS$^n$ experiment consists of one MS scan in FT mode (350-1400 m/z, resolution of 60,000 at m/z 400) followed by two data-dependent MS$^2$ scans in FT mode (resolution of 7500) with normalized collision energy at 10% on the top two MS peaks with charges 4+ or higher, and three MS$^3$ scans in the LTQ with normalized collision energy at 35% on the top three peaks from each MS$^2$.

Example 7—Data Analysis and Identification of DHSO Cross-Linked Peptides

Monoisotopic masses of parent ions and corresponding fragment ions, parent ion charge states, and ion intensities from MS$^2$ and MS$^3$ spectra were extracted using in-house software based on the Raw_Extract script from Xcalibur v2.4 (Thermo Scientific) as previously described[17]. MS$^3$ data was subjected to a developmental version of Protein Prospector (v.5.16.0) for database searching, using Batch-Tag against SwissProt.2014.12.4.random.concat databases limited to either the *Bos taurus* or *Equus caballus* taxonomy with mass tolerances for parent ions and fragment ions set as ±20 ppm and 0.6 Da, respectively. Trypsin was set as the enzyme with four maximum missed cleavages allowed. Cysteine carbamidomethylation was set as a constant modification. A maximum of four variable modifications were also allowed, including protein N-terminal acetylation, methionine oxidation, and N-terminal conversion of glutamine to pyroglutamic acid. In addition, three defined modifications representing cross-linker fragment moieties on aspartic acid and glutamic acid were selected: alkene (A, $C_3H_4N_2$, +68 Da), sulfenic acid (S, $C_3H_6N_2SO$, +118 Da), and unsaturated thiol (T, $C_3H_4N_2S$, +100 Da) modifications. Initial acceptance criteria for peptide identification required a reported expectation value ≤0.1. The in-house program XL-Discoverer, a revised version of previously developed Link-Hunter, was used to validate and summarize cross-linked peptides based on MS$^n$ data and database searching[16].

Example 8—Dissecting Structural Dynamics of Human COP9 Signalosome (CSN)

A novel approach to integration of multiplexed quantitation and different cross-linking chemistries for comprehensive structural comparison of protein complexes is provided. Cross-linking mass spectrometry (XL-MS) has become a powerful structural tool for elucidating architectures of protein complexes. Current XL-MS studies predominantly have used lysine targeting cross-linkers. However, there remains difficulty in characterizing interaction interfaces with limited lysine residues. Recently we developed an acidic residue targeting cross-linker, dihydrazide sulfoxide (DHSO)[16], enabling improved coverage of protein interactions. As protein complexes are dynamic entities, which require quantitative XL-MS strategies for comparative analysis. To improve throughput and quantitation accuracy, a QMIX (Quantitation of Multiplexed Isobaric labelled cross-linked (X) peptides) strategy[28] was developed for simultaneous comparison of multiple conformation states of protein complexes. The QMIX strategy was integrated with cross-linkers targeting different residues to dissect structural dynamics of human COP9 signalosome (CSN).

Two types of CSN complexes, CSN I and CSN II were purified, and cross-linked using DSSO or DHSO, respectively. The resulting cross-linked proteins were digested and cross-linked peptides were isolated using peptide SEC. Following SEC separation, selected fractions were labeled with TMT 6-plex™ isobaric Reagents (Thermo Scientific). The isobaric reagents labeled cross-linked peptides were mixed equally and analyzed by LC-MS$^n$ using an Easy-nLC 1200 (Thermo Scientific) coupled on-line to an Orbitrap Fusion Lumos Tribrid MS (Thermo Scientific). The resulting mass spectrometric data was subjected to protein database searching using Protein Prospector. Quantitation and cross-link identification was performed using in-house software package XL-Discoverer, designed to integrate various layers of MS$^n$ data to automatically summarize and validate the identification of cross-linking peptides.

CSN is a protein complex that functions as a deneddylase for cullin-RING ligases (CRLs) and thus modulates the assembly and action of CRLs. Although CSN is known to consist of eight subunits, a new stoichiometric subunit (i.e., CSN 9) has been recently identified[16] that can enhance the CSN activity. To determine the molecular details underlying composition-dependent activation and action mechanisms of the CSN complex, we have established a new integrated strategy combining a multiplexed QXL-MS strategy (QMIX28) and the two sulfoxide-containing MS-cleavable cross-linkers with diverse functional groups, DSSO[29] and DHSO[30]. The identification of cross-linked peptides is based on the XL-MS workflow designed for sulfoxide-containing MS-cleavable cross-linkers using multistage tandem mass spectrometry (MS$^n$)[28,16]. Initial results from our XL-MS studies have identified 22 inter-subunit interactions comprised of 160 inter-subunit linkages using DHSO, and 19 inter-subunit interactions comprised of 107 inter-subunit linkages using DSSO. Additionally, 150 DSSO and 215 DHSO intra-subunit linkages were identified. Mapping of the linkages the CSN crystal structure (4D10), revealed that 84% of DSSO intra-links and 89% of DHSO intralinks were <30 Å. The detection of violated cross-links suggests an alternative positioning or unexpected flexibility in parts of the CSN complex. Concurrent usage of lysine and acidic residue targeting cross-linkers, has allowed for both validation of complimentary identified regions as well as elucidated regions where either lysine or acidic resides are sparse. The results have provided new structural details for refining the CSN structure and understanding its action mechanisms. The technologies presented here can be easily adapted to study other protein complexes.

Perspectives

In some embodiments, provided herein is the development and characterization of a new acidic residue-targeting, sulfoxide-containing MS-cleavable cross-linker, dihydrazide sulfoxide (DHSO), which is a new derivative of inventors' previously developed amine-reactive MS-cleavable reagent, DSSO[16]. In some embodiments, the extensive analyses herein have proven that DHSO cross-linked peptides possesses the same characteristics distinctive to peptides cross-linked by other sulfoxide-containing amine reactive cross-linkers[16-18], thus enabling their simplified identification by MS$^n$ analysis. The unique features of DHSO will significantly facilitate cross-linking studies targeting acidic residues, which has been difficult in the past due to the large number of DIE present in protein sequences and complexity of their resulting cross-linked peptides for MS analysis.

Comparison of DHSO and DSSO cross-linking confirms the need of expanding the coverage of protein interactions using cross-linkers targeting different residues, especially when the distribution of specific amino acids is uneven. In some embodiments, this disclosure demonstrates the robustness and potential of the XL-MS technology based on sulfoxide-containing MS-cleavable cross-linkers and provides a viable analytical platform for the development of new MS-cleavable cross-linker derivatives to further define protein-protein interactions. Without being bound by any theory, it is believed that the development of these new tools will aid in the goal of understanding the structural dynamics of protein complexes and their mechanistic functions at the global scale in the future.

In some embodiments, the workflow disclosed herein will allow fast, effective, accurate and robust identification of DHSO cross-linked peptides. In some embodiments, the results herein demonstrate that DHSO cross-linked peptides possess the same characteristics distinctive to peptides cross-linked by other sulfoxide-containing amine reactive crosslinkers previously developed by the inventors, thus enabling their simplified identification by MS$^n$ analysis. The development of DHSO cross-linking will aid in the goal of defining protein-protein interactions at the global scale and understanding the structural dynamics of protein complexes and their mechanistic functions in cells.

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein.

In this application, the use of the singular includes the plural unless specifically stated otherwise. Also, the use of "comprise", "comprises", "comprising", "contain", "contains", "containing", "include", "includes", and "including" are not intended to be limiting.

As used in this specification and claims, the singular forms "a," "an" and "the" include plural references unless the content clearly dictates otherwise.

As used herein, "about" means a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

Although this disclosure is in the context of certain embodiments and examples, those skilled in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above.

Abbreviations

XL-MS: cross-linking mass spectrometry DSSO: disuccinimidyl sulfoxide

DMDSSO: dimethyl disuccinimidyl sulfoxide

Azide-A-DSBSO: Azide-tagged, Acid-cleavable DiSuccinimidyl BisSulfoxide

DHSO: dihydrazide sulfoxide, a.k.a. 3,3'-sulfinyldi(propanehydrazide)

MS: mass spectrometry

MS$^2$: tandem mass spectrometry

MS$^3$: third stage tandem mass spectrometry

MS$^n$: multi-stage tandem mass spectrometry

CID: collisional induced dissociation

LC MS$^n$: liquid chromatography multistage tandem mass spectrometry

Asp: aspartic acid

Glu: glutamic acid

REFERENCES

All references cited in this disclosure are incorporated herein by reference in their entireties.

(1) Sinz, A. *Mass Spectrom Rev* 2006, 25, 663-682.
(2) Walzthoeni, T.; Leitner, A.; Stengel, F.; Aebersold, R. *Curr Opin Struct Biol* 2013, 23, 252-260.
(3) Chen, Z. A.; Jawhari, A.; Fischer, L.; Buchen, C.; Tahir, S.; Kamenski, T.; Rasmussen, M.; Lariviere, L.;

Bukowski-Wills, J. C.; Nilges, M.; Cramer, P.; Rappsilber, J. *EMBO J* 2010, 29, 717-726.

(4) Herzog, F.; Kahraman, A.; Boehringer, D.; Mak, R.; Bracher, A.; Walzthoeni, T.; Leitner, A.; Beck, M.; Hartl, F. U.; Ban, N.; Malmstrom, L.; Aebersold, R. *Science* 2012, 337, 1348-1352.

(5) Kao, A.; Randall, A.; Yang, Y.; Patel, V. R.; Kandur, W.; Guan, S.; Rychnovsky, S. D.; Baldi, P.; Huang, L. *Mol Cell Proteomics* 2012, 11, 1566-1577.

(6) Erzberger, J. P.; Stengel, F.; Pellarin, R.; Zhang, S.; Schaefer, T.; Aylett, C. H.; Cimermancic, P.; Boehringer, D.; Sali, A.; Aebersold, R.; Ban, N. *Cell* 2014, 158, 1123-1135.

(7) Shi, Y.; Fernandez-Martinez, J.; Tjioe, E.; Pellarin, R.; Kim, S. J.; Williams, R.; Schneidman, D.; Sali, A.; Rout, M. P.; Chait, B. T. *Mol Cell Proteomics* 2014, 13, 2927-2943.

(8) Zeng-Elmore, X.; Gao, X. Z.; Pellarin, R.; Schneidman-Duhovny, D.; Zhang, X. J.; Kozacka, K. A.; Tang, Y.; Sali, A.; Chalkley, R. J.; Cote, R. H.; Chu, F. *J Mol Biol* 2014.

(9) Liu, J.; Yu, C.; Hu, X.; Kim, J. K.; Bierma, J. C.; Jun, H. I.; Rychnovsky, S. D.; Huang, L.; Qiao, F. *Cell reports* 2015, 12, 2169-2180.

(10) Yang, L.; Tang, X.; Weisbrod, C.; Munske, G.; Eng, J.; von Haller, P.; Kaiser, N.; Bruce, J. *Analytical Chemistry* 2010, 663-682.

(11) Kasper, P. T.; Back, J. W.; Vitale, M.; Hartog, A. F.; Roseboom, W.; de Koning, L. J.; van Maarseveen, J. H.; Muijsers, A. O.; de Koster, C. G.; de Jong, L. *Chembiochem* 2007, 8, 1281-1292.

(12) Lu, Y.; Tanasova, M.; Borhan, B.; Reid, G. E. *Anal Chem* 2008, 80, 9279-9287.

(13) Zhang, H.; Tang, X.; Munske, G. R.; Tolic, N.; Anderson, G. A.; Bruce, J. E. *Mol Cell Proteomics* 2009, 8, 409-420.

(14) Muller, M. Q.; Dreiocker, F.; Ihling, C. H.; Schafer, M.; Sinz, A. *Anal Chem* 2010, 82, 6958-6968.

(15) Petrotchenko, E. V.; Serpa, J. J.; Borchers, C. H. *Mol Cell Proteomics* 2011, 10, M110.001420.

(16) Kao, A.; Chiu, C. L.; Vellucci, D.; Yang, Y.; Patel, V. R.; Guan, S.; Randall, A.; Baldi, P.; Rychnovsky, S. D.; Huang, L. *Mol Cell Proteomics* 2011, 10, M110.002212.

(17) Yu, C.; Kandur, W.; Kao, A.; Rychnovsky, S.; Huang, L. *Anal Chem* 2014, 86, 2099-2106.

(18) Kaake, R. M.; Wang, X.; Burke, A.; Yu, C.; Kandur, W.; Yang, Y.; Novtisky, E. J.; Second, T.; Duan, J.; Kao, A.; Guan, S.; Vellucci, D.; Rychnovsky, S. D.; Huang, L. *Mol Cell Proteomics* 2014, 13, 3533-3543.

(19) Yu, C.; Mao, H.; Novitsky, E. J.; Tang, X.; Rychnovsky, S. D.; Zheng, N.; Huang, L. *Nature communications* 2015, 6, 10053.

(20) Belsom, A.; Schneider, M.; Fischer, L.; Brock, O.; Rappsilber, J. *Mol Cell Proteomics* 2016, 15, 1105-1116.

(21) Apweiler, R., et al.; UniProt Consortium *Nucleic Acids Res* 2013, 41, D43-47.

(22) Leitner, A.; Joachimiak, L. A.; Unverdorben, P.; Walzthoeni, T.; Frydman, J.; Forster, F.; Aebersold, R. *Proc Natl Acad Sci USA* 2014, 111, 9455-9460.

(23) Novak, P.; Kruppa, G. H. Eur *J Mass Spectrom* (Chichester, Eng) 2008, 14, 355-365.

(24) Wang, X.; Chen, C. F.; Baker, P. R.; Chen, P. L.; Kaiser, P.; Huang, L. *Biochemistry* 2007, 46, 3553-3565.

(25) Leitner, A.; Walzthoeni, T.; Aebersold, R. *Nat Protoc* 2014, 9, 120-137.

(26) Schilling, B.; Row, R. H.; Gibson, B. W.; Guo, X.; Young, M. M. *J Am Soc Mass Spectrom.* 2003, 14, 834-850.

(27) Liu, F.; Rijkers, D. T.; Post, H.; Heck, A. J. Nat. Methods 2015, 12, 1179-1184.

(28) Craig B. Gutierrez, et al., Developing an Acidic Residue Reactive and Sulfoxide-Containing MS-Cleavable Homobifunctional Cross-Linker for Probing Protein-Protein Interactions, Anal. Chem. 2016, 88, 8315-8322.

(29) Yu, C. et al, Anal. Chem, 2016.

(30) Rozen, S. et al, Cell Reports, 2015.

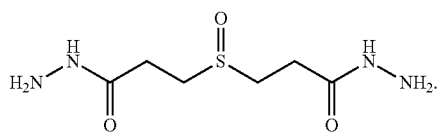 [SMILES: NNC(=O)CCS(=O)CCC(=O)NN]

What is claimed is:

1. An MS-cleavable cross-linker consisting of:
two hydrazide reactive groups;
a spacer arm with one central sulfoxide group, wherein the one central sulfoxide group is linked to each of the two hydrazide reactive groups through two methylene groups and a carbonyl group; and
two symmetric collision-induced dissociation (CID) cleavable bonds on the spacer arm, wherein each of the two CID cleavable bonds is a C—S bond adjacent to the one central sulfoxide group, and wherein the MS-cleavable cross-linker is configured for mapping intra-protein interactions in a protein, or inter-protein interactions in a protein complex, or combinations thereof.

2. The MS-cleavable cross-linker of claim 1, wherein each of the two hydrazide reactive group is configured to react with an activated acidic side chain in the protein or protein complex.

3. The MS-cleavable cross-linker of claim 1, wherein the MS-cleavable crosslinker is dihydrazide sulfoxide (DHSO), having the structure:

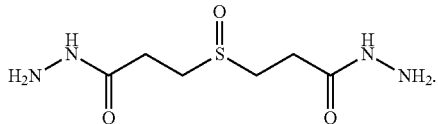 [SMILES: NNC(=O)CCS(=O)CCC(=O)NN]

4. The MS-cleavable cross-linker of claim 3, wherein the two hydrazide reactive groups are separated by a 12.5 Å long spacer arm consisting of the two symmetrical CID cleavable C—S flanking the one sulfoxide group.

5. A method for synthesis of an MS-cleavable cross-linker according to claim 1 comprising the steps of:
(i) providing disuccinimidyl sulfoxide (DSSO) in dichlormethane;
(ii) adding tert-butyl carbazate to derive a first solution;
(iii) stirring the first solution of step (ii);
(iv) adding trifluoroacetic acid to derive an second solution;
(v) stirring the second solution of step (iv);
(vi) removing solvent from the second solution of step (v) in vacuo to derive an oil;
(vii) dissolving the oil from step (vi) in methanol and adding trimethylamine to obtain a mixture;
(viii) stirring the mixture from step (vii) to obtain a precipitate;
(ix) collecting the precipitate from step (viii), washing the precipitate in fresh methanol, and drying the precipitate in vacuo, thereby obtaining the MS-cleavable cross-linker according to claim 1.

6. The method of claim 5, wherein stirring the first solution of step (ii) is performed at room temperature.

7. The method of claim 6, wherein stirring the first solution of step (ii) is performed for about 6 h to about 24 h.

8. The method of claim 5, wherein stirring the second solution of step (iv) is performed at room temperature.

9. The method of claim 8, wherein stirring the second solution of step (iv) is performed for about 36 h to about 144 h.

10. The method of claim 5, wherein stirring the mixture is performed at room temperature.

11. The method of claim 10, wherein stirring the mixture is performed for about 10 min to about 40 min.

12. The method of claim 5, wherein collecting the precipitate from step (viii), washing the precipitate in fresh methanol is performed about 1 to about 10 times.

13. The method of claim 5, wherein the MS-cleavable cross-linker is DHSO, having the structure:

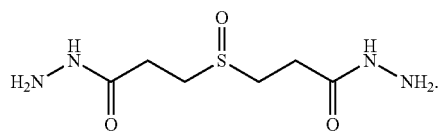 [SMILES: NNC(=O)CCS(=O)CCC(=O)NN]

14. A method for mapping intra-protein interactions in a protein, inter-protein interactions in a protein complex, or combinations thereof, the method comprising:
providing 4-(4,6-dimethoxy-1,3,5-triazin-2-yl)-4-methyl-morpholinium chloride (DMTMM) as an activating agent;
activating at least one acidic residue by DMTMM in the protein or protein complex;
providing an MS-cleavable cross-linker according to claim 1,
cross-linking the MS-cleavable cross-linker to the at least one activated acidic residue in the protein or protein complex;
digesting with an enzyme the protein or protein complex cross-linked to the MS-cleavable cross-linker;
generating one or more peptide fragments of the protein or protein complex, wherein the one or more peptide fragments are chemically cross-linked to the MS-cleavable cross-linker; and
identifying the one or more peptide fragments using tandem mass spectrometry ($MS^n$),
thereby mapping intra-protein interactions in the protein and/or inter-protein interactions in the protein complex.

15. The method of claim 14, wherein the MS-cleavable cross-linker is DHSO, having the structure

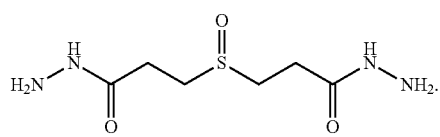

16. A method for cross-linking mass spectrometry (XL-MS) for identifying one or more cross-linked peptides, the method comprising:

providing 4-(4,6-dimethoxy-1,3,5-triazin-2-yl)-4-methyl-morpholinium chloride (DMTMM) as an activating agent;
activating at least one acidic residue by DMTMM in a protein or a protein complex;
providing an MS-cleavable cross-linker according to claim 1,
cross-linking the MS-cleavable cross-linker to the at least one activated acidic residue in the protein or protein complex;
digesting with an enzyme the protein or protein complex cross-linked to the MS-cleavable cross-linker;
generating one or more peptide fragments of the protein or protein complex, wherein the one or more peptide fragments are chemically cross-linked to the MS-cleavable cross-linker;
performing a liquid chromatography-tandem mass spectrometry (LC-MS$^n$) analysis on the one or more cross-linked peptides, wherein the LC-MS$^n$ analysis comprises:
detecting the one or more cross-linked peptides by MS$^1$ analysis;
selecting the one or more cross-linked peptides detected by MS$^1$ for MS$^2$ analysis;
selectively fragmenting the at least one CID cleavable bond and separating the one or more cross-linked peptides during MS$^2$ analysis;
sequencing the one or more cross-linked peptides separated during MS$^2$ analysis by MS$^3$ analysis; and
integrating data obtained during MS$^1$, MS$^2$ and MS$^3$ analyses to identify the one or more cross-linked peptides.

17. The method of claim 16, wherein the MS-cleavable cross-linker is DHSO, having the structure

SEQUENCE LISTING

```
<160> NUMBER OF SEQ ID NOS: 190

<210> SEQ ID NO 1
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Unsaturated thiol moiety at Glu 3

<400> SEQUENCE: 1

Ala Leu Glu Leu Phe Arg
1               5

<210> SEQ ID NO 2
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene moiety at Glu 3
```

```
<400> SEQUENCE: 2

Ala Leu Glu Leu Phe Arg
1               5

<210> SEQ ID NO 3
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Asp 4
<220> FEATURE:
<221> NAME/KEY: MISC_FEATURE
<222> LOCATION: (13)..(13)
<223> OTHER INFORMATION: Oxidation at Met 13

<400> SEQUENCE: 3

His Pro Gly Asp Phe Gly Ala Asp Ala Gln Gly Ala Met Thr Lys
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Asp 8
<220> FEATURE:
<221> NAME/KEY: MISC_FEATURE
<222> LOCATION: (13)..(13)
<223> OTHER INFORMATION: Oxidation at Met 13

<400> SEQUENCE: 4

His Pro Gly Asp Phe Gly Ala Asp Ala Gln Gly Ala Met Thr Lys
1               5                   10                  15

<210> SEQ ID NO 5
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Alkene moiety at Asp 8

<400> SEQUENCE: 5

His Pro Gly Asp Phe Gly Ala Asp Ala Gln Gly Ala Met Thr Lys
1               5                   10                  15

<210> SEQ ID NO 6
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Unsaturated thiol moiety at Asp 8
```

```
<400> SEQUENCE: 6

His Pro Gly Asp Phe Gly Ala Asp Ala Gln Gly Ala Met Thr Lys
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Asp 4

<400> SEQUENCE: 7

His Pro Gly Asp Phe Gly Ala Asp Ala Gln Gly Ala Met Thr Lys
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Unsaturated thiol moiety at Asp 4

<400> SEQUENCE: 8

His Pro Gly Asp Phe Gly Ala Asp Ala Gln Gly Ala Met Thr Lys
1               5                   10                  15

<210> SEQ ID NO 9
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene moiety at Glu 6

<400> SEQUENCE: 9

Lys Lys Gly His His Glu Ala Glu Leu Lys Pro Leu Ala Gln Ser His
1               5                   10                  15

Ala Thr Lys

<210> SEQ ID NO 10
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Alkene moiety at Glu 8

<400> SEQUENCE: 10

Lys Lys Gly His His Glu Ala Glu Leu Lys Pro Leu Ala Gln Ser His
1               5                   10                  15

Ala Thr Lys

<210> SEQ ID NO 11
```

```
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene moiety at Lys 1
<220> FEATURE:
<221> NAME/KEY: MISC_FEATURE
<222> LOCATION: (2)..(2)
<223> OTHER INFORMATION: Unsaturated thiol moiety at Lys 2
<220> FEATURE:
<221> NAME/KEY: MISC_FEATURE
<222> LOCATION: (10)..(10)
<223> OTHER INFORMATION: Alkene moiety at Lys 10

<400> SEQUENCE: 11

Lys Lys Gly His His Glu Ala Glu Leu Lys Pro Leu Ala Gln Ser His
1               5                   10                  15

Ala Thr Lys

<210> SEQ ID NO 12
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Unsaturated thiol moiety at Lys 2

<400> SEQUENCE: 12

Lys Lys Gly His His Glu Ala Glu Leu Lys Pro Leu Ala Gln Ser His
1               5                   10                  15

Ala Thr Lys

<210> SEQ ID NO 13
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Unsaturated thiol moiety at Lys 10

<400> SEQUENCE: 13

Lys Lys Gly His His Glu Ala Glu Leu Lys Pro Leu Ala Gln Ser His
1               5                   10                  15

Ala Thr Lys

<210> SEQ ID NO 14
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene moiety at Glu 1

<400> SEQUENCE: 14

Glu Leu Gly Phe Gln Gly
1               5
```

```
<210> SEQ ID NO 15
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Unsaturated thiol moiety at Glu 10

<400> SEQUENCE: 15

Leu Phe Thr Gly His Pro Glu Thr Leu Glu Lys
1               5                   10

<210> SEQ ID NO 16
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene moiety at Glu 7

<400> SEQUENCE: 16

Leu Phe Thr Gly His Pro Glu Thr Leu Glu Lys
1               5                   10

<210> SEQ ID NO 17
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Alkene moiety at Glu 10

<400> SEQUENCE: 17

Leu Phe Thr Gly His Pro Glu Thr Leu Glu Lys
1               5                   10

<210> SEQ ID NO 18
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Unsaturated thiol moiety at Glu 7

<400> SEQUENCE: 18

Leu Phe Thr Gly His Pro Glu Thr Leu Glu Lys
1               5                   10

<210> SEQ ID NO 19
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
```

```
<223> OTHER INFORMATION: Alkene moiety at Glu 2
<220> FEATURE:
<221> NAME/KEY: MISC_FEATURE
<222> LOCATION: (5)..(5)
<223> OTHER INFORMATION: Oxidation at Met 5

<400> SEQUENCE: 19

Thr Glu Ala Glu Met Lys
1               5

<210> SEQ ID NO 20
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Glu 4
<220> FEATURE:
<221> NAME/KEY: MISC_FEATURE
<222> LOCATION: (5)..(5)
<223> OTHER INFORMATION: Oxidation at Met 5

<400> SEQUENCE: 20

Thr Glu Ala Glu Met Lys
1               5

<210> SEQ ID NO 21
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene moiety at Glu 2

<400> SEQUENCE: 21

Thr Glu Ala Glu Met Lys
1               5

<210> SEQ ID NO 22
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Glu 4

<400> SEQUENCE: 22

Thr Glu Ala Glu Met Lys
1               5

<210> SEQ ID NO 23
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Unsaturated thiol moiety at Glu 2

<400> SEQUENCE: 23
```

```
Thr Glu Ala Glu Met Lys
1               5

<210> SEQ ID NO 24
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Unsaturated thiol moiety at Glu 3

<400> SEQUENCE: 24

Ala Ser Glu Asp Leu Lys
1               5

<210> SEQ ID NO 25
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Unsaturated thiol moiety at Asp 4

<400> SEQUENCE: 25

Ala Ser Glu Asp Leu Lys
1               5

<210> SEQ ID NO 26
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene moiety at Glu 3

<400> SEQUENCE: 26

Ala Ser Glu Asp Leu Lys
1               5

<210> SEQ ID NO 27
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Unsaturated thiol moiety at Glu 11

<400> SEQUENCE: 27

Val Glu Ala Asp Ile Ala Gly His Gly Gln Glu Val Leu Ile Arg
1               5                   10                  15

<210> SEQ ID NO 28
<211> LENGTH: 15
<212> TYPE: PRT
<213> ORGANISM: Artificial
<220> FEATURE:
<223> OTHER INFORMATION: Synthetic
```

-continued

```
<220> FEATURE:
<221> NAME/KEY: MISC_FEATURE
<222> LOCATION: (2)..(2)
<223> OTHER INFORMATION: Alkene moiety at Glu 2

<400> SEQUENCE: 28

Val Glu Ala Asp Ile Ala Gly His Gly Gln Glu Val Leu Ile Arg
1               5                   10                  15

<210> SEQ ID NO 29
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Asp 4

<400> SEQUENCE: 29

Val Glu Ala Asp Ile Ala Gly His Gly Gln Glu Val Leu Ile Arg
1               5                   10                  15

<210> SEQ ID NO 30
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Unsaturated thiol moiety at Asp 4

<400> SEQUENCE: 30

Val Glu Ala Asp Ile Ala Gly His Gly Gln Glu Val Leu Ile Arg
1               5                   10                  15

<210> SEQ ID NO 31
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Unsaturated thiol moiety at Asp 7

<400> SEQUENCE: 31

Tyr Leu Glu Phe Ile Ser Asp Ala Ile Ile His Val Leu His Ser Lys
1               5                   10                  15

<210> SEQ ID NO 32
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene moiety at Glu 3

<400> SEQUENCE: 32

Tyr Leu Glu Phe Ile Ser Asp Ala Ile Ile His Val Leu His Ser Lys
1               5                   10                  15
```

```
<210> SEQ ID NO 33
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Unsaturated thiol moiety at Glu 3

<400> SEQUENCE: 33

Tyr Leu Glu Phe Ile Ser Asp Ala Ile Ile His Val Leu His Ser Lys
1               5                   10                  15

<210> SEQ ID NO 34
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene moiety at Glu 2

<400> SEQUENCE: 34

Ala Glu Phe Val Glu Val Thr Lys
1               5

<210> SEQ ID NO 35
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Unsaturated thiol moiety at Glu 5

<400> SEQUENCE: 35

Ala Glu Phe Val Glu Val Thr Lys
1               5

<210> SEQ ID NO 36
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene moiety at Glu 5

<400> SEQUENCE: 36

Ala Glu Phe Val Glu Val Thr Lys
1               5

<210> SEQ ID NO 37
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Asp 4
```

```
<400> SEQUENCE: 37

Leu Val Thr Asp Leu Thr Lys
1               5

<210> SEQ ID NO 38
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Unsaturated thiol moiety at Asp 4

<400> SEQUENCE: 38

Leu Val Thr Asp Leu Thr Lys
1               5

<210> SEQ ID NO 39
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Unsaturated thiol moiety at Glu 7

<400> SEQUENCE: 39

Gln Asn Cys Asp Gln Phe Glu Lys
1               5

<210> SEQ ID NO 40
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene moiety at Glu 7

<400> SEQUENCE: 40

Gln Asn Cys Asp Gln Phe Glu Lys
1               5

<210> SEQ ID NO 41
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Unsaturated thiol moiety at Glu 7

<400> SEQUENCE: 41

Gln Asn Cys Asp Gln Phe Glu Lys
1               5

<210> SEQ ID NO 42
<211> LENGTH: 8
<212> TYPE: PRT
<213> ORGANISM: Artificial
<220> FEATURE:
```

```
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Asp 4

<400> SEQUENCE: 42

Gln Asn Cys Asp Gln Phe Glu Lys
1               5

<210> SEQ ID NO 43
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Unsaturated thiol moiety at Asp 7

<400> SEQUENCE: 43

Tyr Ile Cys Asp Asn Gln Asp Thr Ile Ser Ser Lys
1               5                   10

<210> SEQ ID NO 44
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Unsaturated thiol moiety at Asp 4

<400> SEQUENCE: 44

Tyr Ile Cys Asp Asn Gln Asp Thr Ile Ser Ser Lys
1               5                   10

<210> SEQ ID NO 45
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene moiety at Asp 7

<400> SEQUENCE: 45

Tyr Ile Cys Asp Asn Gln Asp Thr Ile Ser Ser Lys
1               5                   10

<210> SEQ ID NO 46
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene moiety at Glu 3

<400> SEQUENCE: 46

Ala Thr Glu Glu Gln Leu Lys
1               5
```

```
<210> SEQ ID NO 47
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Glu 4

<400> SEQUENCE: 47

Ala Thr Glu Glu Gln Leu Lys
1               5

<210> SEQ ID NO 48
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Oxidation at Met 3
<220> FEATURE:
<221> NAME/KEY: MISC_FEATURE
<222> LOCATION: (4)..(4)
<223> OTHER INFORMATION: Unsaturated thiol moiety at Glu 4

<400> SEQUENCE: 48

Thr Val Met Glu Asn Phe Val Ala Phe Val Asp Lys
1               5                   10

<210> SEQ ID NO 49
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Unsaturated thiol moiety at Glu 4

<400> SEQUENCE: 49

Thr Val Met Glu Asn Phe Val Ala Phe Val Asp Lys
1               5                   10

<210> SEQ ID NO 50
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Unsaturated thiol moiety at Asp 1

<400> SEQUENCE: 50

Asp Thr His Lys Ser Glu Ile Ala His Arg
1               5                   10

<210> SEQ ID NO 51
<211> LENGTH: 10
<212> TYPE: PRT
<213> ORGANISM: Artificial
<220> FEATURE:
<223> OTHER INFORMATION: Synthetic
```

```
<220> FEATURE:
<221> NAME/KEY: MISC_FEATURE
<222> LOCATION: (6)..(6)
<223> OTHER INFORMATION: Unsaturated thiol moiety at Glu 6

<400> SEQUENCE: 51

Asp Thr His Lys Ser Glu Ile Ala His Arg
1               5                   10

<210> SEQ ID NO 52
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene moiety at Asp 1

<400> SEQUENCE: 52

Asp Thr His Lys Ser Glu Ile Ala His Arg
1               5                   10

<210> SEQ ID NO 53
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Lys 4

<400> SEQUENCE: 53

Asp Thr His Lys Ser Glu Ile Ala His Arg
1               5                   10

<210> SEQ ID NO 54
<211> LENGTH: 22
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: Alkene moiety at Asp 15

<400> SEQUENCE: 54

Val His Lys Glu Cys Cys His Gly Asp Leu Leu Glu Cys Ala Asp Asp
1               5                   10                  15

Arg Ala Asp Leu Ala Lys
            20

<210> SEQ ID NO 55
<211> LENGTH: 22
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: Alkene moiety at Asp 16

<400> SEQUENCE: 55

Val His Lys Glu Cys Cys His Gly Asp Leu Leu Glu Cys Ala Asp Asp
```

```
1               5                   10                  15
```

Arg Ala Asp Leu Ala Lys
            20

<210> SEQ ID NO 56
<211> LENGTH: 22
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: Alkene moiety at Asp 19

<400> SEQUENCE: 56

Val His Lys Glu Cys Cys His Gly Asp Leu Leu Glu Cys Ala Asp Asp
1               5                   10                  15

Arg Ala Asp Leu Ala Lys
            20

<210> SEQ ID NO 57
<211> LENGTH: 22
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: Alkene moiety at Asp 19

<400> SEQUENCE: 57

Val His Lys Glu Cys Cys His Gly Asp Leu Leu Glu Cys Ala Asp Asp
1               5                   10                  15

Arg Ala Asp Leu Ala Lys
            20

<210> SEQ ID NO 58
<211> LENGTH: 22
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Unsaturated thiol moiety at Lys 3

<400> SEQUENCE: 58

Val His Lys Glu Cys Cys His Gly Asp Leu Leu Glu Cys Ala Asp Asp
1               5                   10                  15

Arg Ala Asp Leu Ala Lys
            20

<210> SEQ ID NO 59
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene moiety at Asp 5

<400> SEQUENCE: 59

Thr Cys Val Ala Asp Glu Ser His Ala Gly Cys Glu Lys
1               5                   10

<210> SEQ ID NO 60
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene moiety at Glu 6

<400> SEQUENCE: 60

Thr Cys Val Ala Asp Glu Ser His Ala Gly Cys Glu Lys
1               5                   10

<210> SEQ ID NO 61
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Alkene moiety at Glu 12

<400> SEQUENCE: 61

Thr Cys Val Ala Asp Glu Ser His Ala Gly Cys Glu Lys
1               5                   10

<210> SEQ ID NO 62
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Unsaturated thiol moiety at Glu 5

<400> SEQUENCE: 62

Asp Leu Gly Glu Glu His Phe Lys
1               5

<210> SEQ ID NO 63
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene moiety at Glu 3

<400> SEQUENCE: 63

Ala Asp Glu Lys Lys
1               5

<210> SEQ ID NO 64
<211> LENGTH: 21
<212> TYPE: PRT
<213> ORGANISM: Artificial
<220> FEATURE:
<223> OTHER INFORMATION: Synthetic
<220> FEATURE:

```
<221> NAME/KEY: MISC_FEATURE
<222> LOCATION: (17)..(17)
<223> OTHER INFORMATION: Alkene moiety at Asp 17

<400> SEQUENCE: 64

Gly Leu Val Leu Ile Ala Phe Ser Gln Tyr Leu Gln Gln Cys Pro Phe
1               5                   10                  15

Asp Glu His Val Lys
            20

<210> SEQ ID NO 65
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Unsaturated thiol moiety at Glu 4

<400> SEQUENCE: 65

Tyr Leu Tyr Glu Ile Ala Arg
1               5

<210> SEQ ID NO 66
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Glu 4

<400> SEQUENCE: 66

Tyr Leu Tyr Glu Ile Ala Arg
1               5

<210> SEQ ID NO 67
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Unsaturated thiol moiety at Asp 4

<400> SEQUENCE: 67

His Leu Val Asp Glu Pro Gln Asn Leu Ile Lys
1               5                   10

<210> SEQ ID NO 68
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Asp 4

<400> SEQUENCE: 68

His Leu Val Asp Glu Pro Gln Asn Leu Ile Lys
1               5                   10
```

```
<210> SEQ ID NO 69
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Alkene moiety at Glu 5

<400> SEQUENCE: 69

His Leu Val Asp Glu Pro Gln Asn Leu Ile Lys
1               5                   10

<210> SEQ ID NO 70
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene moiety at Glu 6

<400> SEQUENCE: 70

Cys Cys Thr Lys Pro Glu Ser Glu Arg
1               5

<210> SEQ ID NO 71
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Alkene moiety at Glu 8

<400> SEQUENCE: 71

Cys Cys Thr Lys Pro Glu Ser Glu Arg
1               5

<210> SEQ ID NO 72
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Unsaturated thiol moiety at Glu 8

<400> SEQUENCE: 72

Cys Cys Thr Lys Pro Glu Ser Glu Arg
1               5

<210> SEQ ID NO 73
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
```

<223> OTHER INFORMATION: Unsaturated thiol moiety at Glu 6

<400> SEQUENCE: 73

Cys Cys Thr Lys Pro Glu Ser Glu Arg
1               5

<210> SEQ ID NO 74
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Unsaturated thiol moiety at Lys 4

<400> SEQUENCE: 74

Cys Cys Thr Lys Pro Glu Ser Glu Arg
1               5

<210> SEQ ID NO 75
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene moiety at Glu 2

<400> SEQUENCE: 75

Ile Glu Thr Met Arg
1               5

<210> SEQ ID NO 76
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Unsaturated thiol moiety at Glu 3

<400> SEQUENCE: 76

Leu Gly Glu Tyr Gly Phe Gln Asn Ala Leu Ile Val Arg
1               5                   10

<210> SEQ ID NO 77
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene moiety at Glu 3

<400> SEQUENCE: 77

Leu Gly Glu Tyr Gly Phe Gln Asn Ala Leu Ile Val Arg
1               5                   10

<210> SEQ ID NO 78
<211> LENGTH: 14
<212> TYPE: PRT

```
<213> ORGANISM: Artificial
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Unsaturated thiol moiety at Glu 11

<400> SEQUENCE: 78

Val Pro Gln Val Ser Thr Pro Thr Leu Val Glu Val Ser Arg
1               5                   10

<210> SEQ ID NO 79
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Unsaturated thiol moiety at Glu 11

<400> SEQUENCE: 79

Leu Lys Pro Asp Pro Asn Thr Leu Cys Asp Glu Phe Lys
1               5                   10

<210> SEQ ID NO 80
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Unsaturated thiol moiety at Lys 2

<400> SEQUENCE: 80

Leu Lys Pro Asp Pro Asn Thr Leu Cys Asp Glu Phe Lys
1               5                   10

<210> SEQ ID NO 81
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: Unsaturated thiol moiety at Asp 15

<400> SEQUENCE: 81

Leu Lys Pro Asp Pro Asn Thr Leu Cys Asp Glu Phe Lys Ala Asp Glu
1               5                   10                  15

Lys

<210> SEQ ID NO 82
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: Unsaturated thiol moiety at Glu 16

<400> SEQUENCE: 82
```

Leu Lys Pro Asp Pro Asn Thr Leu Cys Asp Glu Phe Lys Ala Asp Glu
1               5                   10                  15

Lys

<210> SEQ ID NO 83
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene moiety at Glu 3

<400> SEQUENCE: 83

Leu Lys Glu Cys Cys Asp Lys Pro Leu Leu Glu Lys
1               5                   10

<210> SEQ ID NO 84
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene moiety at Asp 6

<400> SEQUENCE: 84

Leu Lys Glu Cys Cys Asp Lys Pro Leu Leu Glu Lys
1               5                   10

<210> SEQ ID NO 85
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Unsaturated thiol moiety at Glu 3

<400> SEQUENCE: 85

Leu Lys Glu Cys Cys Asp Lys Pro Leu Leu Glu Lys
1               5                   10

<210> SEQ ID NO 86
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Unsaturated thiol moiety at Asp 6

<400> SEQUENCE: 86

Leu Lys Glu Cys Cys Asp Lys Pro Leu Leu Glu Lys
1               5                   10

<210> SEQ ID NO 87
<211> LENGTH: 12
<212> TYPE: PRT
<213> ORGANISM: Artificial

```
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene moiety at Lys 2

<400> SEQUENCE: 87

Leu Lys Glu Cys Cys Asp Lys Pro Leu Leu Glu Lys
1               5                   10

<210> SEQ ID NO 88
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Unsaturated thiol moiety at Glu 8

<400> SEQUENCE: 88

Ser His Cys Ile Ala Glu Val Glu Lys
1               5

<210> SEQ ID NO 89
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene moiety at Glu 6

<400> SEQUENCE: 89

Ser His Cys Ile Ala Glu Val Glu Lys
1               5

<210> SEQ ID NO 90
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Alkene moiety at Glu 8

<400> SEQUENCE: 90

Ser His Cys Ile Ala Glu Val Glu Lys
1               5

<210> SEQ ID NO 91
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Unsaturated thiol moiety at Glu 6

<400> SEQUENCE: 91

Ser His Cys Ile Ala Glu Val Glu Lys
1               5
```

```
<210> SEQ ID NO 92
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Glu 4

<400> SEQUENCE: 92

Asn Tyr Gln Glu Ala Lys
1               5

<210> SEQ ID NO 93
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Unsaturated thiol moiety at Asp 6

<400> SEQUENCE: 93

Leu Lys His Leu Val Asp Glu Pro Gln Asn Leu Ile Lys
1               5                   10

<210> SEQ ID NO 94
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Unsaturated thiol moiety at Glu 7

<400> SEQUENCE: 94

Leu Lys His Leu Val Asp Glu Pro Gln Asn Leu Ile Lys
1               5                   10

<210> SEQ ID NO 95
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Unsaturated thiol moiety at Lys 2

<400> SEQUENCE: 95

Leu Lys His Leu Val Asp Glu Pro Gln Asn Leu Ile Lys
1               5                   10

<210> SEQ ID NO 96
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
```

```
<223> OTHER INFORMATION: Unsaturated thiol moiety at Glu 6

<400> SEQUENCE: 96

Leu Cys Val Leu His Glu Lys
1               5

<210> SEQ ID NO 97
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Unsaturated thiol moiety at Glu 5

<400> SEQUENCE: 97

Thr Pro Val Ser Glu Lys Val Thr Lys
1               5

<210> SEQ ID NO 98
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Unsaturated thiol moiety at Lys 6

<400> SEQUENCE: 98

Thr Pro Val Ser Glu Lys Val Thr Lys
1               5

<210> SEQ ID NO 99
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene moiety at Lys 6

<400> SEQUENCE: 99

Thr Pro Val Ser Glu Lys Val Thr Lys
1               5

<210> SEQ ID NO 100
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Glu 4

<400> SEQUENCE: 100

Leu Val Asn Glu Leu Thr Glu Phe Ala Lys
1               5                   10

<210> SEQ ID NO 101
<211> LENGTH: 10
<212> TYPE: PRT
```

```
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene moiety at Glu 7

<400> SEQUENCE: 101

Leu Val Asn Glu Leu Thr Glu Phe Ala Lys
1               5                   10

<210> SEQ ID NO 102
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Alkene moiety at Glu 9

<400> SEQUENCE: 102

Ser Leu His Thr Leu Phe Gly Asp Glu Leu Cys Lys
1               5                   10

<210> SEQ ID NO 103
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Unsaturated thiol moiety at Asp 8

<400> SEQUENCE: 103

Ser Leu His Thr Leu Phe Gly Asp Glu Leu Cys Lys
1               5                   10

<210> SEQ ID NO 104
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Unsaturated thiol moiety at Glu 9

<400> SEQUENCE: 104

Ser Leu His Thr Leu Phe Gly Asp Glu Leu Cys Lys
1               5                   10

<210> SEQ ID NO 105
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: Alkene moiety at Asp 13

<400> SEQUENCE: 105

Asn Glu Cys Phe Leu Ser His Lys Asp Asp Ser Pro Asp Leu Pro Lys
```

<210> SEQ ID NO 106
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Alkene moiety at Glu 12

<400> SEQUENCE: 106

Lys Val Pro Gln Val Ser Thr Pro Thr Leu Val Glu Val Ser Arg
1               5                   10                  15

<210> SEQ ID NO 107
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Alkene moiety at Glu 11

<400> SEQUENCE: 107

Arg Pro Cys Phe Ser Ala Leu Thr Pro Asp Glu Thr Tyr Val Pro Lys
1               5                   10                  15

<210> SEQ ID NO 108
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Unsaturated thiol moiety at Glu 2

<400> SEQUENCE: 108

Ser Glu Ile Ala His Arg
1               5

<210> SEQ ID NO 109
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Unsaturated thiol moiety at Asp 4

<400> SEQUENCE: 109

Glu Cys Cys Asp Lys Pro Leu Leu Glu Lys
1               5                   10

<210> SEQ ID NO 110
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE

```
<222> LOCATION: (5)..(5)
<223> OTHER INFORMATION: Alkene moiety at Lys 5

<400> SEQUENCE: 110

Glu Cys Cys Asp Lys Pro Leu Leu Glu Lys
1               5                   10

<210> SEQ ID NO 111
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Unsaturated thiol moiety at Lys 3

<400> SEQUENCE: 111

Phe Asp Lys Phe Lys
1               5

<210> SEQ ID NO 112
<211> LENGTH: 21
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: Unsaturated thiol moiety at Lys 19

<400> SEQUENCE: 112

Lys Lys Gly His His Glu Ala Glu Leu Lys Pro Leu Ala Gln Ser His
1               5                   10                  15

Ala Thr Lys His Lys
            20

<210> SEQ ID NO 113
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene moiety at Lys 3
<220> FEATURE:
<221> NAME/KEY: MISC_FEATURE
<222> LOCATION: (5)..(5)
<223> OTHER INFORMATION: Alkene moiety at Lys 5
<220> FEATURE:
<221> NAME/KEY: MISC_FEATURE
<222> LOCATION: (8)..(8)
<223> OTHER INFORMATION: Unsaturated thiol moiety at Lys 8

<400> SEQUENCE: 113

Phe Asp Lys Phe Lys His Leu Lys Thr Glu Ala Glu Met Lys
1               5                   10

<210> SEQ ID NO 114
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: Unsaturated thiol moiety at Lys 1

<400> SEQUENCE: 114

Lys His Gly Thr Val Val Leu Thr Ala Leu Gly Gly Ile Leu Lys
1               5                   10                  15

<210> SEQ ID NO 115
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene moiety at Lys 2

<400> SEQUENCE: 115

Phe Lys His Leu Lys
1               5

<210> SEQ ID NO 116
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Unsaturated thiol moiety at Lys 2

<400> SEQUENCE: 116

Phe Lys His Leu Lys
1               5

<210> SEQ ID NO 117
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene moiety at Lys 2

<400> SEQUENCE: 117

His Lys Ile Pro Ile Lys
1               5

<210> SEQ ID NO 118
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene moiety at Lys 2

<400> SEQUENCE: 118

His Lys Ile Pro Ile Lys
1               5

<210> SEQ ID NO 119
<211> LENGTH: 19
```

```
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Unsaturated thiol moiety at Lys 8

<400> SEQUENCE: 119

Gly His His Glu Ala Glu Leu Lys Pro Leu Ala Gln Ser His Ala Thr
1               5                   10                  15

Lys His Lys

<210> SEQ ID NO 120
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: Unsaturated thiol moiety at Lys 17

<400> SEQUENCE: 120

Gly His His Glu Ala Glu Leu Lys Pro Leu Ala Gln Ser His Ala Thr
1               5                   10                  15

Lys His Lys

<210> SEQ ID NO 121
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: Alkene moiety at Lys 17

<400> SEQUENCE: 121

Gly His His Glu Ala Glu Leu Lys Pro Leu Ala Gln Ser His Ala Thr
1               5                   10                  15

Lys His Lys

<210> SEQ ID NO 122
<211> LENGTH: 18
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene moiety at Lys 2
<220> FEATURE:
<221> NAME/KEY: MISC_FEATURE
<222> LOCATION: (5)..(5)
<223> OTHER INFORMATION: Unsaturated thiol moiety at Lys 5
<220> FEATURE:
<221> NAME/KEY: MISC_FEATURE
<222> LOCATION: (11)..(11)
<223> OTHER INFORMATION: Alkene moiety at Lys 11

<400> SEQUENCE: 122

Phe Lys His Leu Lys Thr Glu Ala Glu Met Lys Ala Ser Glu Asp Leu
1               5                   10                  15
```

Lys Lys

<210> SEQ ID NO 123
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: Unsaturated thiol moiety at Lys 16

<400> SEQUENCE: 123

```
Tyr Leu Glu Phe Ile Ser Asp Ala Ile Ile His Val Leu His Ser Lys
1               5                   10                  15

His Pro Gly Asp Phe Gly Ala Asp Ala Gln Gly Ala Met Thr Lys
            20                  25                  30
```

<210> SEQ ID NO 124
<211> LENGTH: 31
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: Alkene moiety at Lys 16

<400> SEQUENCE: 124

```
Tyr Leu Glu Phe Ile Ser Asp Ala Ile Ile His Val Leu His Ser Lys
1               5                   10                  15

His Pro Gly Asp Phe Gly Ala Asp Ala Gln Gly Ala Met Thr Lys
            20                  25                  30
```

<210> SEQ ID NO 125
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: Alkene moiety at Lys 14

<400> SEQUENCE: 125

```
His Gly Thr Val Val Leu Thr Ala Leu Gly Gly Ile Leu Lys Lys
1               5                   10                  15
```

<210> SEQ ID NO 126
<211> LENGTH: 18
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Unsaturated thiol moiety at Lys 1

<400> SEQUENCE: 126

```
Lys Gly His His Glu Ala Glu Leu Lys Pro Leu Ala Gln Ser His Ala
1               5                   10                  15

Thr Lys
```

```
<210> SEQ ID NO 127
<211> LENGTH: 18
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Unsaturated thiol moiety at Lys 9

<400> SEQUENCE: 127

Lys Gly His His Glu Ala Glu Leu Lys Pro Leu Ala Gln Ser His Ala
1               5                   10                  15

Thr Lys

<210> SEQ ID NO 128
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene moiety at Lys 6

<400> SEQUENCE: 128

Asn Asp Ile Ala Ala Lys Tyr Lys
1               5

<210> SEQ ID NO 129
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Unsaturated thiol moiety at Lys 6

<400> SEQUENCE: 129

Asn Asp Ile Ala Ala Lys Tyr Lys
1               5

<210> SEQ ID NO 130
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Alkene moiety at Lys 11

<400> SEQUENCE: 130

Leu Phe Thr Gly His Pro Glu Thr Leu Glu Lys Phe Asp Lys
1               5                   10

<210> SEQ ID NO 131
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (11)..(11)
```

<223> OTHER INFORMATION: Unsaturated thiol moiety at Lys 11

<400> SEQUENCE: 131

Leu Phe Thr Gly His Pro Glu Thr Leu Glu Lys Phe Asp Lys
1               5                   10

<210> SEQ ID NO 132
<211> LENGTH: 22
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene moiety at Lys 2

<400> SEQUENCE: 132

His Lys Ile Pro Ile Lys Tyr Leu Glu Phe Ile Ser Asp Ala Ile Ile
1               5                   10                  15

His Val Leu His Ser Lys
            20

<210> SEQ ID NO 133
<211> LENGTH: 22
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene moiety at Lys 6

<400> SEQUENCE: 133

His Lys Ile Pro Ile Lys Tyr Leu Glu Phe Ile Ser Asp Ala Ile Ile
1               5                   10                  15

His Val Leu His Ser Lys
            20

<210> SEQ ID NO 134
<211> LENGTH: 25
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Alkene moiety at Lys 10
<220> FEATURE:
<221> NAME/KEY: MISC_FEATURE
<222> LOCATION: (19)..(19)
<223> OTHER INFORMATION: Unsaturated thiol moiety at Lys 19
<220> FEATURE:
<221> NAME/KEY: MISC_FEATURE
<222> LOCATION: (21)..(21)
<223> OTHER INFORMATION: Alkene moiety at Lys 21

<400> SEQUENCE: 134

Lys Lys Gly His His Glu Ala Glu Leu Lys Pro Leu Ala Gln Ser His
1               5                   10                  15

Ala Thr Lys His Lys Ile Pro Ile Lys
            20                  25

<210> SEQ ID NO 135
<211> LENGTH: 20
<212> TYPE: PRT

```
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Lys 4

<400> SEQUENCE: 135

Ile Pro Ile Lys Tyr Leu Glu Phe Ile Ser Asp Ala Ile Ile His Val
1               5                   10                  15

Leu His Ser Lys
            20

<210> SEQ ID NO 136
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Unsaturated thiol moiety at Lys 11
<220> FEATURE:
<221> NAME/KEY: MISC_FEATURE
<222> LOCATION: (14)..(14)
<223> OTHER INFORMATION: Alkene moiety at Lys 14
<220> FEATURE:
<221> NAME/KEY: MISC_FEATURE
<222> LOCATION: (16)..(16)
<223> OTHER INFORMATION: Unsaturated thiol moiety at Lys 16

<400> SEQUENCE: 136

Leu Phe Thr Gly His Pro Glu Thr Leu Glu Lys Phe Asp Lys Phe Lys
1               5                   10                  15

His Leu Lys

<210> SEQ ID NO 137
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene moiety at Lys 6

<400> SEQUENCE: 137

Thr Glu Ala Glu Met Lys Ala Ser Glu Asp Leu Lys
1               5                   10

<210> SEQ ID NO 138
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene moiety at Lys 6

<400> SEQUENCE: 138

Thr Glu Ala Glu Met Lys Ala Ser Glu Asp Leu Lys Lys
1               5                   10

<210> SEQ ID NO 139
```

```
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene moiety at Lys 3

<400> SEQUENCE: 139

Ala Leu Lys Ala Trp Ser Val Ala Arg
1               5

<210> SEQ ID NO 140
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Unsaturated thiol moiety at Lys 3

<400> SEQUENCE: 140

Ala Leu Lys Ala Trp Ser Val Ala Arg
1               5

<210> SEQ ID NO 141
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Unsaturated thiol moiety at Lys 3

<400> SEQUENCE: 141

Leu Ala Lys Glu Tyr Glu Ala Thr Leu Glu Glu Cys Cys Ala Lys
1               5                   10                  15

<210> SEQ ID NO 142
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene moiety at Lys 7

<400> SEQUENCE: 142

Leu Val Thr Asp Leu Thr Lys Val His Lys
1               5                   10

<210> SEQ ID NO 143
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Unsaturated thiol moiety at Lys 7

<400> SEQUENCE: 143
```

Leu Val Thr Asp Leu Thr Lys Val His Lys
1               5                  10

<210> SEQ ID NO 144
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Alkene moiety at Lys 8

<400> SEQUENCE: 144

Ala Glu Phe Val Glu Val Thr Lys Leu Val Thr Asp Leu Thr Lys
1               5                  10                  15

<210> SEQ ID NO 145
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Unsaturated thiol moiety at Lys 5

<400> SEQUENCE: 145

Ala Asp Leu Ala Lys Tyr Ile Cys Asp Asn Gln Asp Thr Ile Ser Ser
1               5                  10                  15

Lys

<210> SEQ ID NO 146
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Alkene moiety at Lys 10

<400> SEQUENCE: 146

Glu Cys Cys Asp Lys Pro Leu Leu Glu Lys Ser His Cys Ile Ala Glu
1               5                  10                  15

Val Glu Lys

<210> SEQ ID NO 147
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Unsaturated thiol moiety at Lys 5

<400> SEQUENCE: 147

Glu Cys Cys Asp Lys Pro Leu Leu Glu Lys Ser His Cys Ile Ala Glu
1               5                  10                  15

Val Glu Lys

```
<210> SEQ ID NO 148
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Unsaturated thiol moiety at Lys 10

<400> SEQUENCE: 148

Glu Cys Cys Asp Lys Pro Leu Leu Glu Lys Ser His Cys Ile Ala Glu
1               5                   10                  15

Val Glu Lys

<210> SEQ ID NO 149
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Alkene moiety at Lys 6

<400> SEQUENCE: 149

Cys Ala Ser Ile Gln Lys Phe Gly Glu Arg
1               5                   10

<210> SEQ ID NO 150
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Unsaturated thiol moiety at Lys 6

<400> SEQUENCE: 150

Cys Ala Ser Ile Gln Lys Phe Gly Glu Arg
1               5                   10

<210> SEQ ID NO 151
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Unsaturated thiol moiety at Lys 7

<400> SEQUENCE: 151

Leu Cys Val Leu His Glu Lys Thr Pro Val Ser Glu Lys
1               5                   10

<210> SEQ ID NO 152
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
```

<223> OTHER INFORMATION: Unsaturated thiol moiety at Lys 3

<400> SEQUENCE: 152

Val Thr Lys Cys Cys Thr Glu Ser Leu Val Asn Arg
1               5                   10

<210> SEQ ID NO 153
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Lys 4

<400> SEQUENCE: 153

Ser Leu Gly Lys Val Gly Thr Arg
1               5

<210> SEQ ID NO 154
<211> LENGTH: 25
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Unsaturated thiol moiety at Lys 7
<220> FEATURE:
<221> NAME/KEY: MISC_FEATURE
<222> LOCATION: (13)..(13)
<223> OTHER INFORMATION: Unsaturated thiol moiety at Lys 13
<220> FEATURE:
<221> NAME/KEY: MISC_FEATURE
<222> LOCATION: (16)..(16)
<223> OTHER INFORMATION: Alkene moiety at Lys 16

<400> SEQUENCE: 154

Leu Cys Val Leu His Glu Lys Thr Pro Val Ser Glu Lys Val Thr Lys
1               5                   10                  15

Cys Cys Thr Glu Ser Leu Val Asn Arg
            20                  25

<210> SEQ ID NO 155
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Unsaturated thiol moiety at Lys 2

<400> SEQUENCE: 155

Phe Lys Asp Leu Gly Glu Glu His Phe Lys
1               5                   10

<210> SEQ ID NO 156
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)

<223> OTHER INFORMATION: Alkene moiety at Lys 2

<400> SEQUENCE: 156

Phe Lys Asp Leu Gly Glu Glu His Phe Lys
1               5                   10

<210> SEQ ID NO 157
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Unsaturated thiol moiety at Lys 3

<400> SEQUENCE: 157

Phe Pro Lys Ala Glu Phe Val Glu Val Thr Lys
1               5                   10

<210> SEQ ID NO 158
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene moiety at Lys 3

<400> SEQUENCE: 158

Phe Pro Lys Ala Glu Phe Val Glu Val Thr Lys
1               5                   10

<210> SEQ ID NO 159
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Unsaturated thiol moiety at Lys 12

<400> SEQUENCE: 159

Tyr Ile Cys Asp Asn Gln Asp Thr Ile Ser Ser Lys Leu Lys
1               5                   10

<210> SEQ ID NO 160
<211> LENGTH: 23
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Alkene moiety at Lys 10

<400> SEQUENCE: 160

Leu Val Asn Glu Leu Thr Glu Phe Ala Lys Thr Cys Val Ala Asp Glu
1               5                   10                  15

Ser His Ala Gly Cys Glu Lys
            20

```
<210> SEQ ID NO 161
<211> LENGTH: 29
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: Alkene moiety at Lys 15

<400> SEQUENCE: 161

His Pro Tyr Phe Tyr Ala Pro Glu Leu Leu Tyr Tyr Ala Asn Lys Tyr
1               5                   10                  15

Asn Gly Val Phe Gln Glu Cys Cys Gln Ala Glu Asp Lys
            20                  25

<210> SEQ ID NO 162
<211> LENGTH: 29
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (15)..(15)
<223> OTHER INFORMATION: Unsaturated thiol moiety at Lys 15

<400> SEQUENCE: 162

His Pro Tyr Phe Tyr Ala Pro Glu Leu Leu Tyr Tyr Ala Asn Lys Tyr
1               5                   10                  15

Asn Gly Val Phe Gln Glu Cys Cys Gln Ala Glu Asp Lys
            20                  25

<210> SEQ ID NO 163
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Alkene moiety at Lys 7
<220> FEATURE:
<221> NAME/KEY: MISC_FEATURE
<222> LOCATION: (11)..(11)
<223> OTHER INFORMATION: Oxidation at Met 11

<400> SEQUENCE: 163

Gly Ala Cys Leu Leu Pro Lys Ile Glu Thr Met Arg
1               5                   10

<210> SEQ ID NO 164
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Lys 4

<400> SEQUENCE: 164

His Lys Pro Lys Ala Thr Glu Glu Gln Leu Lys
1               5                   10

<210> SEQ ID NO 165
```

```
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Unsaturated thiol moiety at Lys 4

<400> SEQUENCE: 165

His Lys Pro Lys Ala Thr Glu Glu Gln Leu Lys
1               5                   10

<210> SEQ ID NO 166
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene moiety at Lys 2

<400> SEQUENCE: 166

His Lys Pro Lys Ala Thr Glu Glu Gln Leu Lys
1               5                   10

<210> SEQ ID NO 167
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Alkene moiety at Lys 1

<400> SEQUENCE: 167

Lys Gln Thr Ala Leu Val Glu Leu Leu Lys
1               5                   10

<210> SEQ ID NO 168
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Unsaturated thiol moiety at Lys 7
<220> FEATURE:
<221> NAME/KEY: MISC_FEATURE
<222> LOCATION: (10)..(10)
<223> OTHER INFORMATION: Oxidation at Met 10

<400> SEQUENCE: 168

Ala Thr Glu Glu Gln Leu Lys Thr Val Met Glu Asn Phe Val Ala Phe
1               5                   10                  15

Val Asp Lys

<210> SEQ ID NO 169
<211> LENGTH: 19
<212> TYPE: PRT
<213> ORGANISM: Artificial
<220> FEATURE:
<223> OTHER INFORMATION: Synthetic
```

```
<220> FEATURE:
<221> NAME/KEY: MISC_FEATURE
<222> LOCATION: (7)..(7)
<223> OTHER INFORMATION: Alkene moiety at Lys 7
<220> FEATURE:
<221> NAME/KEY: MISC_FEATURE
<222> LOCATION: (10)..(10)
<223> OTHER INFORMATION: Oxidation at Met 10

<400> SEQUENCE: 169

Ala Thr Glu Glu Gln Leu Lys Thr Val Met Glu Asn Phe Val Ala Phe
1               5                   10                  15

Val Asp Lys

<210> SEQ ID NO 170
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Lys 4

<400> SEQUENCE: 170

Phe Trp Gly Lys Tyr Leu Tyr Glu Ile Ala Arg
1               5                   10

<210> SEQ ID NO 171
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Lys 4

<400> SEQUENCE: 171

Leu Ser Gln Lys Phe Pro Lys
1               5

<210> SEQ ID NO 172
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: Alkene moiety at Lys 16

<400> SEQUENCE: 172

Leu Phe Thr Phe His Ala Asp Ile Cys Thr Leu Pro Asp Thr Glu Lys
1               5                   10                  15

Gln Ile Lys

<210> SEQ ID NO 173
<211> LENGTH: 29
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (16)..(16)
```

```
<223> OTHER INFORMATION: Unsaturated thiol moiety at Lys 16

<400> SEQUENCE: 173

Asn Glu Cys Phe Leu Ser His Lys Asp Asp Ser Pro Asp Leu Pro Lys
1               5                   10                  15

Leu Lys Pro Asp Pro Asn Thr Leu Cys Asp Glu Phe Lys
            20                  25

<210> SEQ ID NO 174
<211> LENGTH: 21
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Unsaturated thiol moiety at Lys 8

<400> SEQUENCE: 174

Asp Asp Ser Pro Asp Leu Pro Lys Leu Lys Pro Asp Pro Asn Thr Leu
1               5                   10                  15

Cys Asp Glu Phe Lys
            20

<210> SEQ ID NO 175
<211> LENGTH: 21
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Unsaturated thiol moiety at Lys 10

<400> SEQUENCE: 175

Asp Asp Ser Pro Asp Leu Pro Lys Leu Lys Pro Asp Pro Asn Thr Leu
1               5                   10                  15

Cys Asp Glu Phe Lys
            20

<210> SEQ ID NO 176
<211> LENGTH: 21
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Unsaturated thiol moiety at Lys 8

<400> SEQUENCE: 176

Gln Asn Cys Asp Gln Phe Glu Lys Leu Gly Glu Tyr Gly Phe Gln Asn
1               5                   10                  15

Ala Leu Ile Val Arg
            20

<210> SEQ ID NO 177
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
```

<222> LOCATION: (1)..(1)
<223> OTHER INFORMATION: Alkene moiety at Lys 1

<400> SEQUENCE: 177

Lys Val Pro Gln Val Ser Thr Pro Thr Leu Val Glu Val Ser Arg
1               5                   10                  15

<210> SEQ ID NO 178
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl moiety at Ser 1

<400> SEQUENCE: 178

Ser Ala Lys Ala Tyr Glu His Arg
1               5

<210> SEQ ID NO 179
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl moiety at Ser 1

<400> SEQUENCE: 179

Ser Ala Lys Ala Tyr Glu Ala His Arg
1               5

<210> SEQ ID NO 180
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl moiety at Ser 1

<400> SEQUENCE: 180

Ser Ala Lys Ala Tyr Glu Thr His Arg
1               5

<210> SEQ ID NO 181
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl moiety at Ser 1
<220> FEATURE:
<221> NAME/KEY: MISC_FEATURE
<222> LOCATION: (6)..(6)
<223> OTHER INFORMATION: Inter-peptide linkage at Glu 6

<400> SEQUENCE: 181

Ser Ala Lys Ala Tyr Glu His Arg
1               5

```
<210> SEQ ID NO 182
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Alkene moiety at Glu 3

<400> SEQUENCE: 182

Ala Ser Glu Asp Leu Lys Lys
1               5

<210> SEQ ID NO 183
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Unsaturated thiol moiety at Asp 4

<400> SEQUENCE: 183

Val Glu Ala Asp Ile Ala Gly His Gly Gln Glu Val Leu Ile Arg
1               5                   10                  15

<210> SEQ ID NO 184
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Alkene moiety at Glu 2

<400> SEQUENCE: 184

Leu Val Asn Glu Leu Thr Glu Phe Ala Lys
1               5                   10

<210> SEQ ID NO 185
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Unsaturated thiol moiety at Glu 2

<400> SEQUENCE: 185

Ser Leu His Thr Leu Phe Gly Asp Glu Leu Cys Lys
1               5                   10

<210> SEQ ID NO 186
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
```

<223> OTHER INFORMATION: Alkene moiety at Glu 3
<220> FEATURE:
<221> NAME/KEY: MISC_FEATURE
<222> LOCATION: (7)..(7)
<223> OTHER INFORMATION: Unsaturated thiol moiety at Asp 7

<400> SEQUENCE: 186

Tyr Leu Glu Phe Ile Ser Asp Ala Ile Ile His Val Leu His Ser Lys
1               5                   10                  15

<210> SEQ ID NO 187
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Unsaturated thiol moiety at Glu 3
<220> FEATURE:
<221> NAME/KEY: MISC_FEATURE
<222> LOCATION: (7)..(7)
<223> OTHER INFORMATION: Alkene moiety at Asp 7

<400> SEQUENCE: 187

Tyr Leu Glu Phe Ile Ser Asp Ala Ile Ile His Val Leu His Ser Lys
1               5                   10                  15

<210> SEQ ID NO 188
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Alkene moiety at Glu 2

<400> SEQUENCE: 188

Val Glu Ala Asp Ile Ala Gly His Gly Gln Glu Val Leu Ile Arg
1               5                   10                  15

<210> SEQ ID NO 189
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Unsaturated thiol moiety at Glu 2

<400> SEQUENCE: 189

Val Glu Ala Asp Ile Ala Gly His Gly Gln Glu Val Leu Ile Arg
1               5                   10                  15

<210> SEQ ID NO 190
<211> LENGTH: 21
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: Alkene moiety at Glu 18

<400> SEQUENCE: 190

```
Gly Leu Val Leu Ile Ala Phe Ser Gln Tyr Leu Gln Gln Cys Pro Phe
1               5                   10                  15

Asp Glu His Val Lys
            20
```